US009251713B1

(12) United States Patent
Giovanniello et al.

(10) Patent No.: US 9,251,713 B1
(45) Date of Patent: Feb. 2, 2016

(54) SYSTEM AND PROCESS FOR ASSESSING A USER AND FOR ASSISTING A USER IN REHABILITATION

(71) Applicant: Anthony Joseph Giovanniello, Rockville Centre, NY (US)

(72) Inventors: Matthew Joseph Giovanniello, Rockville Centre, NY (US); Anthony Joseph Giovanniello, Rockville Centre, NY (US); Christopher Patterson, Farmingdale, NY (US)

(73) Assignee: Anthony J. Giovanniello, Rockville Centre, NY (US)

( * ) Notice: Subject to any disclaimer, the term of this patent is extended or adjusted under 35 U.S.C. 154(b) by 16 days.

(21) Appl. No.: 13/681,871

(22) Filed: Nov. 20, 2012

(51) Int. Cl.
G09B 5/00 (2006.01)
G09B 23/00 (2006.01)
G06Q 50/22 (2012.01)

(52) U.S. Cl.
CPC ........... *G09B 5/00* (2013.01); *G06Q 50/22* (2013.01); *G09B 23/00* (2013.01)

(58) Field of Classification Search
CPC .................................... G09B 5/00; G09B 5/23
USPC .................................................. 434/236, 238
See application file for complete search history.

(56) References Cited

U.S. PATENT DOCUMENTS 5,596,994 A * 1/1997 Bro .............................. 600/545
5,897,493 A * 4/1999 Brown .......................... 600/300
5,911,581 A 6/1999 Reynolds et al.
5,985,559 A * 11/1999 Brown ......................... 435/6.11
6,225,920 B1 5/2001 Dayle
6,334,778 B1 * 1/2002 Brown .......................... 434/258
6,632,174 B1 10/2003 Breznitz
6,820,037 B2 * 11/2004 Simon ........................... 702/182
7,931,535 B2 4/2011 Ikeda et al.
2001/0039503 A1 * 11/2001 Chan et al. ....................... 705/2
2002/0133377 A1 * 9/2002 Brown ........................... 705/3
2002/0187463 A1 * 12/2002 Aspe et al. ..................... 434/362
2003/0129574 A1 7/2003 Ferriol et al.
2003/0212579 A1 * 11/2003 Brown et al. ..................... 705/2
2004/0167380 A1 * 8/2004 Simon ........................... 600/300
2006/0129324 A1 6/2006 Rabinoff et al.
2006/0252014 A1 * 11/2006 Simon et al. .................. 434/236
2007/0033072 A1 * 2/2007 Bildirici ........................... 705/3
2007/0106127 A1 * 5/2007 Alman .......................... 600/300
2007/0179361 A1 * 8/2007 Brown et al. ................... 600/300
2008/0057483 A1 * 3/2008 Avidan .......................... 434/362
2008/0154638 A1 6/2008 Coyle et al.
2008/0228043 A1 9/2008 Kenedy et al.
2009/0018407 A1 1/2009 Jung et al.
2009/0083071 A1 3/2009 Phillips et al.

(Continued)

OTHER PUBLICATIONS

Family Questionnaire. National Chronic Care Consortium and the Alzheimer's Association Revised May 2003.*

*Primary Examiner* — Robert J Utama
(74) *Attorney, Agent, or Firm* — Collard & Roe, P.C.

(57) ABSTRACT

There is disclosed a system and process for diagnosing or determining a condition of a user. In particular the system and process can be used to provide a series of questions based upon personalized information of the user. This personalized information can be uploaded to a database. A series of questions can be automatically generated or a user can be assisted in creating a series of questions for a patient based upon this uploaded media. In addition, the system and process can use this personalized media to treat the patient and to assist the patient in their daily tasks.

22 Claims, 49 Drawing Sheets

(56) References Cited

U.S. PATENT DOCUMENTS

| | | |
|---|---|---|
| 2009/0118588 A1 | 5/2009 | Robinson et al. |
| 2009/0234181 A1 | 9/2009 | Kim |
| 2009/0271347 A1 | 10/2009 | Hyde et al. |
| 2010/0004762 A1 | 1/2010 | Leuthardt et al. |
| 2010/0017231 A1 | 1/2010 | Galbraith et al. |
| 2010/0092929 A1* | 4/2010 | Hallowell et al. ............ 434/167 |
| 2010/0241449 A1 | 9/2010 | Firminger et al. |
| 2010/0268057 A1 | 10/2010 | Firminger et al. |
| 2010/0274574 A1* | 10/2010 | Andersson et al. ............... 705/2 |
| 2010/0298649 A1* | 11/2010 | Warkentin et al. ........... 600/300 |
| 2011/0059798 A1 | 3/2011 | Pryor |
| 2011/0118555 A1* | 5/2011 | Dhumne et al. ............. 600/300 |
| 2012/0021391 A1 | 1/2012 | Elsmore et al. |
| 2012/0021394 A1 | 1/2012 | deCharms |

* cited by examiner

FIG. 5

| Determine Age | 501 |

| DETERMINE WHETHER THERE IS A MEDICAL DIAGNOSIS | 502 |

| DETERMINE WHETHER THERE ARE ANY MOOD SWINGS/ ANGER, AGITATION, RESISTANCE | 503 |

| DETERMINE TIME OF DAY WHEN PATIENT IS MOST ALERT | 504 |

| DETERMINE TIME OF DAY WHEN PATIENT IS MORE TIRED | 505 |

| DETERMINE THE AMOUNT OF SLEEP THAT THE PATIENT REQUIRES | 506 |

| DETERMINE PHYSICAL LIMITATIONS | 507 |

| DETERMINE SHORT TERM MEMORIES | 508 |

| DETERMINE LONG TERM MEMORIES | 509 |

| DETERMINE LEVEL OF EXECUTIVE FUNCTIONING | 510 |

FIG. 7A

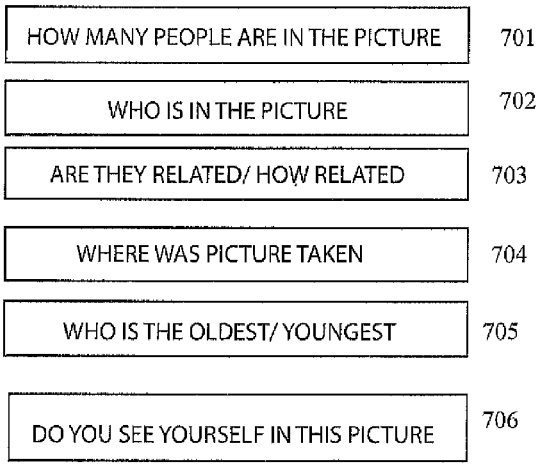

| HOW MANY PEOPLE ARE IN THE PICTURE | 701 |
| WHO IS IN THE PICTURE | 702 |
| ARE THEY RELATED/ HOW RELATED | 703 |
| WHERE WAS PICTURE TAKEN | 704 |
| WHO IS THE OLDEST/ YOUNGEST | 705 |
| DO YOU SEE YOURSELF IN THIS PICTURE | 706 |

FIG. 7C

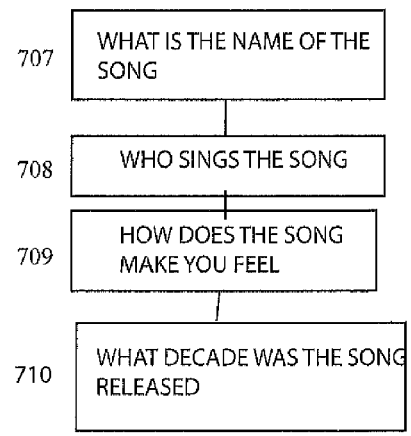

| 707 | WHAT IS THE NAME OF THE SONG |
| 708 | WHO SINGS THE SONG |
| 709 | HOW DOES THE SONG MAKE YOU FEEL |
| 710 | WHAT DECADE WAS THE SONG RELEASED |

FIG. 7B

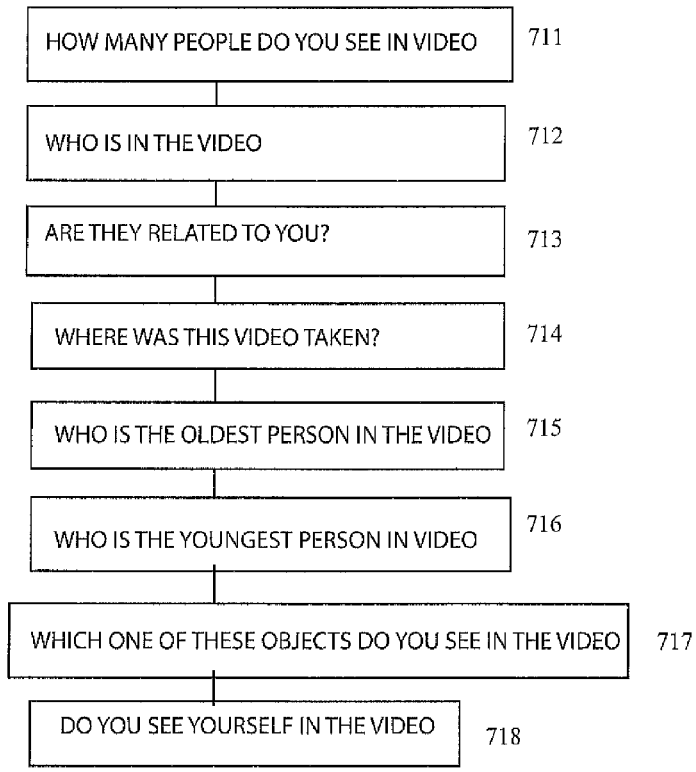

| HOW MANY PEOPLE DO YOU SEE IN VIDEO | 711 |
| WHO IS IN THE VIDEO | 712 |
| ARE THEY RELATED TO YOU? | 713 |
| WHERE WAS THIS VIDEO TAKEN? | 714 |
| WHO IS THE OLDEST PERSON IN THE VIDEO | 715 |
| WHO IS THE YOUNGEST PERSON IN VIDEO | 716 |
| WHICH ONE OF THESE OBJECTS DO YOU SEE IN THE VIDEO | 717 |
| DO YOU SEE YOURSELF IN THE VIDEO | 718 |

FIG. 8

| | |
|---|---|
| 801 | DETERMINE TYPE OF SPEECH FLUENT/ NON FLUENT |
| 802 | DETERMINE LEVEL OF COMPREHENSION |
| 803 | PROVIDE REPETITION |
| 804 | DETERMINE LEVEL OF REPETITION |
| 805 | CONDUCT OBJECT NAMING |
| 806 | PROVIDE DETERMINATION/DIAGNOSIS |

FIG. 12

LEVELS OF RESPONSIBILITY (all members of any given level have
equal power and/or responsibility)

MEDICAL:

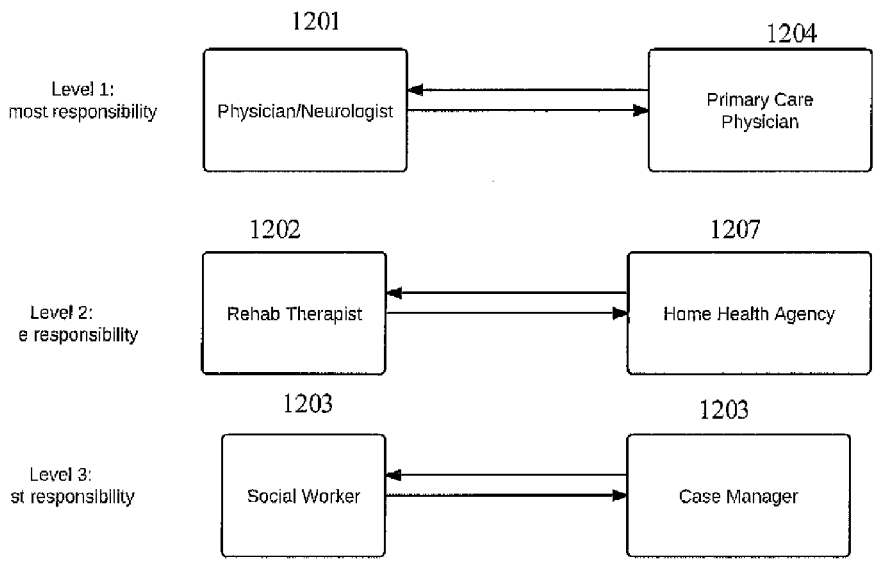

FAMILY:

FIG. 13

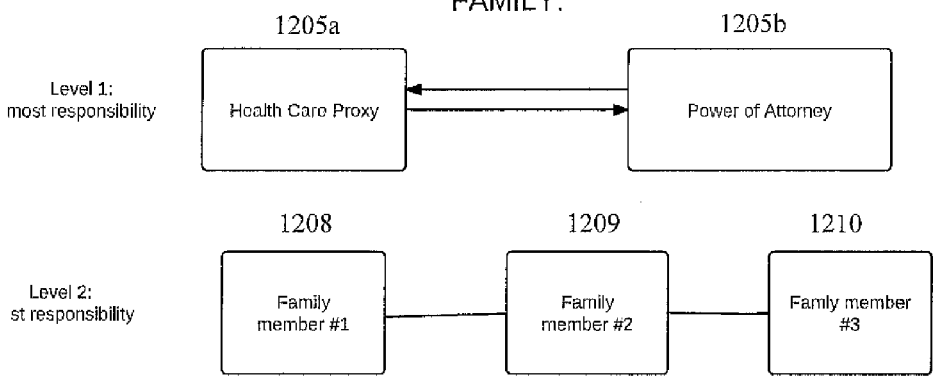

*level 2 family members function is to receive emergency phone calls - phone call is routed to Family member #2
if #1 unavailable and to #3 if 2 is unavailable

**family member can consult with Health Care Proxy if medical question or Power of Attorney if nonmedical life
questions

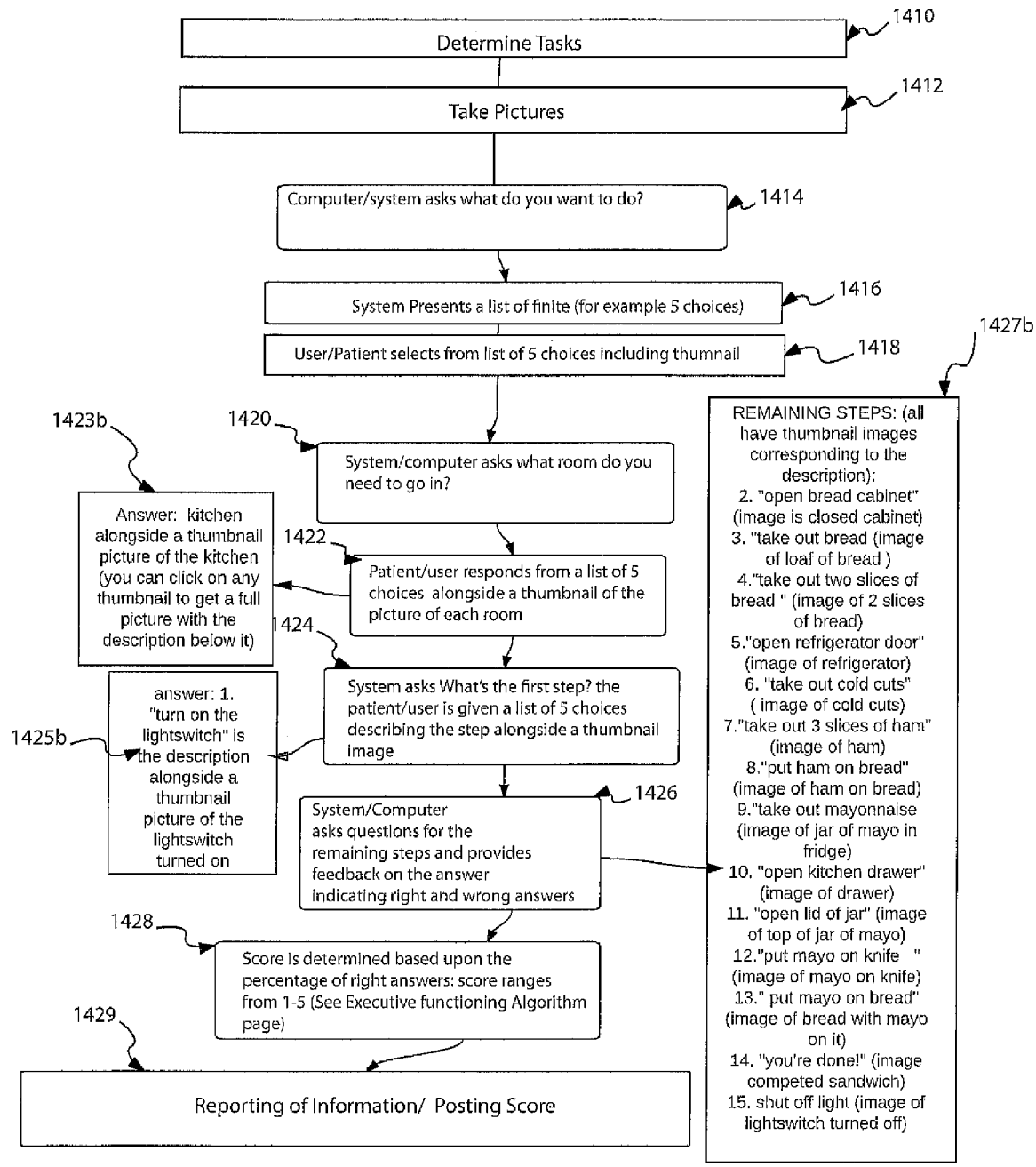

1670

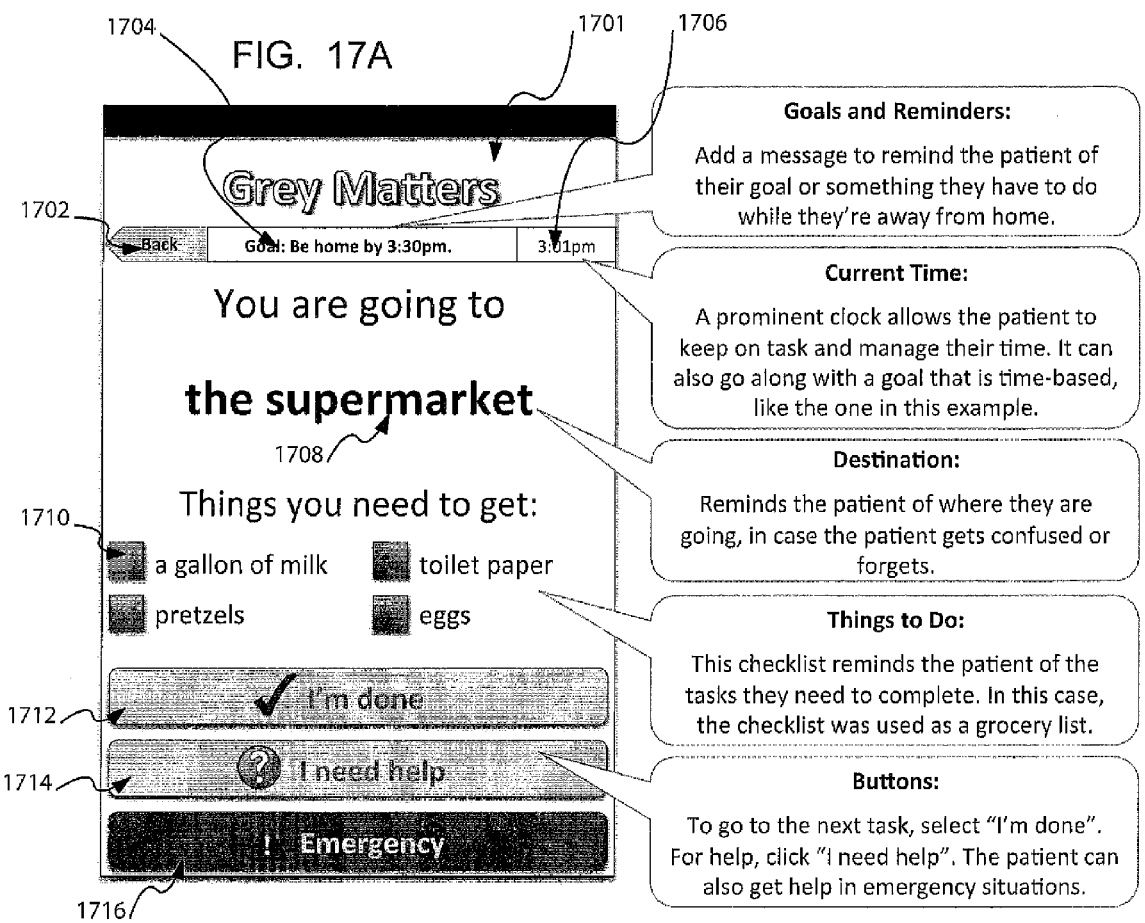

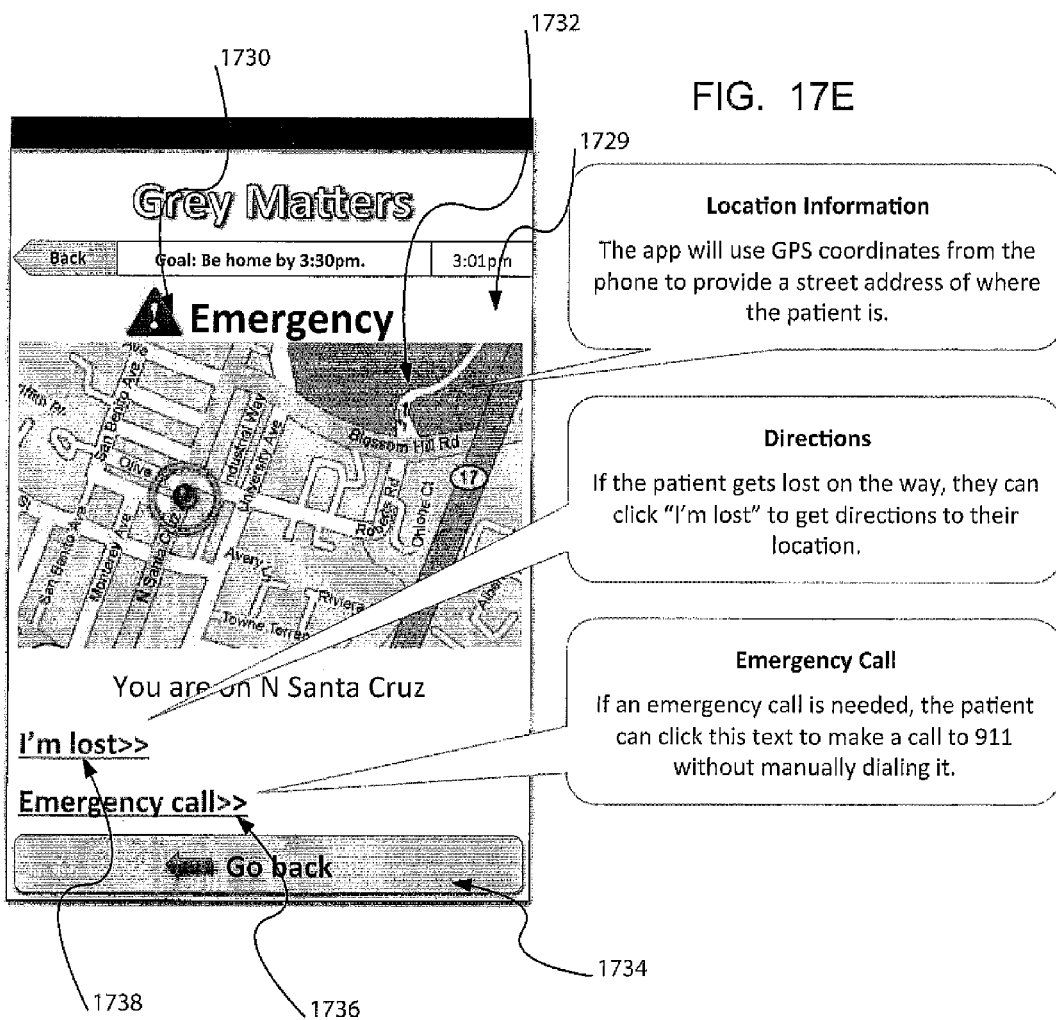

SYSTEM AND PROCESS FOR ASSESSING A USER AND FOR ASSISTING A USER IN REHABILITATION

BACKGROUND OF THE INVENTION

At least one embodiment of the invention relates to a system and a process for providing assistance and cognitive stimulation to a user/patient to assess the abilities of the patient and to assist the patient with treatment as well as daily tasks. This system and process can include uploading personalized information about a user into a computer system and then presenting a series of questions to a user to assess the abilities of that user and to provide rehabilitative care to that user. This system and process can be used to help a medical professional diagnose a plurality of different medical conditions. For example, one medical condition is anomie aphasia which is also known as dysnomia which equates with a persona having a severe problem with recalling words or names. Another condition can include Wernicke's aphasia which is a language disorder that impacts language comprehension and production of meaningful language. The disorder is associated with the damage to the Wernicke's area. Individuals with Wernicke's aphasia have difficulty understanding spoken language but are able to produce sounds phrases and word sequences. These sentences/word sequences are grammatically correct but nonsensical thereby limiting the ability of patients to communicate. Transcortial aphasia (TMA) is similar to Wernicke's aphasia but the repetition is intact. This condition can be caused by a stroke. People who suffer from TMA have severely impaired writing ability. Global Aphasia is one where the person has a near complete loss of ability to formulate verbal communication. In this case, speech is reduced to a few words. Brocas aphasia is one of the most common or recognized type of aphasia wherein the patient has good comprehension but has difficulty speaking. Aside from assisting patients with strokes, memory deficits from Alzheimer's Disease, or other brain injuries such as traumatic brain injury or encephalitis, this invention can be useful in the field of Psychiatry as well. Patients with Chronic Schizophrenia often suffer from lingering cognitive deficits after their psychotic symptoms have been successfully treated. They often have difficulty with motivation, relating to others, and may be lacking the skills of executive functioning as well.

There have been systems created to test and train cognitive abilities. Some of these systems can include U.S. Patent Application publication No. 2009/0118588 to Robinson et al published on May 7, 2009 and U.S. Patent Application Publication No. 2009/0234181 to Kim published on Sep. 17, 2009, wherein the disclosures and teachings of both of these publications are hereby incorporated herein by reference. It has been determined that there is a need for a customizable computerized system and process for providing personalized therapy to a patient to diagnose or determine a condition of a patient and to treat a patient.

SUMMARY OF THE INVENTION

At least one embodiment of the invention relates to a system and process for diagnosing or determining a condition of a user. In particular, the system and process can be used to provide a series of questions based upon personalized information of the user. This personalized information can be uploaded to a database. A series of questions can be automatically generated or a user can be assisted in creating a series of questions for a patient based upon this uploaded media. In addition, the system and process can use this personalized media to treat the patient and to assist the patient in their daily tasks.

BRIEF DESCRIPTION OF THE DRAWINGS

Other objects and features of the present invention will become apparent from the following detailed description considered in connection with the accompanying drawings which disclose at least one embodiment of the present invention. It should be understood, however, that the drawings are designed for the purpose of illustration only and not as a definition of the limits of the invention.

In the drawings, wherein similar reference characters denote similar elements throughout the several views:

FIG. 4 is a flowchart of the process for determining the fluent speech level for a user;

FIG. 5 is a flowchart of the process for gathering information for the user;

FIG. 7A is a flowchart of the process for gathering information about a picture;

FIG. 7B is a flowchart of the process for obtaining information about a particular video;

FIG. 7C is a flowchart of the process for obtaining information about a music file or song;

FIG. 8 is a flowchart of the process for conducting speech therapy and for obtaining information about this speech therapy;

FIG. 12 is a flowchart of the process for reporting hierarchy of a communication to a user;

FIG. 13 is a flowchart of the process for determining the levels of responsibility.

FIG. 14C is a flow chart for creating a second task;

FIG. 17A is another screen for an additional task which occurs outside of the patient's home;

FIG. 17E is a screen indicating to the user that they are in an emergency;

DETAILED DESCRIPTION

Figure 1A:
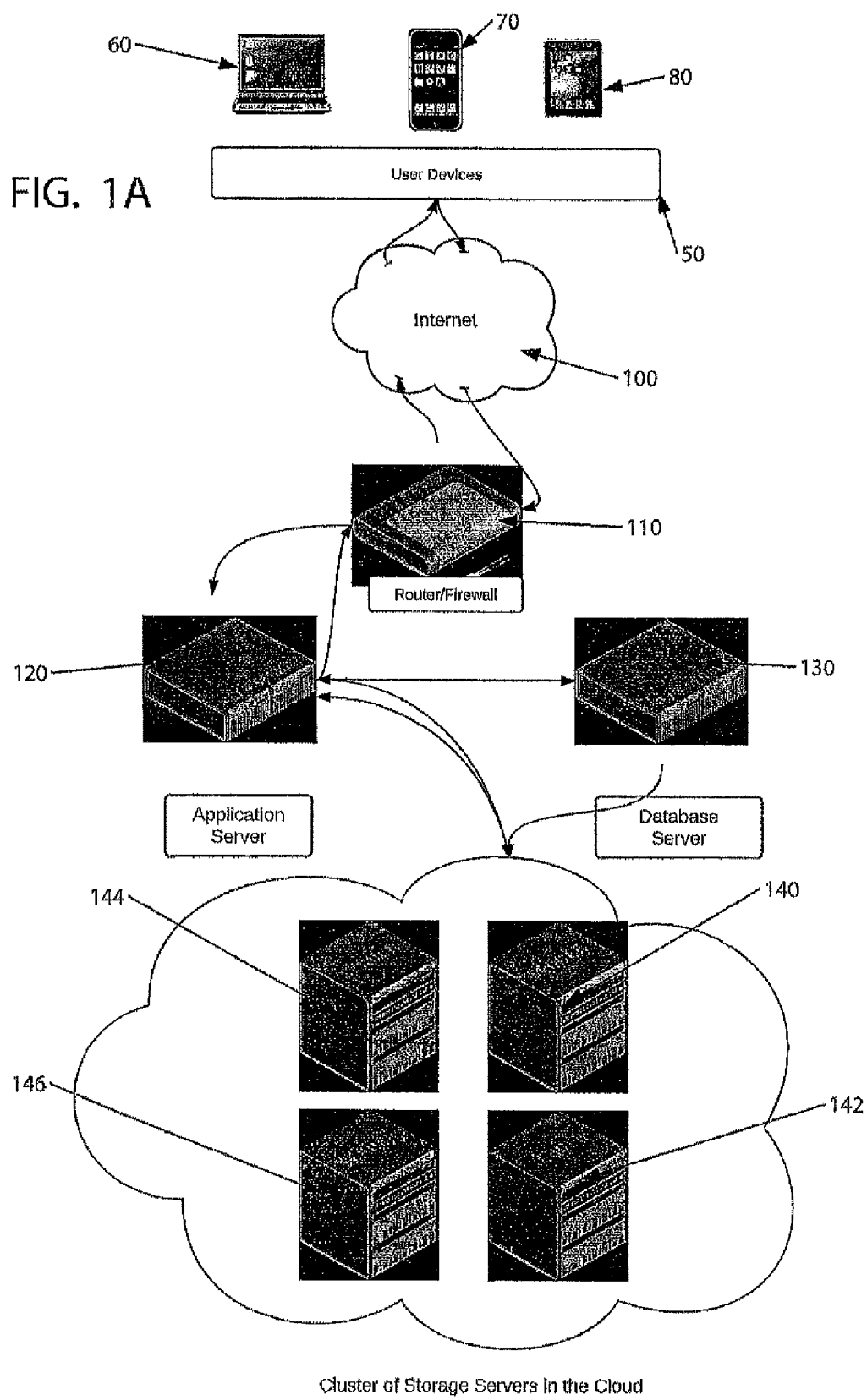
FIG. 1A is as schematic block diagram of a computer server layout which is configured to perform the process outlined in FIGS. 3-17G below.

FIG. 1A is a first layout of a computer system for performing the functions as shown in many of the remaining FIGS. For example, FIG. 1 shows a plurality of remote computers comprising a laptop computer 60, a handheld computer 70 or a tablet computer 80. Alternative forms of computing devices can also be shown as well such as desktop computers as well. In this case, these computers can interface or communicate through a network connection to the internet 100. On the other side of the internet 100 are a plurality of servers protected by a firewall or router 110. This router 110 is configured to provide limited or selected access to an application server 120 or a database server 130. In addition, in communication with these servers is a plurality of storage servers 140, 142, 144, 146. These storage servers are configured to store data such as but not limited to music files, data files, video files, pictures etc.

Figure 1B:
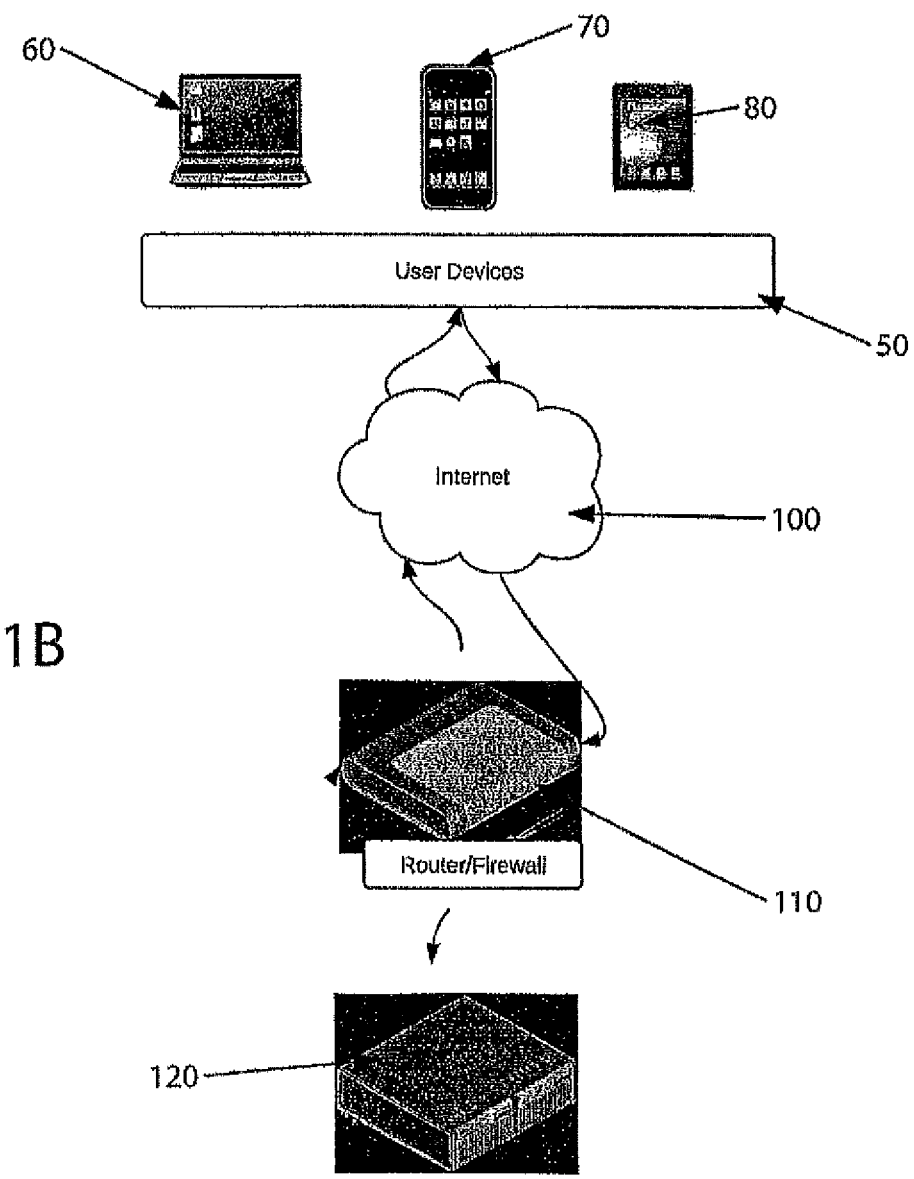
FIG. 1B is a schematic block diagram of another alternative form of a server layout.

In another embodiment, as shown in FIG. 1B there are a plurality of computing devices 60, 70, 80 which are in communication through the internet 100 to a router or firewall 110. This router can then route the information to a single server such as an application server 120. This single application server 129 can serve as all of the servers above including but not limited to an application server 120, a database server 130 as well as a storage server such as servers 140, 142, 144, 146 to form a simplified system.

Figure 2A:
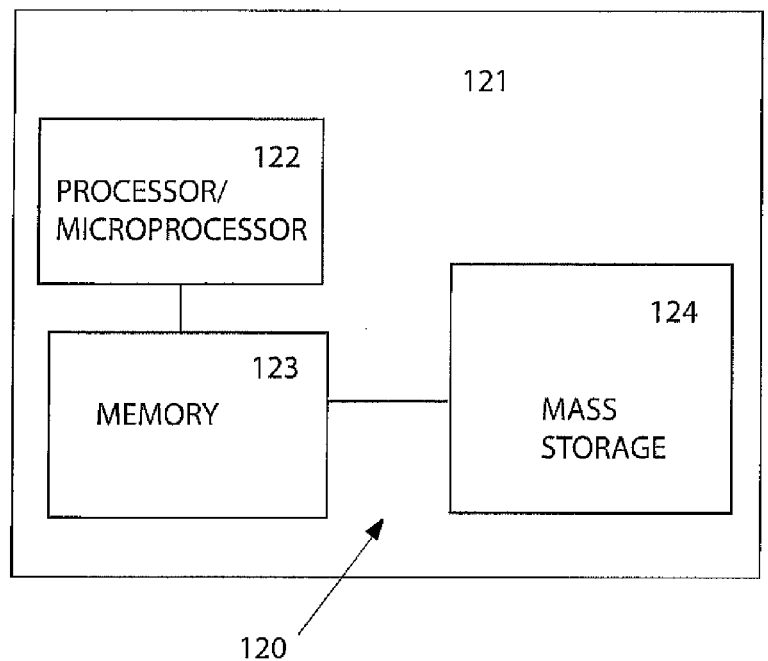
FIG. 2A is a block diagram of a layout of the internal components a computer such as the application server.

FIG. 2A shows a layout of a server such as application server 120. This layout of the server includes a motherboard 121, a processor 122, a memory 123, and a mass storage 124. This system is configured and programmed via programming configured to work with at least one processor such as a microprocessor 122 on application server 120 to proceed through a series of steps in order to help or assist a patient. A program which resides on mass storage device 124 is uploaded into memory 123 wherein these series of instructions are then fed into processor 122. Processor 122 is configured as a microprocessor and is configured to perform a series of step based upon instructions provided to processor from memory 123.

Figure 2B:
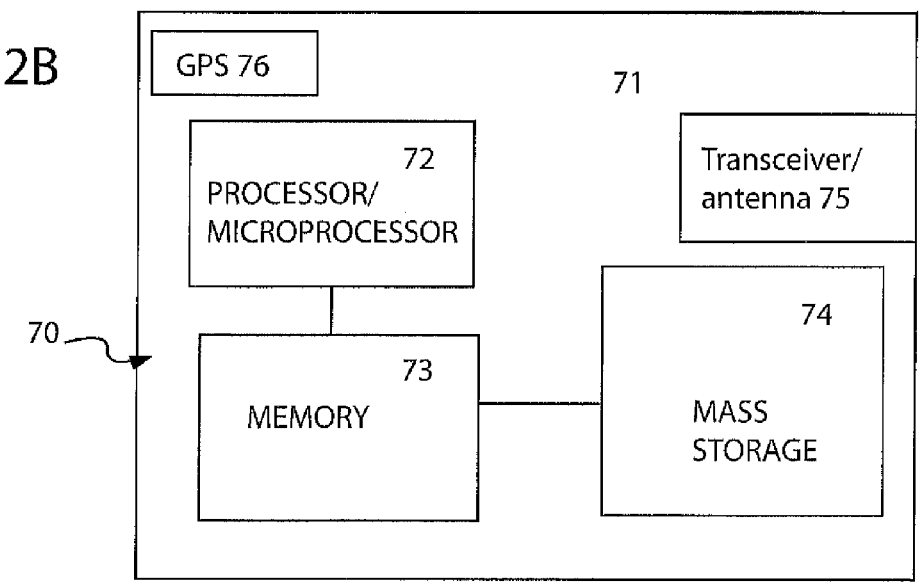
FIG. 2B is a block diagram of a layout of the internal components of a portable computer such as a smart phone.

In addition an example of the components of mobile computing device 70 or phone is shown in FIG. 2B. For example, there is shown a motherboard 71, a processor such as a microprocessor 72, a memory such as a RAM or EEPROM 73 an optional mass storage device 74 such as a hard drive, a transceiver 75 which can communicate wirelessly through WIFI such as 802.11x communications, or cellular communications, and a GPS communicator 76 which communicates with GPS tracking satellites to determine the mobile computing device's location.

For both the server 120 and the portable computing device 70, these components can be as follows: processor 72 or 122 can be a microprocessor manufactured from Intel® or Advanced Micro Devices (AMD)® or any other suitable processor manufacturer. Memory 73, 123 can be any form of suitable memory such as RAM, or flash memory such as EEPROM. Mass storage 74, 124 can be integrated with memory 73, 123 respectively or a separate component and can be in the form of one or more hard drives or one or more solid state drives or any combination in between. In addition, transceiver antenna configuration 75 can be made from any suitable WIFI system or SIM or CDMA configuration, while GPS communicator can be configured from any suitable GPS system.

These electronic components can be configured to perform the steps in FIGS. 3-17G. For example, in a first configuration the process can be controlled by the system which can essentially be application server 120 running a program having instructions which result in the process shown in FIG. 3-17G. With this design, remote portable computing device for example, can act as a dumb terminal wherein all or most of the computing, calculations and storage are performed remotely such as being controlled by application server 120. In that case, microprocessor 122 would be programmed to perform most or all of the steps outlined in FIGS. 3-17G. Alternatively, the system could operate as a hybrid wherein some of the steps are performed by microprocessor 122 and some of the steps are performed by microprocessor 72. Alternatively, the system could be configured such that microprocessor 72 can be programmed to perform all or most of the processing and steps outlined in FIGS. 3-17G.

As a default, and for purposes of the discussion of the process described hereinafter the processing and steps are performed by microprocessor 72 in the local portable computer 70, and stored either in memory 73 or mass storage 74 unless indicated otherwise.

Figure 3:
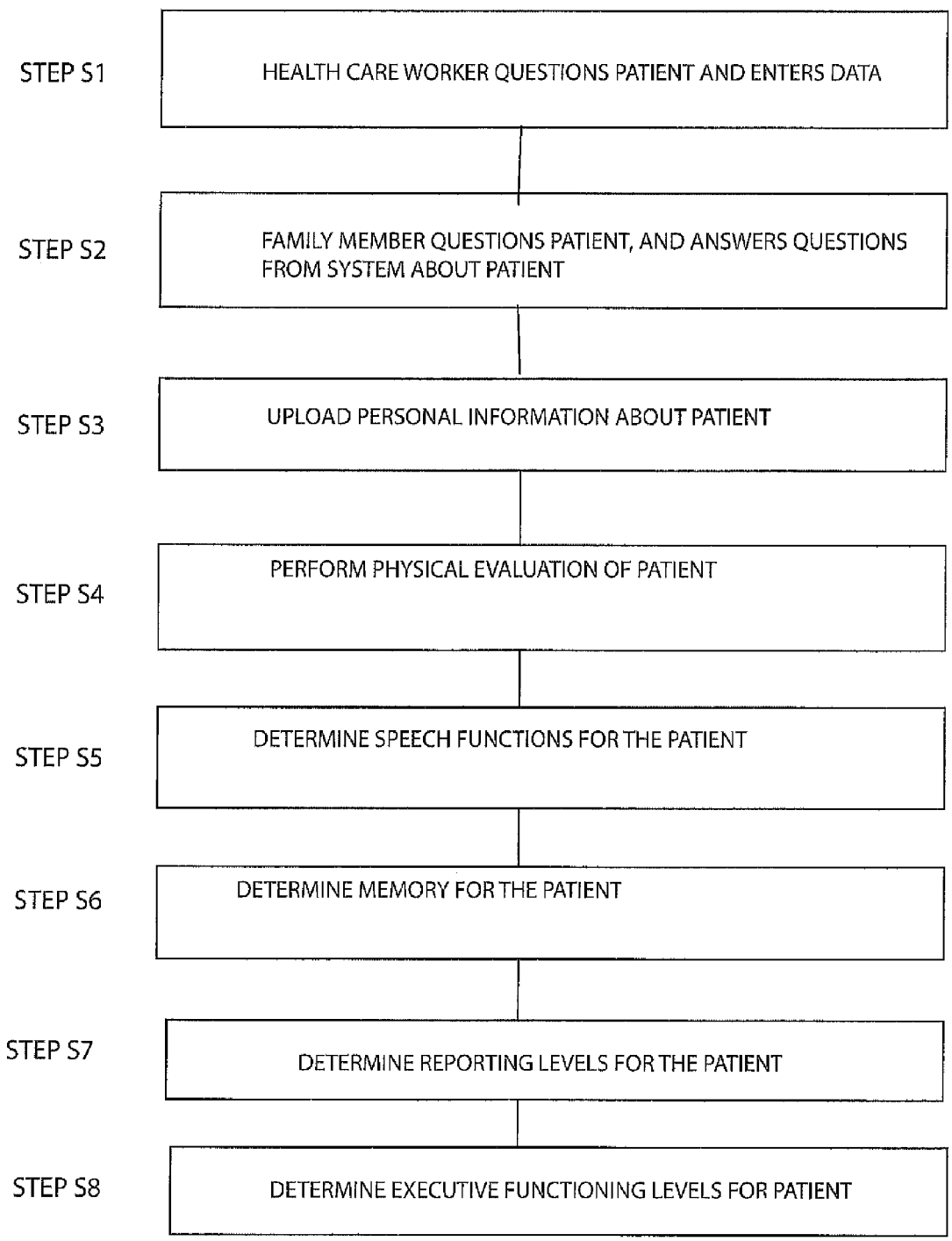
FIG. 3 is a flowchart of the process for determining a health level for a user.

FIG. 3 shows a series of steps which are used to outline the process for gathering information about a patient. For example, in step S1 a health care worker can be brought in to question a patient. The questioning of the patient can include a series of questions relating to the patient's medical history, any drug allergies, and any other critical data which can include but is not limited to demographic information, personal information including name, address, names of family members, insurance information, previous doctor information, a request for a description of any injury/trauma, or significant event. This process can include the steps shown in FIG. 5 as well as even the information shown in FIG. 6. If all of the information about the patient cannot be obtained by the health care professional then the health care professional can also question the patient's guardian or authorized representative or relative. Next, in step S2 the family member can be brought in to question the patient as well. The family member can either provide additional information to the health care professional to complete the initial takedown of information, or alternatively the family member can also provide additional questions to the patient as well. The questions and information obtained can be any suitable information such as that shown in the process of FIGS. 5 and 6. For example, in this step the family members can be questioned about the patients past and the family members can find or locate personal information about the patient including media such as photographs, songs or videos.

Next, in step S3, once at least one of the answers to questions and further information is obtained, this information about the patient can be uploaded into the system either at a single time or in successive events. At least at first, the information can be stored in memory 73, and/or mass storage 74 or in memory 123, and/or mass storage 124. If the information is first stored in local portable computer 70, such as in memory 123, it can then be communicated to application server 120 wherein this information is at least temporarily stored in memory 123. This information then optionally sent over to database server 130 and stored in database tables in this server or in mass storage in storage servers 140, 142, 144, 146.

Alternatively, if the data can be initially uploaded from a portable computer 70, or alternatively from remote computers 60, or 80, it can be alternatively uploaded directly to database server 130 and then selectively stored in any one of storage servers 140-146.

Next, in step S4, the health care professionals and the family members can perform a physical evaluation of the patient. The physical evaluation can include an evaluation of how the person walks, their balance, their motor functions, strength, alertness etc.

Next, in step S5, the health care professional working with the system, or a family member can determine the speech functions of the patient. These speech functions are explained in greater detail in FIGS. 8 and 9. For example the system can present a statement on a screen such as a portable screen for the user to repeat or say so that the health care professional or the family member can test the user's speech ability. Next, in step S6 the process can be used to determine the memory for the patient. The steps associated with determining the memory for the patient is shown in greater detail in FIG. 10. Next, in step S7 the system can be configured to determine the reporting levels, levels of communication and responsibility for the patient as outlined in FIG. 13. Next, in step S8 the system can be configured to determine the executive functioning levels for the patient as outlined in FIG. 14.

Figure 4:
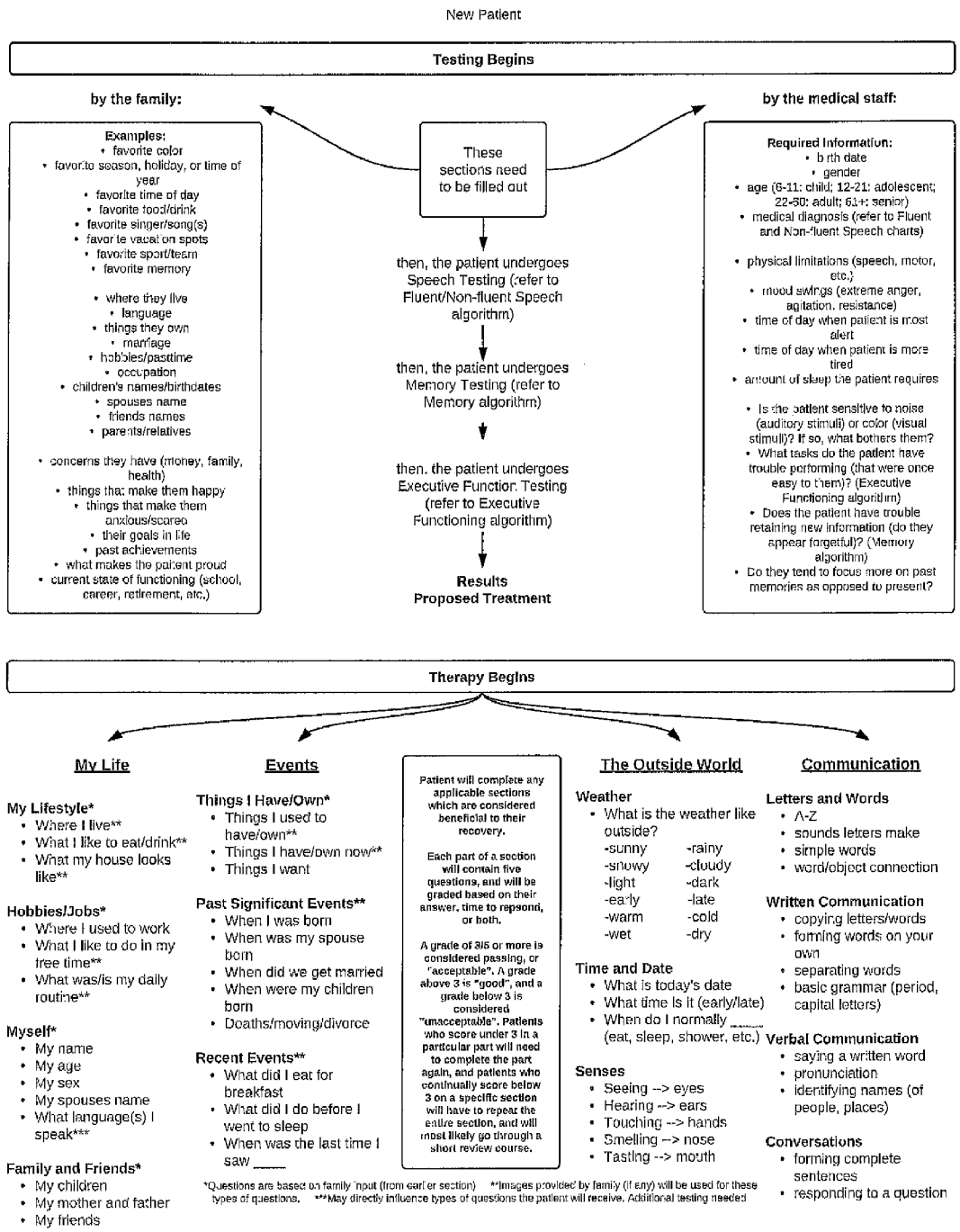
FIG. 4 is a flowchart of the process for creating a personalized treatment program for a user.

FIG. 4 shows the general flow chart for the system along with either a family member or a health care professional to determine the capabilities and to proscribe a treatment for the user. For example FIG. 4 sets forth they types of questions typically asked of the patient by the family, as well as the types of questions typically asked of the patient by the health care professional or medical staff. FIG. 4 also outlines the type of therapy that can be applied to the patient based upon the information received into the system. This general flow chart of information is explained in greater detail below.

FIG. 5 is a flow chart which is a subset of the flowchart shown in FIG. 4 and which is an alternative process to the process shown in FIG. 3. For example, FIG. 5 shows step 501 wherein the system prompts a user to determine the age of the patient. For the purpose of this process, one common way to prompt a user is for a screen to appear on a portable computing device such as a portable phone 70 or a tablet computer 80. Alternatively, the prompt can be in the form of an audio command or question. That screen/audio command could include a question pulled from memory such as memory 73, or mass storage 74 or pulled from for example database 130. These questions can be standardized questions that can be stored in database 130 and be used in many situations. For the purpose of this process, the user can be either the patient himself, a family member a health care professional, or any other suitable user, In step 502 the system prompts the user via a screen or audio to determine whether there has been a medical diagnosis. In step 503 the system prompts the user to determine whether there are any mood swings. In step 504 the system prompts the user to determine a time of day when a patient is more alert. In step 505 the system prompts a health care professional or other user to determine when a patient is more tired. In step 506, the system prompts the health care professional or other user to determine whether the patient has had enough sleep. In step 507 the system prompts the health care professional or other user to determine the physical limitations of the user, this step can coincide with step S4 wherein the user performs a physical evaluation of the patient. In step 508 the system prompts the user to determine the short term memories of the patient. In step 509 the system prompts the user to determine the long term memories of the patient. In step 510 the system prompts the health care professional or other user to determine the level of executive functioning for the patient (see FIG. 14). At each one of these stages, the system is configured so that is provides at least one or a series of questions to the health care provider or user to assist the health care provider or user in determining an evaluation as listed above. These questions could be followed by additional more pertinent questions depending on how the first round of questions proceeded. The answers to these questions can then be input into the system so that the system can then set up a profile of the patient.

Figure 6:
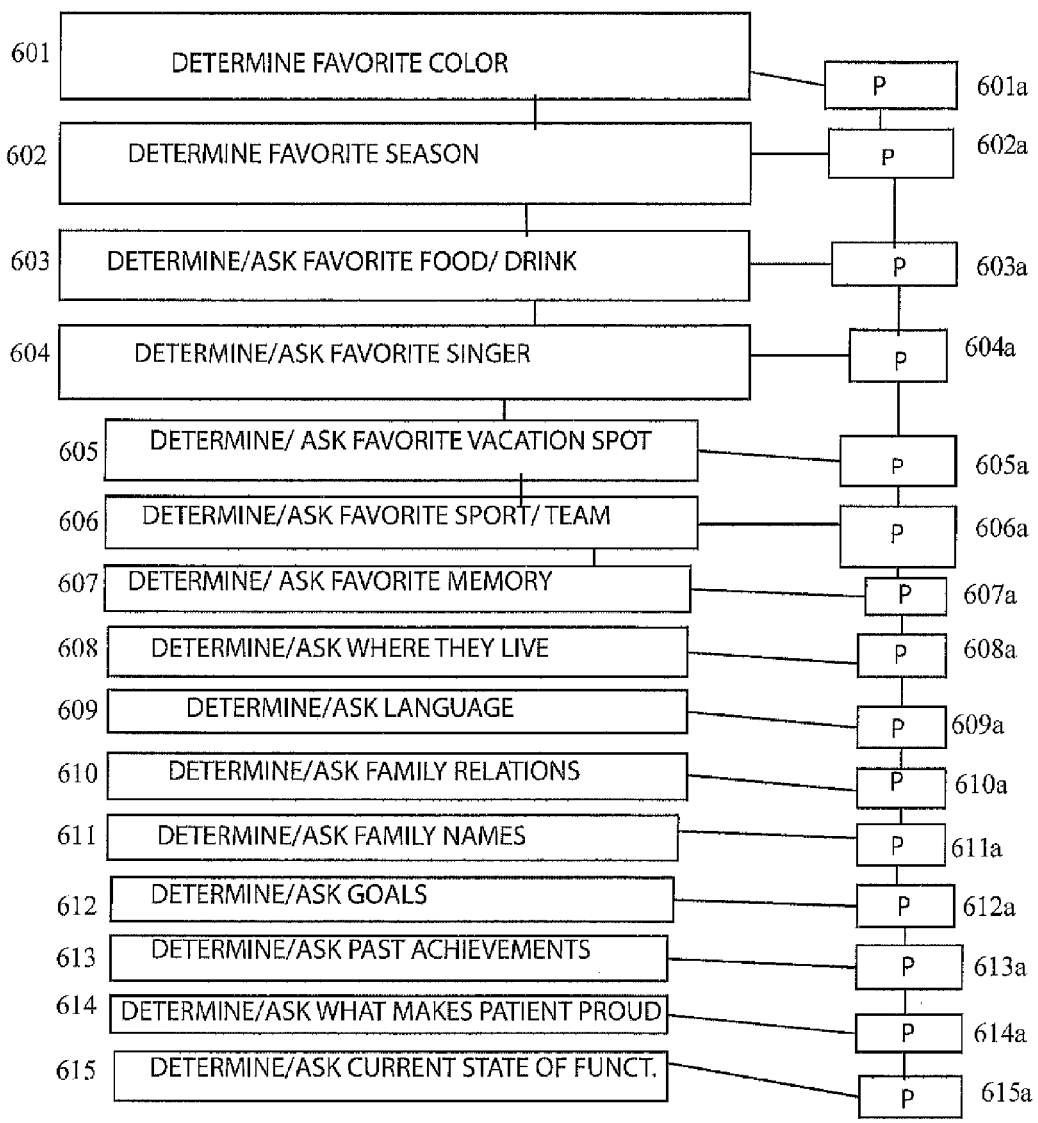
FIG. 6 is a flowchart of the process for a family member obtaining personalized information from a patient.

FIG. 6 is the process for prompting a user to proceed with gathering personal information about the patient/user. For the purposes of this procedure, the term user could be a patient, medical professional, or staff, a family memory or any other suitable user. In addition, the prompting can occur as indicated above, with either a screen showing a question or via an audio command. For example, in step 601 the system prompts the user about whether the patient has a favorite color. Once the user obtains this information, he/she inputs information about that favorite color into the system. Colors can be important because it is a base visual image that can be used to orient the patient towards a familiar soothing setting. This can include a step for prompting the user into uploading pictures that the user has. Next, in step 602 the system prompts the user about a favorite season for the patient. This can involve uploading pictures for the user in step 602a. Next, step 603 involves determining the favorite food and drink of the user. This step is associated with the sense of taste and smell which involves deep memories for the user and which can be helpful in helping the patient identify familiar smells and sounds. This step can also include an associated step 603a which involves prompting the user to upload photos, videos of the favorite food or drink of the user/patient. Next, in step 604 the system prompts the user to determine the patient's favorite singer. This can involve prompting the user to upload pictures, videos/audio recordings such as in step 604a into the system. These videos/audio recordings can include videos such as videos of the favorite singer. This can also include audio recordings of that singer as well.

Next, in step 605 the system can include determining the favorite vacation spot for the user. This can include step 605a which prompts the user to upload pictures, videos or audio recordings into the system so that these pictures, video or audio recordings can be used later to treat the patients long term memory.

Next, in step 606 the system includes the step of determining a favorite sports team for the patient, wherein the user is prompted to put into the system an identification of the favorite sports team for the user.

Next, in step 607, the system determines or asks a user about a favorite memory. This step can involve in step 607a uploading pictures, video and audio for the patient to reconstruct the memory for the patient.

Next, in step 608 the system can involve prompting the user to ask the patient about where they live. This can involve step 608a which involves prompting the user to upload the videos, and pictures for the user and to add audio for the patient as well. This step involves uploading pictures regarding the front of the yard/house, the back of the yard/house, the interior of the house as well as interior rooms of the house as well. This step can also include uploading data into the system which involves uploading data such as the address of the user including street address, town address, state, local municipality etc.

Next, in step 609 the system can prompt the user to determine/ask about a language for the patient such that in step 609a this system can include prompting the user to upload speech, or audio files, video files and/or pictures as well. The pictures can be of pictures having words of the language on the picture as well. For example if the user resided in the United States but had originally emigrated from another country, the original or primary language of the patient could then be determined. This allows the patient to reconnect with the language that they had early in life, reconnecting that patient with deep seated long term memories, that may not have been affected by an recent trauma or decline in mental functioning. Next, in step 610 the system can determine or ask the user about family relations including the names of relatives and their position in the family relative to the patient. This process can include the step of 610a wherein the user can be prompted to enter pictures of the family members as well. The introduction of family members allows the patient to reconnect with family members via a video screen so that the user/patient can begin to remember his/her old familial connections. Next, in step 611 the system can ask the user about family names of the parties as well so that these family names can be prompted in step 611a so that they can be entered into the system.

Next, in step 612 the system can determine and ask the user about the goals of the patient so that the system can determine how the person can learn to live their life. Step 612a involves inputting information about the user into the database so that the system can determine the primary goals of the user. Next, in step 613 the system can ask the user about past achievements and prompt the user to input information about the user's past achievements as well in step 613a, Next, in step 614 the system can prompt the user to input information about what makes the patient proud. This can include in step 614a uploading information about what makes the patient proud. Next, in step 615 the system can inquire with the user about the current state of functioning of the individual. This includes step 615a which includes uploading information about the user and how the user operates.

This information once uploaded and stored such as in database 130 can be used to help the user such that this information can then be used to assist a medical professional in making a diagnosis and to help the patient to train the individual and to create a learning atmosphere wherein the user would be able to interact with the patient to receive treatment. One of the benefits of using personalized information is that this personalized information can be presented to the patient based upon a time in the patient's life so that if the patient has long term memories that have been unaffected by recent trauma or by slow overall decline in mental functioning, the system can assist the medical professional in making a proper determination of the abilities of the patient as well as assisting the medical professional in proscribing a treatment.

The treatment of the patient can be in the form of a training system using any suitable type of computer such as a laptop, a desktop, a tablet computer etc.

When uploading media, such as in any one of steps 601a-615a the system can prompt the person uploading the picture to input information about the picture. For example FIG. 7A involves a process for methodically applying additional information to each picture. The picture can be stored in any one of the data servers 140, 142, 144 or 146 and the information about the picture including its identity, a key to the particular patient, and the pertinent information provided below. This pertinent information allows the system to create a series of questions about the picture or other media files so that when a medical professional looks to form a determination of the cause of the patient's symptoms or to treat a patient, particularized questions can be used about the media.

For purposes of this series of steps, the user can be a family member or medical professional or any other suitable user who obtains information from a person such as a patient or the user can be the patient himself or herself. The prompting process can include the computing device 60, 70 or 80 presenting a screen with at least one question and optionally an audio request as well. For example, this process can include step 701 which includes prompting the user about how many people are in the picture, and then in step 702 prompting the user to identify who is in the picture. Next, step 703 can prompt the user to determine how these people are related. Step 704 prompts the user to identify where the picture was taken. Next, it in step 705, the system prompts the user to identify who is the oldest/or youngest in the picture as well as whether the person or patient would see themselves in the picture. Next, in step 706 the system can question the user to see whether the person sees themselves in the picture.

FIG. 7B shows the series of steps that a user can use to categorize and provide video information. For example, step 711 involves the system questioning a user/patient how many people that user/patient sees in the video. Next, step 712 involves the system questioning the user on who the user/patient sees in the video. Next, step 713 involves the system questioning the user on whether these parties in the video are related to the patient. Next in step 715 the system can question the user/patient on who the oldest person is in the video. Next in step 716 the system can question the user/patient on who is the youngest person in the video. Next, in step 717 the system can question the user/patient on the objects viewed in the video. Next, in step 718 the system can question the user/patient on whether the user sees himself on the video or sees the patient on the video in step 718.

FIG. 7C shows steps 707-710 are a series of questions presented to the user to answer questions about another media file such as an audio file. For example, in step 707 the system can question the user about the name of the song. Next, in step 708 the system prompts the user to identify who sings the song. Next, in step 709 the system can question the user on how it makes the user feel. Next in step 710 the system can determine the decade that the song was released.

These questions presented by the system are generated by the application server via a particularized series of instructions running on the microprocessor 122. The questions generated by the system are generated by microprocessor 122 on application server 120 and are communicated to other computing devices such as any one of computing devices 60, 70, or 80. Application server can obtain these questions via database server 130, if these questions are not independently already generated by application server 120.

These questions would then appear on the screen of these computing devices or be delivered by an audio output of these computing devices. For example the question could appear as text on a screen, and/or be presented to the user via a computerized pre-recorded voice or audio command. Any other type of audio or visual cues could also be presented to the user to prompt the user to input data into these remote computing devices. These remote computing devices can include a tablet interface or a keyboard, or an audio input such as a microphone in which to process the inputs of the user. Once these inputs are put into these remote computing devices, either the file, or the input is then communicated back through the computer network such as through the internet 100 through router/firewall 110 and then into application server 120. Application server 120 then determines where to store this information. If the information is in the form of text or other similar style data, then this data is stored in database server 130. If this information is in the form of video information, audio information, or picture information then it is stored in storage servers 140, 142, 144, and 146.

Once all of the background information has been uploaded into the system, the system proceeds to instruct the user to form a determination about the medical condition of the user/patient. This determination is based upon the speech functioning, memory functioning, and executive level functioning of the user/patient.

FIG. 8 is an overview process for determining the speech functioning levels for the patient. The speech functioning examination and evaluation of a patient is shown in greater detail in FIGS. 9A and 10. For example, in step 801 the user such as a medical professional can use the system to determine whether the patient is fluent or non-fluent in speech. If the patient has fluent speech, then the patient follows the process outlined in FIG. 9A. Alternatively, if the patient has non fluent speech then the patient and user follows the process outlined in FIG. 10.

Next, the system can determine the level of comprehension of the patient in step 802. The level of comprehension is based upon a series of questions that are presented to the user either written or verbal. For example, the system can present written text on a computer screen or present an audio question to the user. Depending on the ability of the user to answer these questions, and the score, the system can determine whether the user is capable of comprehending basic questions or even more complex questions.

Next in step 803 the system can provide repetition to the user to determine whether the patient is able to repeatedly speak certain words. This repetitive testing of the user provides feedback so that in step 804, the system determines the level or ability of repetition by the patient to determine the level at which the patient is functioning at a level of speech.

Next, in step 805 the user is presented with a series of objects in which to analyze. These objects can be displayed on a computer screen such as on a remote computer 60, a phone 70, or a tablet computer 80. For example, the patient can be presented with pictures of familiar objects within the patient's home (ie. clock, a favorite chair, patient's bed, etc.) The patient is then asked to identify and name the object. This familiarity of objects may help to trigger the patient's recollection (stock images may also be used in addition to custom images). (See FIGS. 9B-9E for greater detail).

Next, in step 806 the system can be used to assist a medical professional to provide a determination that can be used to provide further effective treatment. For example, the answers to these questions are stored in database server 130 and can then be recalled by the medical professional at a later date so that the medical professional can then use this report to make a determination or to form a diagnosis.

Figure 9A:
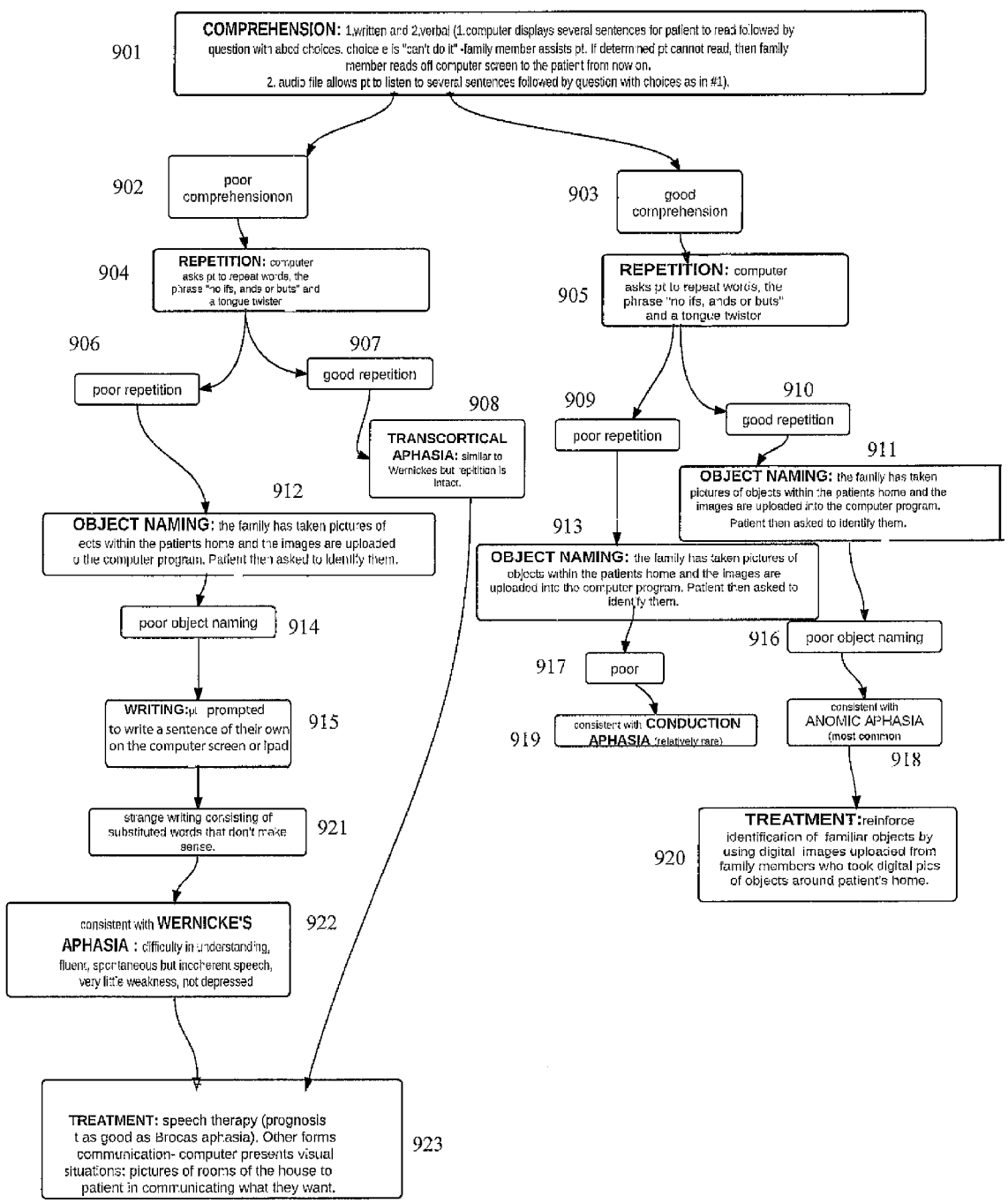
FIG. 9A is a flowchart of the process for treating a user who is capable of fluent speech.

As indicated above, if the medical professional determines that the patient is capable of fluent speech, then the medical professional evaluates the patient using particularized testing for patients capable of fluent speech. This process is shown in greater detail in FIG. 9A. Thus, FIG. 9A shows a flow chart for a more detailed process for determining the level of fluent speech in a patient using the system. For example, a user is handed a portable computer with associated software for running the process shown in FIG. 9A. This portable computer such as any one of portable computer 60, 70, 80 has a processor such as a microprocessor such as microprocessor 72 which is configured to run the process outlined in FIG. 9A. Portable computers such as a desktop, laptop, phone, or tablet computer can have a set of internal electronic components such as a microprocessor, a memory and a mass storage device all coupled to a motherboard such as shown in FIG. 2A or 2B. For purposes of the process shown in FIGS. 9A and 10, the system can be the local portable computer 60, 70, 80 running a program to perform the steps outlined in these FIGS., or the system can be the combination of the application server 120, the database server 130 and the storage server 140, 142, 144, 146, or be simply the simplified system including application server 120 shown in FIG. 1B. If any one of the local computers are running the process then a local processor such as processor 72 would be programmed to carry out the instructions indicated by the steps in FIGS. 9A and 10. Alternatively, the program could run on processor 122 or be split between processor 122 and processor 72 to run in a hybrid manner.

For example, in the first step 901 the computing system displays several sentences to the user prompting the user to read questions with a series of choices. If the patient can complete the questions, then the patient moves onto the next process. If the patient cannot complete the question, then the patient selects another type of choice such as choice "e" wherein the patient requests assistance from an assistant such as a medical professional or a family member. If the patient cannot answer the question then the family member or medical assistant reads off the computer screen and attempts to assist the patient.

Depending on the answers provided, the system proceeds to either step 902 or step 903 wherein the system can determine whether the user is capable of poor comprehension or good comprehension. For purposes of this section, any determination by the system, such as whether the patient is capable of poor comprehension or good comprehension is reviewable by a medical professional to make a final determination. In at least one embodiment, this system is configured only to provide information to a medical professional so that it eases the medical professionals tasks or job in forming a diagnosis. Ultimately any medical diagnosis using this system is formed by the medical professional.

For example, the system can proceed to step 902 to determine there is poor comprehension. This test for comprehension can occur using a series of questions about the personal life of the patient or using a series of stories to determine whether the patient can follow the stories. The determination can be in the form of testing the user to determine how many questions about the patient's personal life they can recall, how much information they can pull from a picture/audio clip/video clip or how much information they can remember or follow in a story. Depending on the grading system for the patient, the system can make a determination on whether the patient has good comprehension or poor comprehension. For example, if the patient scored 80% or higher with at least 4/5 questions being recorded as correct then the system can score this as good comprehension. If the patient scored 60% or higher, the system can either score the comprehension as moderate, good or bad depending on the customized level. If the patient scored below 60% then the system could selectively determine that the patient had poor comprehension or continue testing to make a more affirmative determination.

If there is poor comprehension, then in step 902 the system proceeds to step 904 wherein the computer or system asks the user to repeat a series of phrases. If there is good repetition of these phrases (out of 5 phrases presented, at least 3 repeated correctly=3/5) then the system proceeds to step 907 which declares good repetition. If there is "bad" repetition of these phrases (1 or 2 phrases only repeated correctly out of total of 5 phrases=1/5 or 2/5), then the system proceeds to step 906 to determine poor repetition. The system can determine whether there is "good" repetition or "bad" repetition based upon either feedback from a medical person, a family member or by receiving voice recognition into the system.

If there is good repetition then the system proceeds to step 908, wherein the system suggests to the health care professional/user that the patient may be suffering from a particular medical condition such as Transcortial Aphasia. Transcortial Aphasia is similar to Wernickes Aphasia but the repetition of the phrases is intact. If the system and/or a health professional determines that the patient has symptoms consistent with Transcortial Aphasia, then the system proceeds to treatment in step 923.

Alternatively, under poor repetition, in step 906 the system proceeds to object naming in step 912 wherein the family or user has taken pictures of objects within the patients home and wherein images are uploaded into the computer system and can be stored for example on servers 140, 142, 144, 146 etc. The patient is then asked to identify these pictures and features of these pictures. If based upon the series of answers to the questions, the system or medical professional determines that there is poor object naming in step 914, then the system proceeds to step 915 where the user is asked to write a sentence on their own computer screen or tablet. If, in step 921 the system determines that there is strange writing consisting of substituted words that don't make sense, then the system suggests a determination that the patient may have symptoms consistent with Wernickes Aphasia in step 922. Next, in step 923 the system suggests a level of treatment for the patient. This level of treatment can be in the form of a series of pictures presented to the patient which can include a series of pictures of the house, rooms of the house, or pictures of important activities (such as eating, sleeping, going shopping which would show a picture of a favorite supermarket or store, taking public transportation, etc.). The patient would then be encouraged to provide appropriate facial expressions, gestures, actions to symbolize the situation, activity, object the patient is trying to communicate.

Alternatively, if the patient is capable of good comprehension (score of 3/5 or greater) then the computer is configured to go from step 903 to step 905 for a series of repetition steps wherein the computer asks the person to repeat words back to either the user or the system. These words can be in the form of tongue twisters or other types of series of words in repetition. If the system determines that there is poor repetition such as in step 909 then the system proceeds to step 913 wherein it presents the patient with a series of pictures for the purpose of object naming. For example, if the family has uploaded pictures into the system such that they remain in the computer, then the patient is asked to identify these pictures. If the patient cannot succeed in naming the objects in the pictures, then the system proceeds to step 917 wherein the system determines that the recognition of object naming is poor. This determination is based upon the number of correct or incorrect answers that the patient provides. For example, if the patient is only able to provide correct answers for under 60% of the questions (a score of 1/5 or 2/5), then the system determines that the person's or patients recognition abilities are poor in step 917 and then proceeds to step 191 which is consistent with Conduction Aphasia. The treatment for Conduction Aphasia is via repetition training as provided herein.

Alternatively, if back in step 910 the system determines that there is good repetition, then the system proceeds to examine the patient as to whether they are capable of naming items in a picture. For example, this can involve questioning the patient and requesting that they name objects in a picture such as a personalized picture uploaded by the patients family or health care professional. If the system determines that the condition is consistent with anomie aphasia in step 918 then it suggests treatment for the patient in step 920. Anomic aphasia is generally characterized by a patient having problems recalling words. At this point, the system proceeds towards treatment in step 920 wherein the system starts to reinforce identification of familiar objects by using digital images uploaded from family members who took digital photographs of objects around the patient's home.

This treatment can include identifying letters of the alphabet wherein the system can present the user with a list of approximately five (5) questions about a particular letter or a series of letters of the alphabet. For example, the computer gives letter "a" and the patient chooses from four (4) choices of letters that look similar (c, a, e, o). The test can involve two parts, upper case and lower case. In another test, the patient can be prompted to type the letter. Next, the system provides a user with a selected letter such as the letter "b" and patient types it on the keyboard. Next, the patient is presented with a series of questions regarding word matching. The patient is asked to match similar words together. The patient can be presented with approximately five questions for each of the group of questions above so that the system can determine the abilities of the user across a series of questions.

With respect to word matching, the system asks the patient about the word and the patient chooses from 4 choices. These words can be selected from the database such as database 130. These words can be words originally entered by the family member when the initial data input is put into the system. In another level of testing the system can present the user with a series of words for the patient to copy. For example, the system presents the word and the patient types it into the system. The patient is presented with five rounds of questions and then scored on each of the answers. Next, the system presents pictures (uploaded from family) of objects (family gives 20 digital images or family picks from stock images). The patient is presented with five different rounds of questions. At each round the patient chooses from a series of different choices.

In another round (5 questions) the patient can be presented with a series of questions about a picture and instead of being provided with a series of different choices, the patient is presented with a lead in with an optional first letter for the object being presented. For example, if there is a picture of a cat, then the picture could have a list of letters for which to identify the cat such as a, e, I, o, y and c. Alternatively, the patient could be provided with two letters such as CA or all three letters CAT to assist the user in identifying the object in the picture. If the patient selects the correct letter then the answer is scored as correct. Next, the system presents the patient with a series of questions regarding phrase completion (chosen by family member or they could choose from stock phrases). Five questions are asked of the patient and then the patient is scored on the answer of these five questions. In this level of examination, the patient is given a choice of words to complete the phrase.

In another level of examination, the system presents the patient with a series of sentences for sentence completion. These sentences are uploaded originally by the family member into database 130. The system then pulls or draws from this database to determine the level of stock sentences. For example, the patient is given a series of different choices. After five rounds of questions, the system determines the level of ability of the user.

Figure 9B:
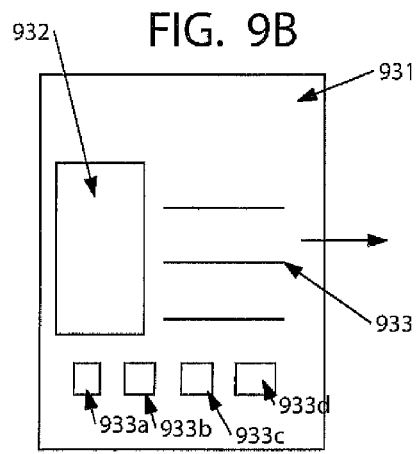
FIG. 9B is a first screen shot of pictures with questions and answers that can be presented to a user.
Figure 9C:
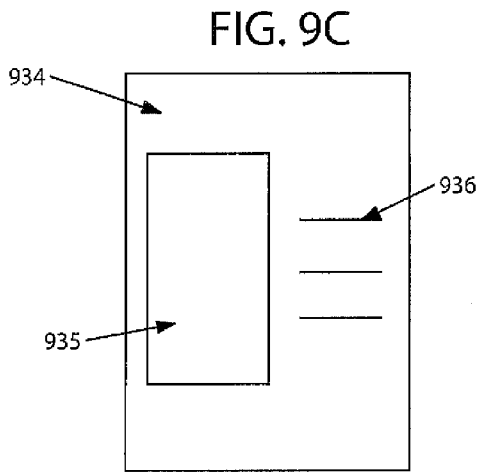
FIG. 9C is a screen shot of pictures with questions and answers that can be presented to a user.
Figure 9D:
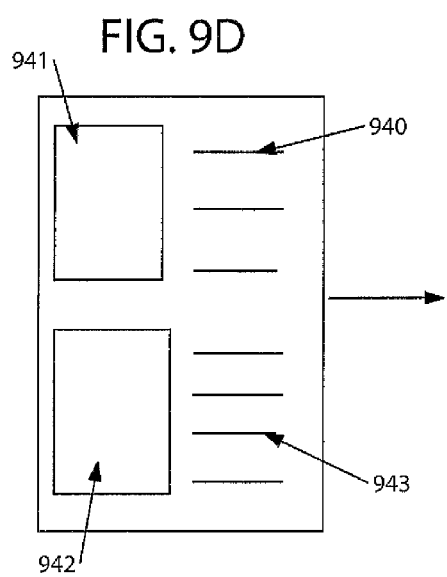
FIG. 9D is a screen shot of pictures with questions and answers that can be presented to a user.
Figure 9E:
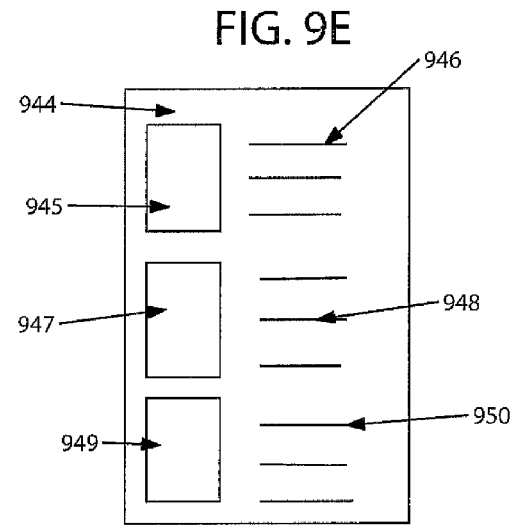
FIG. 9E is a screen shot of pictures with questions and answers that can be presented to a user.

Throughout the process of determining the mental functioning of the user, the system can present a series of questions to the user to assist a medical professional in making the determination of the level of functioning of the user. These questions can be shown by way of example, in FIGS. 9B-9E, For example, FIG. 9B shows a screen shot of a familiar picture as it would be presented to a user. Thus, there is a screen 931 which includes a picture 932 and a series of statements or questions about the picture in section 933. The patient is then prompted to answer at least one question about the enclosed picture 932. Then, the patient can then select one of the options for answers such as 933a, 933b, 933c and 933d.

Once the patient has selected one of these options then the system can determine whether the answer is correct. Once that question has been answered, the system can proceed forward to question the patient on another screen 934 including another picture 935 as well as another set of statements 936. Once the patient has answered the appropriate question about this screen, then the system can proceed forward to FIG. 9D wherein the system can present another screen 940 wherein another set of pictures 941 and 942 are presented along with another set of statements 940 and 943. Next, in step 9E the system can proceed to screen 944 wherein the system proceeds to question the user about three different pictures such as pictures 945, 947 and 949 which have a series of associated statements or questions in sections 946, 948 and 950 associated with them.

Figure 10:
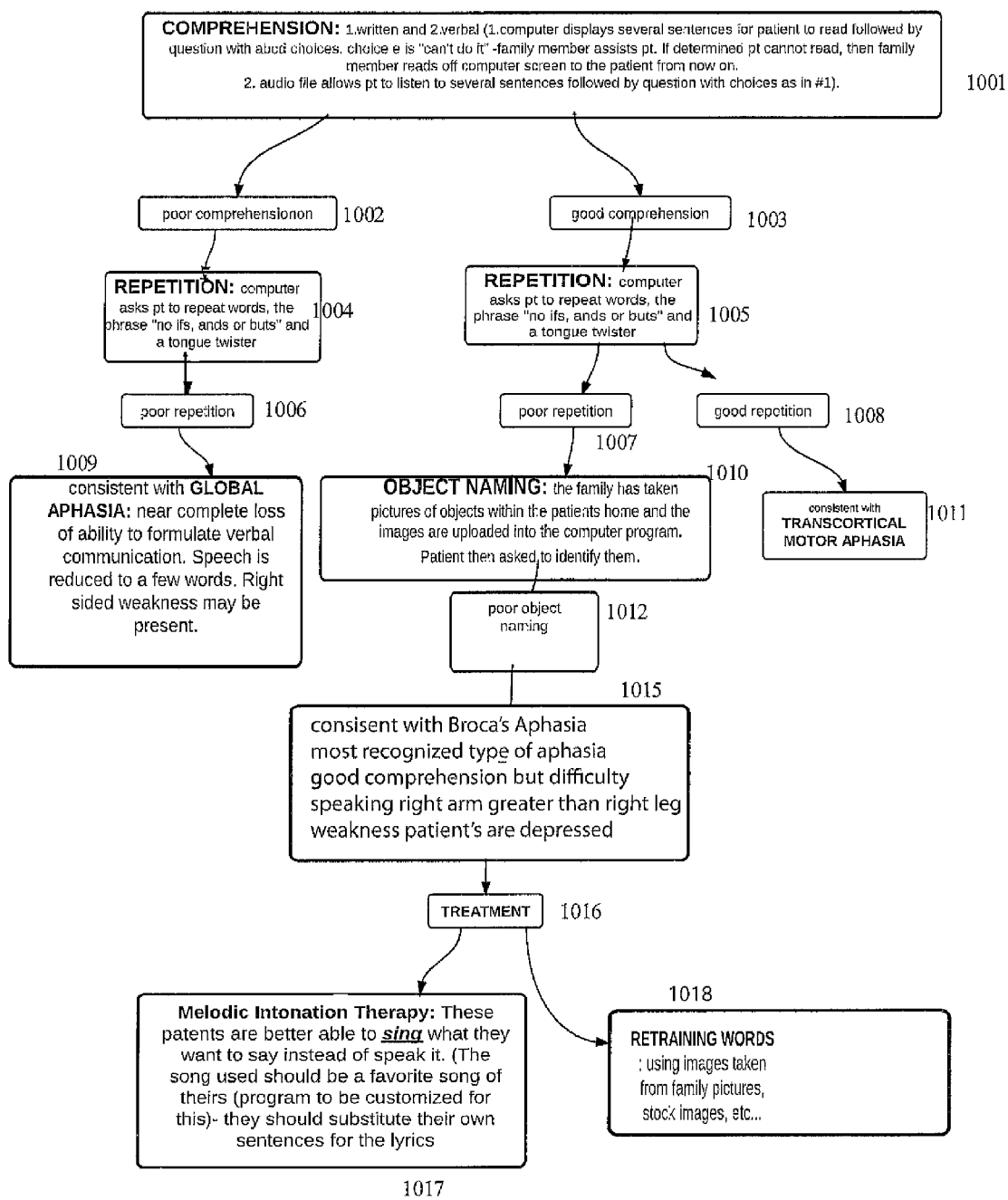
FIG. 10 is a flowchart of the process for treating non-fluent speech.

Alternatively, if the system or the system in combination with a medical professional determines that the patient is not capable of fluent speech, then the system proceeds to the process outlined in FIG. 10. For example, in this process there is step 1001 which includes the system providing written and verbal testing of the patient so that the patient is prompted via a video screen or audio prompt to read a series of statements on the computer screen. The patient is then presented with a series of questions regarding the plurality of pictures shown in FIGS. 9B-9E. Next, depending on the answers to the questions, the system determines whether the patient is capable of poor comprehension or good comprehension. Poor comprehension in step 1002 is determined by the system if the patient cannot answer correctly at least 60 percent of the questions. Conversely, good comprehension is determined if the patient can answer at least 60 percent of the questions correctly. If there is poor comprehension as determined for example, in step 1002, then the system prompts the patient to repeat words such as the phrase "no ifs ands or buts" and then to recite a series of tongue twisters as well in step 1004. If the patient cannot master or at least pass the repeating phase, then the system determines that there is poor repetition such as in step 1006. If the system determines that there is poor repetition then it suggests to the health care professional or the family member that the patient may be suffering from global aphasia in step 1009.

Alternatively, if the system/health care professional determines that the patient is capable of good comprehension in step 1003, then the system proceeds to prompt the user to provide repetition of speaking words. This step of repetition 1005 is similar to the step of repetition in step 1004 where the patient is prompted to repeat the phrase "no ifs ands or buts" and then to speak a tongue twister.

The determination of vocal repetition can be provided by the health care professional or alternatively by the system using a microphone and voice recognition software. In the embodiment where the system has a microphone and voice recognition software, the system can then automatically score the ability of the patient to engage in vocal/speech repetition. If the patient provides poor repetition in step 1007 then the system proceeds to step 1010 to provide object naming. If the patient provides good repetition, then the system determines that the patient may be suffering from Transcortial Aphasia in step 1011.

In step 1010, the patient is presented with a series of drawings for the purpose of object naming. These drawings can be in the form of a plurality of different images such as with the images shown in FIGS. 9B-9D. If the patient cannot answer the questions to a sufficient level such as answer at least 60% of the questions correctly, then the system determines that there is poor object naming in step 1012 then the patient's symptoms are consistent with Brocas Aphasia which is one of the most recognized types of Aphasia which includes good comprehension but difficulty in speaking. In step 1016 the system then suggests treatment for the user. This treatment can be in the form of melodic intonation therapy in step 1017 or through retraining words in step 1018. Melodic intonation therapy involves prompting the patient to sing rather than to speak. The song should be a favorable song or favorite song of the user.

For example, under melodic intonation therapy, the system presents the patient with an instrumental (live version or cover version) version of patient's favorite song (or song is chosen from list) presented by the system. The system gives the patient several bars of the chorus and a family member hums along while the patient taps out the rhythm with hands or feet. The system then grades the user on the rhythm. This grading can be done either automatically by the patient tapping on an input or a screen, or an assistant inputting the information into the system. On a score of 1-5 for the five questions, the patient is graded on their rhythmic ability. For example, the patient can be graded as follows: (graded 1-2=out of rhythm, 3=fair but out of rhythm at times, 4-5=good rhythm.)

Next, the patient hums while tapping out the rhythm. This tapping can be into the input panel/button of the device. The patient can then be graded on a scale of 1-5 for the answers to five separate questions. For example, the following scores can be provided: 1-2=humming and rhythm not in sync, 3=fair, and 4-5 is good.

In another test, a family member hums the two syllable word, phrase or sentence that the patient is to say to the tune of the song, (the chorus part of the song) and the patient sings repeats it. The system can then provide a score to the patient as well. This score can be graded as follows: 1-2=poor, 3=fair, 4-5 well done).

In another test, the patient is presented with a word. The patient waits a period of time (6 seconds) then repeats the word, phrase or sentence. After approximately five (5) rounds the patient is graded on his/her answers.

Next, the word, phrase or sentence is repeated without the aid of the tune and gradually the patient is able to speak it (losing the melody but the words remain)(same grading system, this stage may need further repetition before scoring well on it). The goal of the patient is for the patient to speak words, phrases or sentences without an accompanying melody.

Next, the patient is presented with a series of questions regarding object naming. This type of treatment is similar to that above regarding Anomie Aphasia.

Next, the patient is presented with a series of words for repetition training. The patient is then presented with a series of five questions and then graded on this as well. With repetition training, the computer presents words (from a list of stock words and any additional words family chooses) in an audio file. In this case the patient repeats the word. In this case the patient is presented with a series of questions such as five questions and is then graded on a scale of 1-5 depending on their ability to answer the questions. For example, the user is graded as follows: graded 1-2=poor, 3=fair, 4-5=good. If the patient does poorly, then the system proceeds to the next step as outlined below.

If the person scores poorly, the system presents words in an audio file along with image to help patient. Five rounds of questions are presented to the user and the system then provides the same grading system. The grading system is then provided as outlined above.

Figure 11:
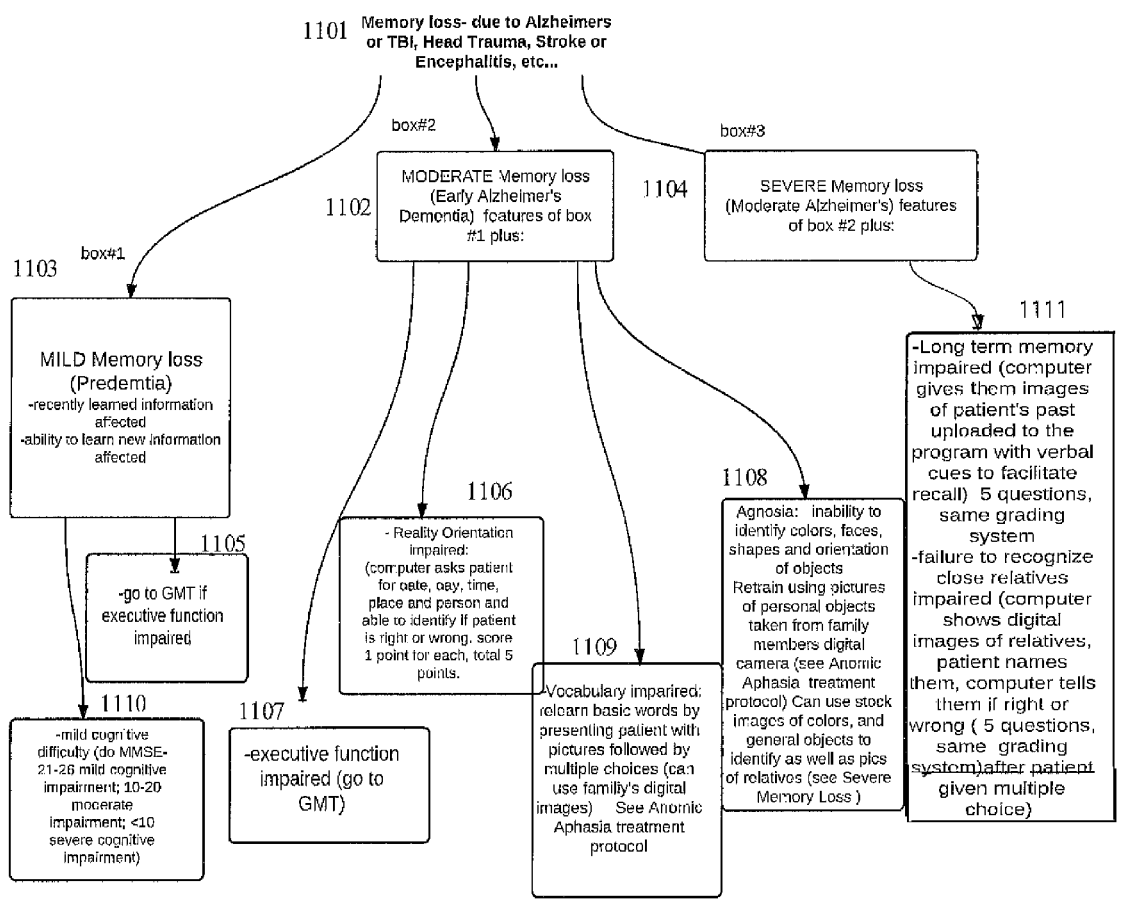
FIG. 11 is a flowchart of the process for the process for determining memory loss of a patient.

FIG. 11 shows the testing process for a patient to determine how much memory the patient lost after a head trauma, stroke or due to Alzheimer or other condition. For example, the system can present the user with a series of questions such as regarding the personal information of the user. The presentation of these questions can be in the form of questions about personal information such as shown in FIGS. 9B-9E. For purposes of this process the terms "system" and "user" are the same as the term defined above for the steps outlined in FIGS. 9A and 10.

After questioning the patient/user regarding a series of questions regarding their personal information, the system can then determine that the patient is either suffering from mild memory loss in step 1103, moderate memory loss in step 1102 or severe memory loss in step 1104. Mild memory loss is usually attributed to pre-dementia wherein the patient is then prompted to go into Goal Management Training if their executive functioning is impaired. Alternatively, in step 1110 the system can present the user with a series of standard questions such that an evaluation takes place, wherein the system determines after 30 questions (Mini Mental Status Exam or MMSE) whether there is mild cognitive impairment if the patient can only answer 21-26 questions correctly, or alternatively if the patient can only answer 10-20 questions correctly then the system determines that there is moderate impairment, or alternatively if there is less than 10 questions that are answered correctly, then the system determines that there is severe cognitive impairment for the patient. The above level of correct answers for forming a determination can be changed however, so that in at least one other embodiment, for example, a score of 50% or higher could mean low impairment for example.

Alternatively, if the system initially determines that there is moderate memory loss which is characteristic of early Alzheimer's dementia, then the system tests the patient to determine whether the patient has retained recently learned information, and whether they have the ability to learn new information. For example, the system can proceed to step 1106 wherein the system determines whether the patient is reality orientation impaired wherein the system asks the patient for the date, day, time, place and person and determine or identify whether the patient is right or wrong. A score of 1 point for each of the five (5) questions for a total of five points.

In addition, the system will also test the patient for their level of executive functioning in step 1107. This testing and treatment for executive functioning is outlined in greater detail in FIG. 14. In addition, if the system determines that there is moderate memory impairment, then the system proceeds to step 1109 wherein the system tests the patient regarding vocabulary impairment. For example, in this step, the patient is presented with a series of basic words. This type of testing can include presenting the patient with a series of familiar pictures followed by a series of multiple choices such as with the Anomic Aphasia protocol. The system would also prompt the user to identify a plurality of different colors in a series of questions regarding the colors presented as well as shapes, faces, or other familiar objects. The system can use stock images of colors and general objects for the patient to identify as well as pictures of relatives.

Alternatively, if the system determines that there has been severe memory loss, then the system proceeds to step 1111 where the system determines that the patient is suffering from long term memory loss and that their memory has been impaired.

In this case, the computer or system gives the patient images from the past uploaded into the system such that the user is presented with a series of questions relating to these pictures. (See or example, FIGS. 9B-9E) Thus the patient is given family members pictures and is questioned on their names, ages, relationship to the patient etc. The patient is given for example five (5) questions and is then prompted to answer these questions. Grading of these questions is such that if the patient answers 4/5 or 5/5 correctly then the system determines that patient has a "good grade" (score=4) or "excellent grade" (score=5). If the patient can only answer 3/5 questions then the system can determine that the patient has a "fair score". Alternatively, if the patient scores 1 or 2 then he has a "poor" grade.

At the completion of testing, the average of all the scores is taken and a number between 1-5 is given along with its interpretation; (i.e a score of 1,2=poor, 3=average, 4=good, 5=excellent overall functioning).

Once a determination of the patient has been made by the system, the treatment process can proceed with the approval of the appropriate medical professional.

During diagnosis, treatment and general care, the patient may be mentally impaired and need assistance. In addition, the information provided by the patient into the system should remain secured. Therefore, the system is configured to control the level and flow of the different types of information about the patient so that the patient's information remains secure. Thus, only those parties who are legally allowed to review this information have access to it, therefore, the system can assist medical professionals and family members in treating this individual.

FIG. 12 shows the reporting hierarchy for the system for a plurality of different professionals and family members associated with the patient. For example, regarding medical care, the physician/neurologist 1201 could be entered into the system and be given authorization to determine the cognitive abilities of the patient and determine the neurologic diagnosis. A primary care physician could be entered into the system and then be assigned the task of providing a diagnosis of the patient's overall health and well-being and be assigned the responsibility for monitoring the patient's overall health and well-being. In addition, a rehabilitation therapist 1202 could be entered into the system and be assigned the task of working directly with the patient to receive reports from the primary family member about the patients' progress. A social worker 1203 could be entered into the system and be assigned the task of being a case manager wherein the social worker would deal with the day to day tasks such as phone calls from family members and calls from patients themselves, and train the patients to use the mobile application. In addition, a home health agency 1207 could be entered into the system wherein this home health agency could be assigned the task of reporting the progress to patient's and family and to the patient's neurologist. The system can also be configured to enter in a home health aide 1206 wherein this home health aide is tasked assisting the patient with daily activities and training the patient to use the mobile application and report the progress to the primary care physician or the primary person under the family. By being enrolled or entered in the system, a particularized set of contacts are created for each patient so that if the patient needs immediate assistance, the system can be used to contact these parties.

Next, the primary family member 1205a is entered into the system. This person is designated as the primary contact for the patient. This person functions as the health care proxy and is responsible for making decisions in accordance with what the patient would have wanted. This family member has access to all of the patients' records. The primary family member has access to a web interface for the desktop version and mobile application which generates a written progress report to the primary family member on the progress of the patient. A power of attorney 1205b can also be designated. This person could be the same person as the health care proxy 1205a or a different family member.

In addition, there are additional family members that can be entered into the system as well. For example, there is a first secondary family member 1208 entered into the system. Next, there is another secondary family member 1209, any additional family member 1210. These secondary members can be entered into the system so that if the primary family member cannot be contacted, the secondary members can be contacted in case of either an emergency or in the case of one of the health care professionals needing assistance with questions or answers. This is all governed by an answering service which receives the emergency call and dispatches it to the assigned family member. It should be noted that any life-threatening emergency calls are handled by dialing 911.

Once all of the responsibilities have been assigned to all of the parties, this allows for the system to contact any one of the appropriate parties during the training and assistance phase of helping the patient.

For example, if after the patient has received ongoing training and either a health care practitioner or a family member determines that the patient can live under his or her own supervision, then the system can conduct ongoing executive level training and assistance to the patient so that the patient can live on his/her own while being assisted by a computer, or portable computing device.

Figure 14A:
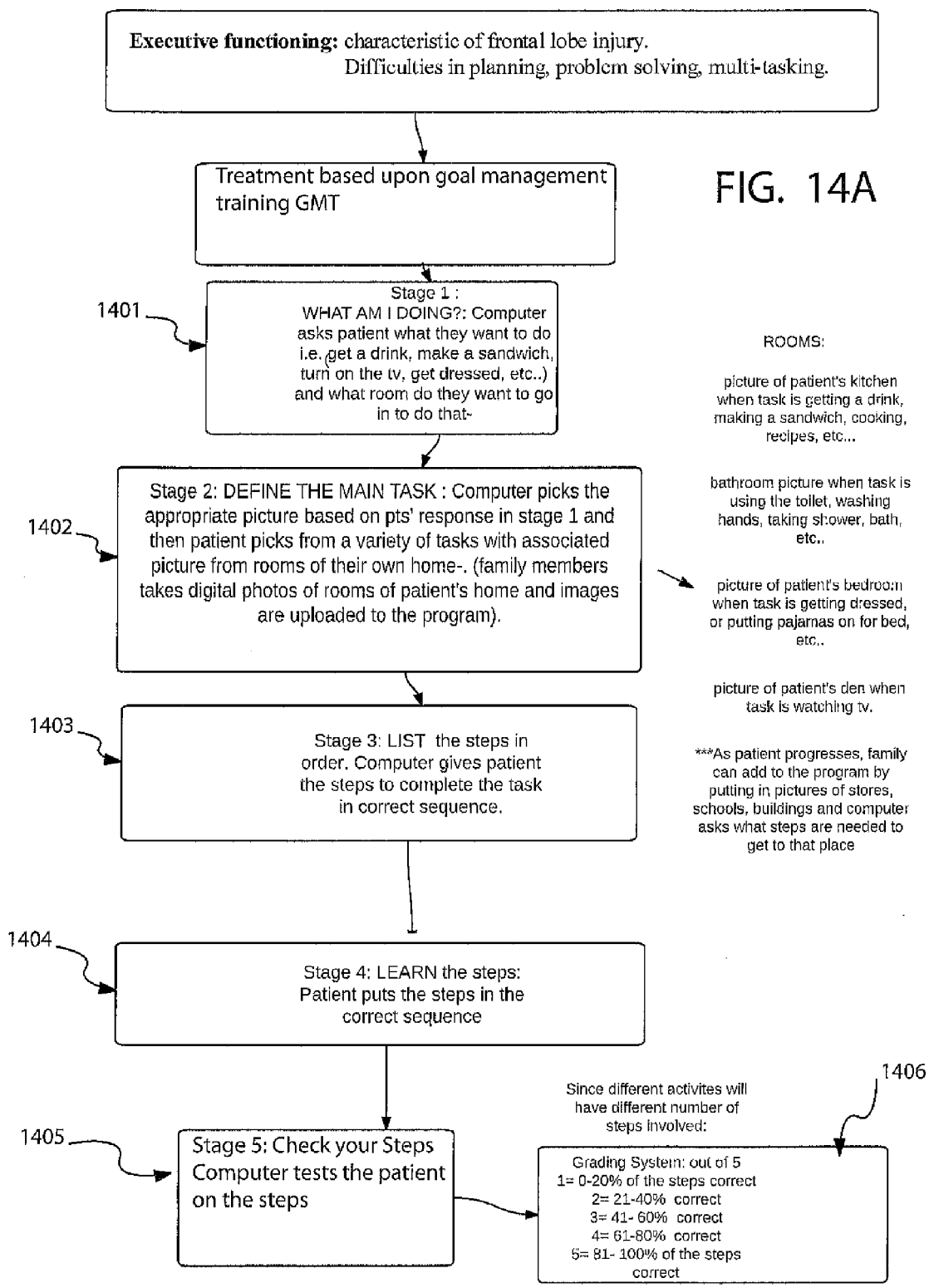
FIG. 14A is a flowchart of the process for providing guidance to a user on a particular task relating to executive functioning and for testing for ability under executive functioning.

FIG. 14A shows the process for determining the executive level functioning for each patient and for assisting a patient in conducting their day to day tasks. This process starts with providing the user with a question about their main task in step 1401. For example, the computer asks the patient "What am I doing?". The system can prompt the patient on what they want such as to get a drink, make a sandwich, turn on the television (TV). Next, in step 1402, the system helps the user to define the main task. For example, the system can choose the appropriate picture based upon the patient's response in stage 1 and then the patient chooses from a variety of tasks with the associated picture from rooms of their own home. This includes family members taking digital photos of rooms of a patient's home, wherein images are uploaded to the program. Next, in step 1403, the system such as the application server 120 running a program or the remote device 60, 70, or 80 running an installed program can list the appropriate steps in order taken from a list of pre-defined tasks stored in the database 130.

Next, in step 1404, in stage 4, the system can determine whether the patient can follow the correct order, list, and sequence of the steps. Next, in step 1405, the system can test the patient to determine whether the patient is capable of performing day to day tasks. Some of these day to day tasks can be getting dressed, brushing teeth, making a meal, cleaning the house. If the patient can correctly designate the order/sequence for the steps and knows which steps are associated with a particular task, then the system can determine that the patient is capable of a certain level or competency of executive functioning.

Step 1406 results in the system providing a grade to the patient to grade the patient to determine whether the patient is capable of functioning on their own and the level of functioning for the patient. The system can list on a display the tasks or steps necessary to accomplish the main task. Depending on the ability and answers by the patient for a series of executive level tasks the system can suggest to a medical professional or a family member whether that person is available to lightly supervised outpatient care. If the patient qualifies for lightly supervised outpatient care, then the system is configured to provide a series of help screens and electronic aides to a patient to assist the patient in completing tasks on their own. Thus, the system can create a downloadable application which can be downloadable to a portable device which can then be used to assist a user in completing their tasks.

Figure 14B:
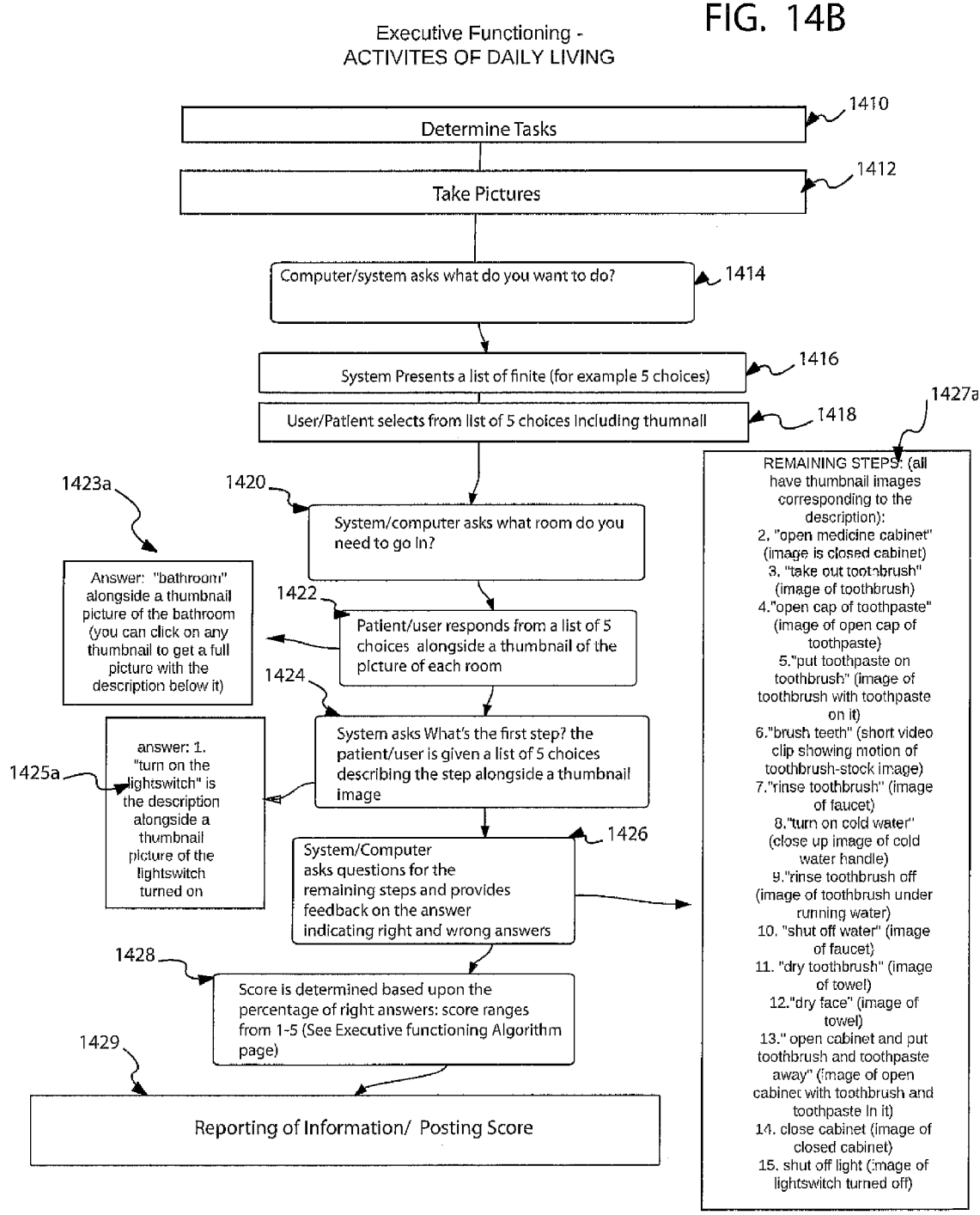
FIG. 14B is a flow chart for creating a first task.

FIG. 14B is a flow chart for creating a first task. FIG. 14C is a flow chart for a process for creating a second task. The process for each of these tasks are similar. The process includes step 1410 wherein users/patients/family members or medical professionals can determine what tasks are necessary for the user/patient to perform independently. These different types of tasks can include but are not limited to brushing your teeth, making a sandwich, putting your clothes on, etc. The users/family members/medical professionals start with the most basic and simplest but most important tasks that the patient needs help with. As the patient masters these tasks, the family member or medical professional can then update the program adding more pictures that are needed. The system can instruct the user on the types of pictures necessary for each task.

Thus, in step 1412 the user takes pictures which may be instructive for these tasks.

An example of the pictures in the process of FIG. 14B could include the following pictures: 1) a hand turning the light switch on; 2) medicine cabinet opened; 3) medicine cabinet closed; 4) toothpaste inside the cabinet; 5) toothbrush; 6) faucet; 7) cold knob of faucet; 8) toothpaste with cap off; 9) toothpaste on toothbrush; 10) toothpaste with cap on; 11) toothbrush under running water (rinsing off toothpaste); 12) towel; 13) lightswitch turned off.

For example with the process as shown in FIG. 14C, the process of "making a sandwich this includes taking the following pictures: 1) of the kitchen with the lights turned on; 2) a cabinet closed, 3) a cabinet opened; 4) a loaf of bread; 5) two slices of bread; 6) a refrigerator; 7) cold cuts in the refrigerator; 8) slices of cold cuts; 9) cold cuts on the bread; 10) mayonnaise in the refrigerator; 11) kitchen drawer; 12) knife in the drawer; 13) open lid of mayonnaise; 14) knife in the mayonnaise; 15) competed sandwich; 16) light switch turned off.

Next, in step 1414 the system prompts the user to select a task and in step 1416 presents the user/patient with a list of finite choices for tasks. Next, in step 1418, the user/patient selects from a finite list of choices such as five (5) choices. Next, in step 1420 the system prompts the user where they need to go or move to such as which room they need to go in. Next, in step 1422 the patient/user responds from a list of finite (such as five (5) choices alongside a thumbnail picture of the location such as the room. In the process shown in FIG. 14B the answer can be the bathroom (see step 1423*a*), in the process shown in FIG. 14C the answer can be the kitchen alongside a thumbnail picture of the kitchen (see step 1423*b*). Next, in step 1424 the system asks" what's the first step? At this point, the patient/user is given a list of finite choices such as five choices. In the process shown in FIG. 14B the answer can be turn on light switch in step 1425*a* or in the process shown in FIG. 14C the answer can also be "turn on a light switch in step 1425*b*. Next in step 1426 the system asks user/patient the remaining questions/steps of instructions. These different steps of instruction are shown in step 1427*a* in FIG. 14B or step 1427*b* in FIG. 14C. Next, depending on how the user followed the instructions, and whether they could identify these instructions, the system in step 1428 determines the score for the user based upon the number of right answers. The score can range from 1-5 as indicated in FIG. 14A. Next, in step 1429 the system can post or report the information on the process or task as well as the score. The score can be stored in a database such as in a database in database server 130. This information including a listing of the right and wrong answers can be sent to a medical professional such as a neurologist or a rehabilitation therapist who is working with the user/patient. This information would be useful to the medical professional to gauge how the patient is progressing. Family members may also be given this information to help determine whether they want to continue with the system/program and whether they should update the program with additional information, additional steps or additional tasks. Based upon the type of scoring, the neurologist can use this information to make a decision. For example, with a score of 1-2 the patient may need an appointment for further evaluation; a score of 3 the patient needs further work with the program to learn these steps to reinforce what is learned. A score of 4 the patient can be ready for the application of steps using a mobile application on a mobile device using this device for outpatient therapy and assistance. A score of 5 would be indicative that the patient is capable of living on his/her own and can have optional outpatient assistance.

While these two tasks have been described, additional tasks can be created and implemented as well. These tasks can be used on a general purpose computer that can be substantially stationary such as a PC or personal computer or used on a portable computing device such as a smartphone or tablet computer such as those shown in FIG. 1A.

Figure 15:
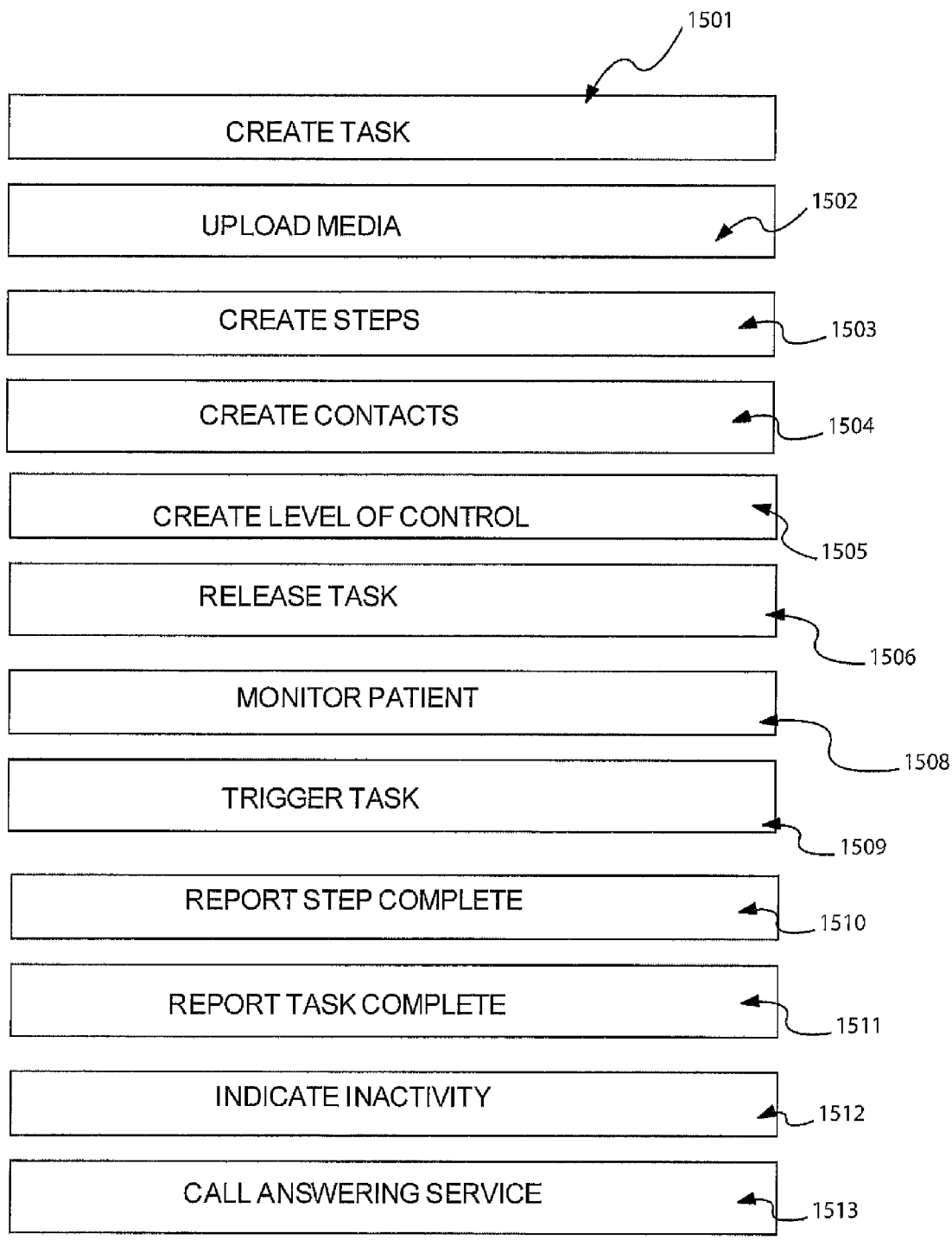
FIG. 15 is a flow chart of the process for setting up a task for a user on a portable computing device.

FIG. 15 is a flow chart for the process for creating and implementing a task that can then be downloaded to a portable device. For example, step 1501 includes creating a task. That task can be any one of but is not limited to: 1) getting dressed; 2) going to a store; 3) making a sandwich; or any other suitable task. Examples of these types of tasks are described above. Once this task has been created, this information is uploaded and a new task category is created in database server 130. Next, the family member can upload media for the task in step 1502. This media can be in the form of pictures, videos or audio information. Next, the system can prompt the family member to create steps such as in step 1503. In this system, every task would have at least one step or a series of steps. For example, getting dressed would involve at least the steps of: finding clothes, picking the clothes out and then putting them on.

Figure 16A:
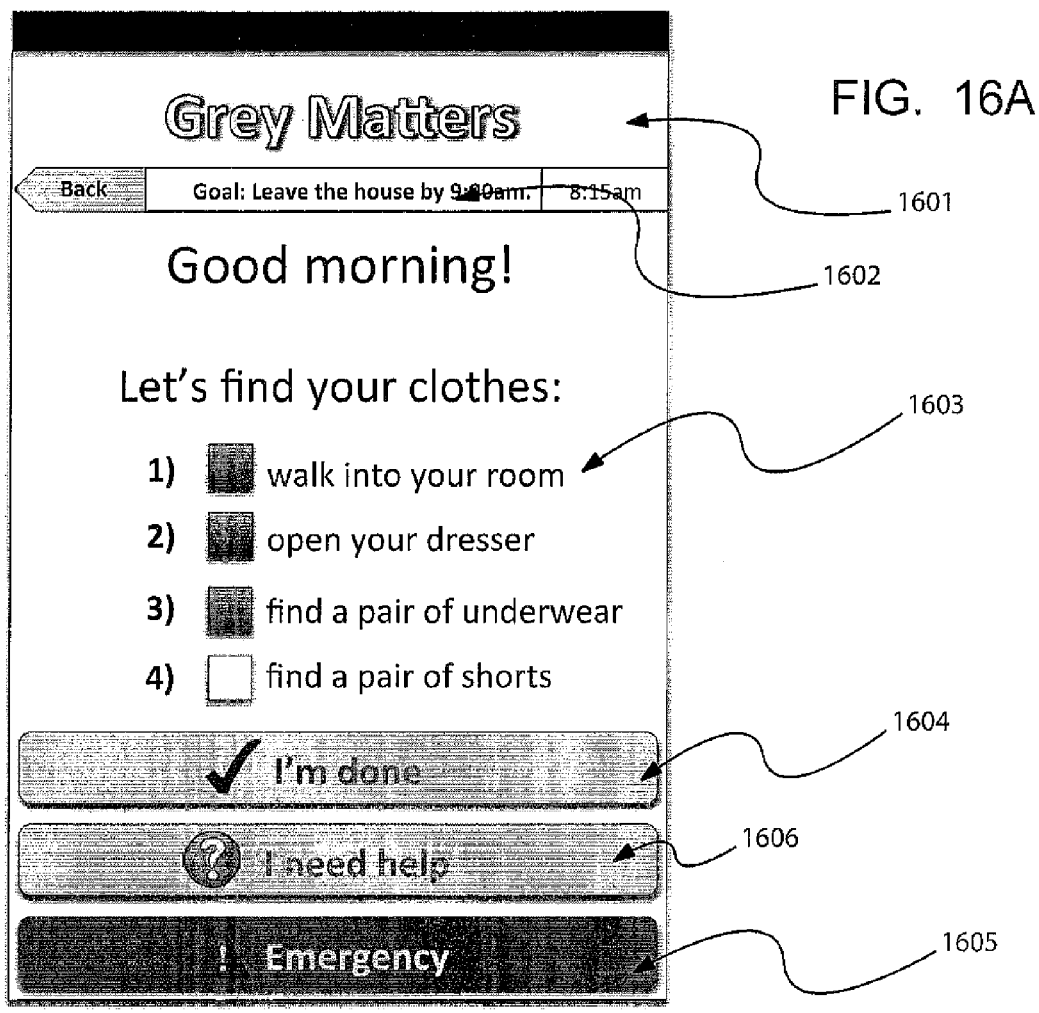
FIG. 16A is a screen shot of a portable program for assisting a patient in executive functioning tasks.

Thus, this step can include creating a series of different steps for a task such as that shown in FIG. 16A which includes 1) walking into a room; 2) opening a dresser; 3) finding a pair of underwear; 4) finding a pair of shorts. As shown in FIG. 16A this screen also allows the patient to indicate that they have completed each step via a check box, as well as indicate that they have completed a task as well. In addition, there are also buttons to allow the user to indicate that they need help or additional assistance in information as well as indicating that they are in an emergency.

Next, in step 1504 the user can create contacts for the patient so that if the patient gets into trouble or needs assistance, the user can directly contact a party set up in the contacts list. This contacts list can be governed by the hierarchy set forth in FIGS. 12 and 13. This list of people can include but are not limited to: the physician/neurologist 1201; a primary care physician 1204; a rehabilitation therapist 1202; a home health agency 1207; a social worker 1203, and a case manager 1203. Other parties on the contact list can include a health care proxy 1205*a*, a person who has power of attorney 1205*b*; a family member 1208, another sub family member 1209, or a third type of family member 1210 (See FIG. 12). One of the parties listed above can create the level of control over the information provided to and from the patient. This level of control can be based upon the hierarchy listed in FIG. 12 of the contact people. For example, the physicians could have access to full medical information as well as the health care proxy. In addition, the power of attorney could have access to any non-medical information about the patient such as financial information or other types of information. Furthermore, if the patient is in an emergency, this hierarchy list could also be used to contact the responsible parties in the event of an emergency. Once these steps have been completed, the system can release the task to the patient. For example, this task could be released to a portable computing device such as a mobile telephone, a laptop or a desktop computer.

Depending on the level of control and the level of privacy settings, some of the parties could monitor the patient and remotely assign tasks to the patient and monitor whether that patient is completing these tasks.

For example, the user could export a task to a patient's portable device based upon a timer setting or based upon a push activation. This push could be generated by an input of a remote user into a computing device presenting a command to application server 120 to schedule a task.

The user who has control over the monitoring of the task and who has pushed these tasks to the patient either manually or automatically based upon a timer, can then monitor whether each step of each task has been completed and can be notified when the suggested task has been completed. Based upon this monitoring, the user can then trigger an additional task in step 1508 as well. The user can be provided with an indication of whether the step has been completed in step 1509 and whether the entire task has been completed in step 1510. This indication can be in the form of a push notification, an email, a text message, or any other form of suitable communication.

Step 1511 includes an indication to a user or any other party monitoring a patient that the task has been completed. Step 1512 involves providing an indication to a user monitoring a patient such as a physician or other party associated with monitoring the patient to report on any inactivity with the monitoring device.

Thus, the mobile computing device such as a phone 70 can operate as a monitoring device which can be equipped with a gyroscope, a GPS and other mechanism which is configured to indicate whether the device has been moved in location, rotated, elevated and any other movement. If there is no indication of movement, then the system which includes application server 120 which is monitoring the remote computing device, can notify the user who is monitoring the patient of this inactivity.

In addition, if the patient who is being monitored or the user who is monitoring the patient is in trouble, a panic button can be activated directly from the device. The device can place a call directly to law enforcement personnel or directly to medical personnel as well as any family member designated as being in charge. In all, this system creates a complete monitoring system which allows a remote user to monitor a patient and to assist that patient in daily functions throughout the day.

FIG. 16A is a first screen shot of a screen 1601 which can be used on a portable device such as a portable phone 70 or tablet computer 80, which assists a user in finding his clothes. Disclosed therein, is an information bar 1602 and check boxes 1603 which indicate the steps that the user can perform. There are a series of push buttons or activatable bars 1604, 1606, and 1605 which are configured to allow the user to control the program. For example, bar 1604 allows the user to indicate or communicate to the system (application server 120, or central processor such as processor 72 of phone 70) whether the task has been completed (See FIG. 16B). Bar 1605 is for indicating to the system that the user is having an emergency. Bar 1606 is for indicating to the system that the user needs help (See FIG. 16G). Therefore, this screen allows the user to receive more information on the task (See FIG. 16D-16F), While the terms "buttons"; "bars" or other elements may be used, in the case of a touch sensitive flat screen, these "buttons" or "bars" are simply touch sensitive flat graphical images on a screen which are simply indications of selections that can be made using the touch screen.

Figure 16B:
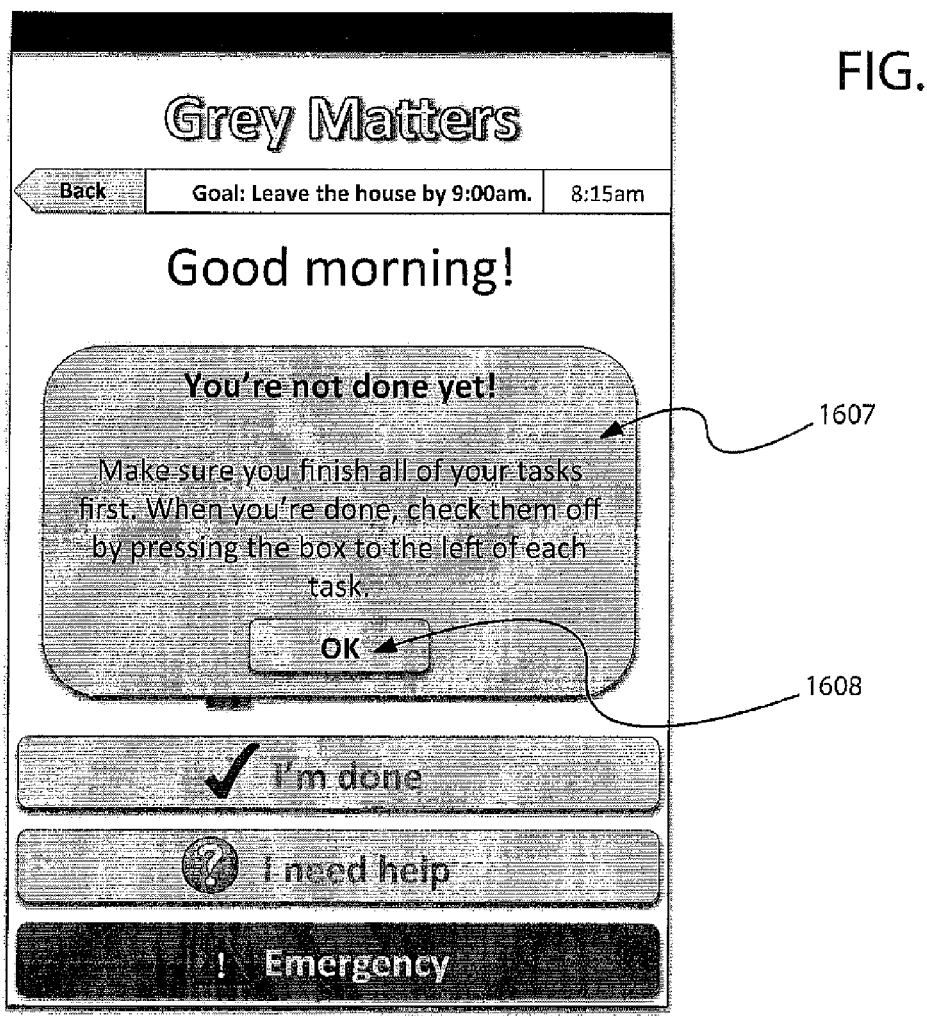
FIG. 16B is a screen shot of a next step of a portable program for assisting a patient in an executive functioning task.

FIG. 16B is the screen that indicates that the person has not completed all of the steps for that particular task. For example, if the user pressed the bar or button 1604 indicating that they are done, but they have not completed all of their tasks, then the system presents a screen indicator 1607 which indicates that the user has not completed his or her task. In addition, there is an "ok" button 1608 which allows the user to proceed past this step to complete his or her task. Once the user presses the "ok" button then the instructions are sent to the system to allow the process to proceed.

Figure 16C:
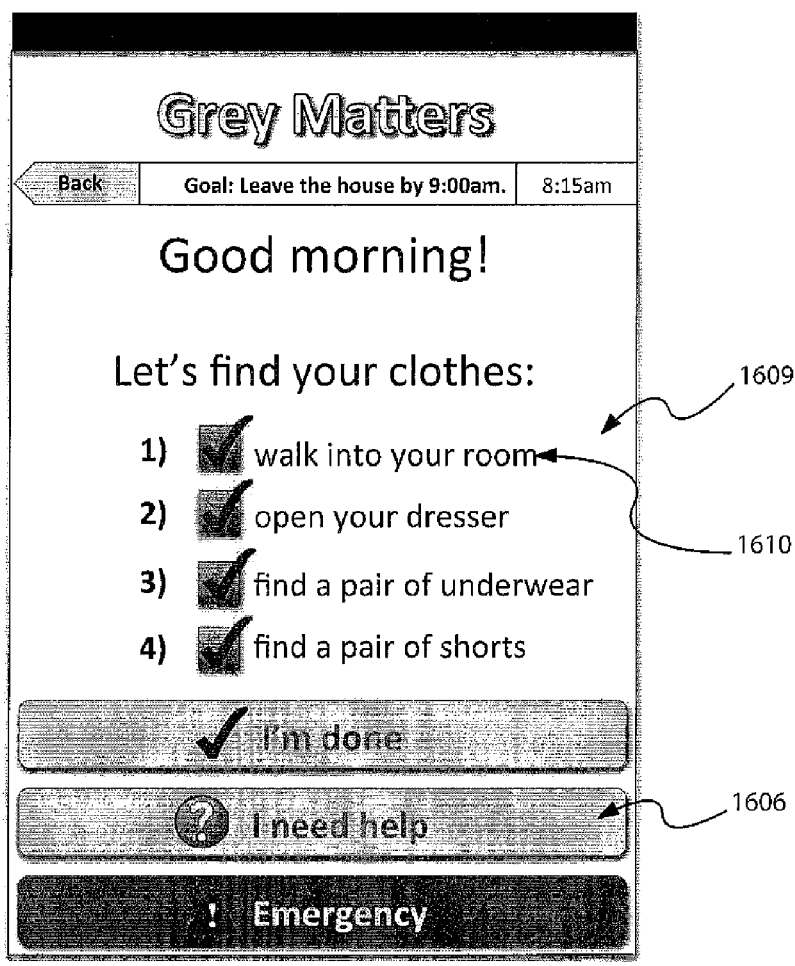
FIG. 16C is a screen shot of a screen on a portable computing device indicating the steps of the task have been completed.
Figure 16D:
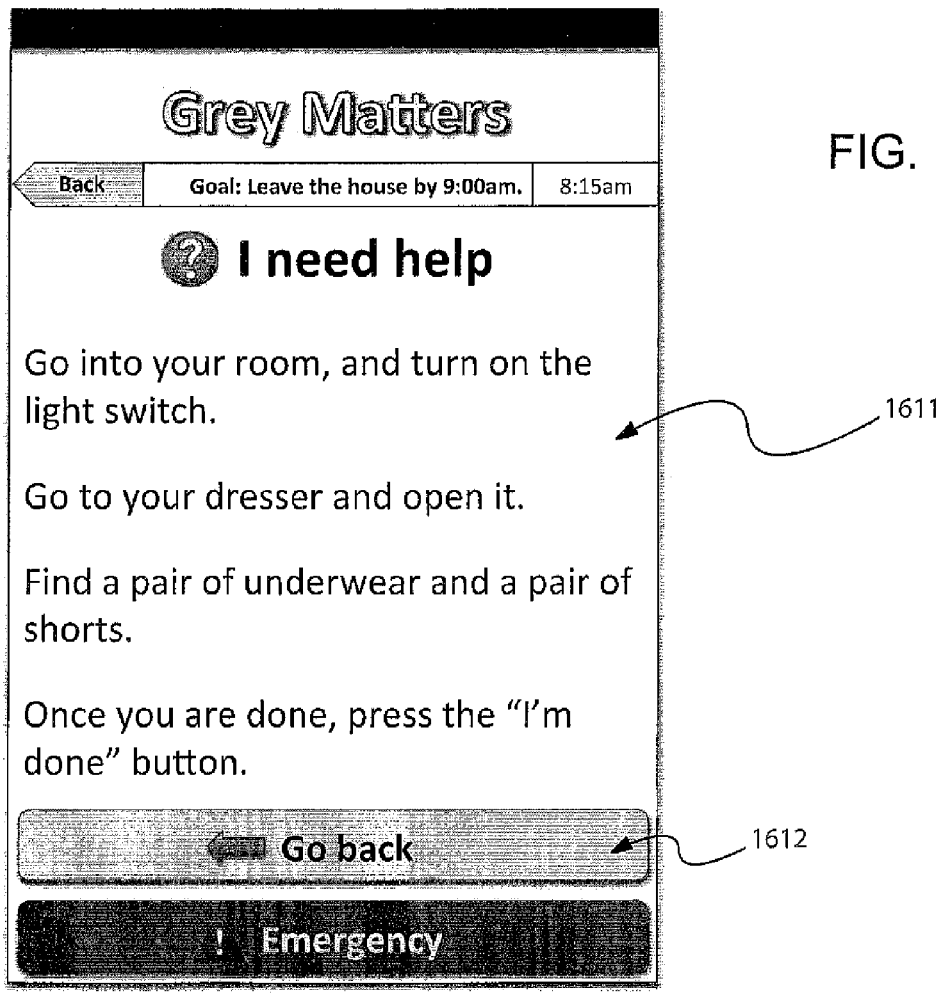
FIG. 16D is a screen shot of another screen indicating that the user needs help.

FIG. 16C shows a screen 1609 which shows each of the steps being completed as shown by associated steps with check boxes 1610. By selecting all of the check boxes, the user can indicate that he or she has completed all of the steps in that particular task. This information is then relayed into either the memory 73 of a phone 70, or into first the application server 120 and then onto the database server 130. FIG. 16D is a screen which appears after the user has selected button or bar 1606 (See FIG. 16C) which relays an indication to the system that the user needs help. Therefore, screen 1611 appears which provides helpful hints to the user on how to perform the particular steps of a task. Bar or button 1612 is also available to the users to allow the user to select to move back in the process to review the steps necessary for a task.

Figure 16E:
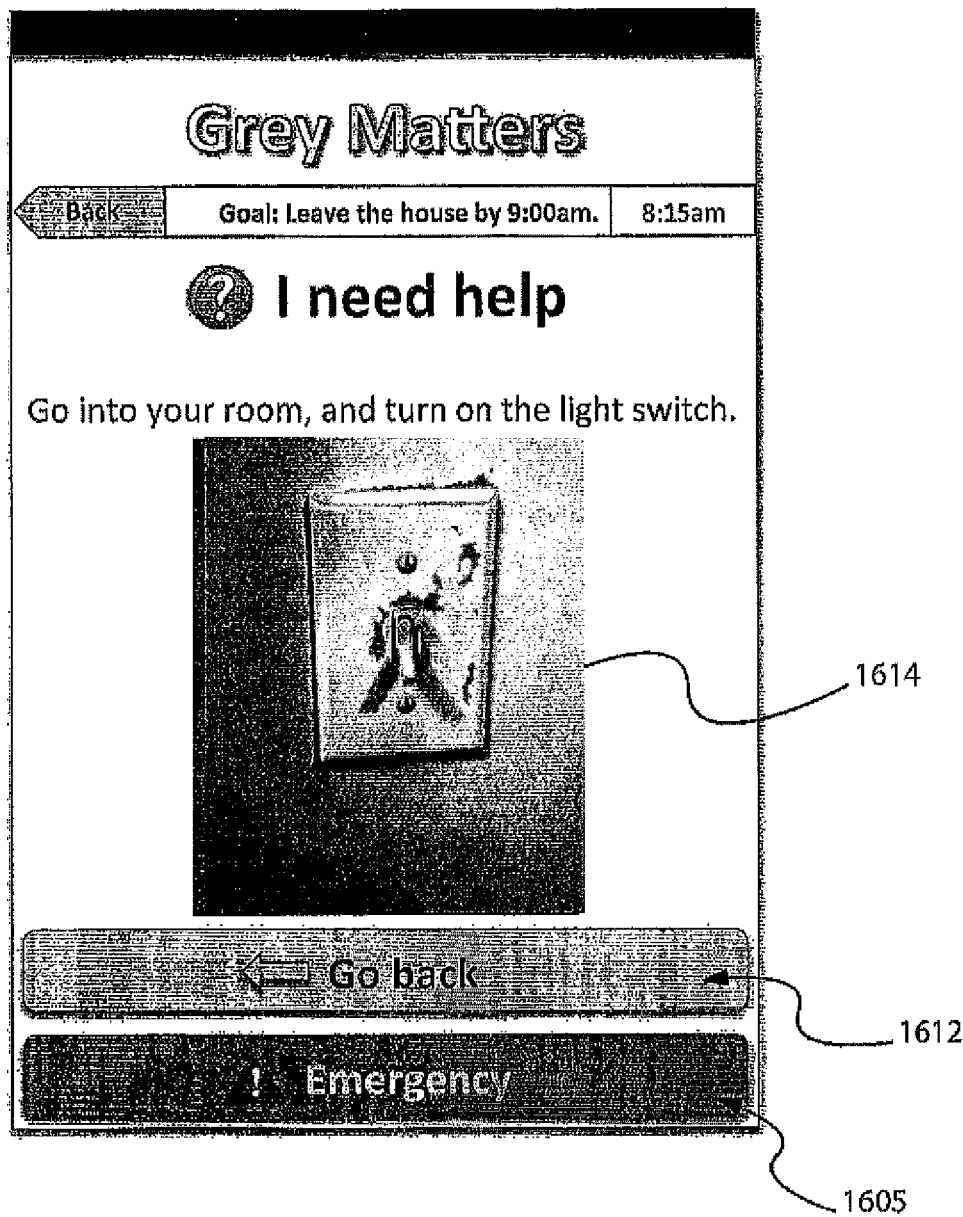
FIG. 16E is a screen shot of another screen providing help to the user.

FIG. 16E is a screen shot of additional help screens that provide images to the user to assist the user in completing the steps from a particular task. For example, when the user selects button 1606 indicating that they need help, this message is either sent only to processor/microprocessor 72 on phone 70 to pull this information stored in memory 73 or it is sent on to application server 120 to pull images that can be stored on the cluster of storage servers 140, 142, 144 or 146 to pull the image down from these storage devices. This information is then present for the user/patient to provide a visual recollection to the patient to assist them in performing their daily tasks.

Figure 16F:
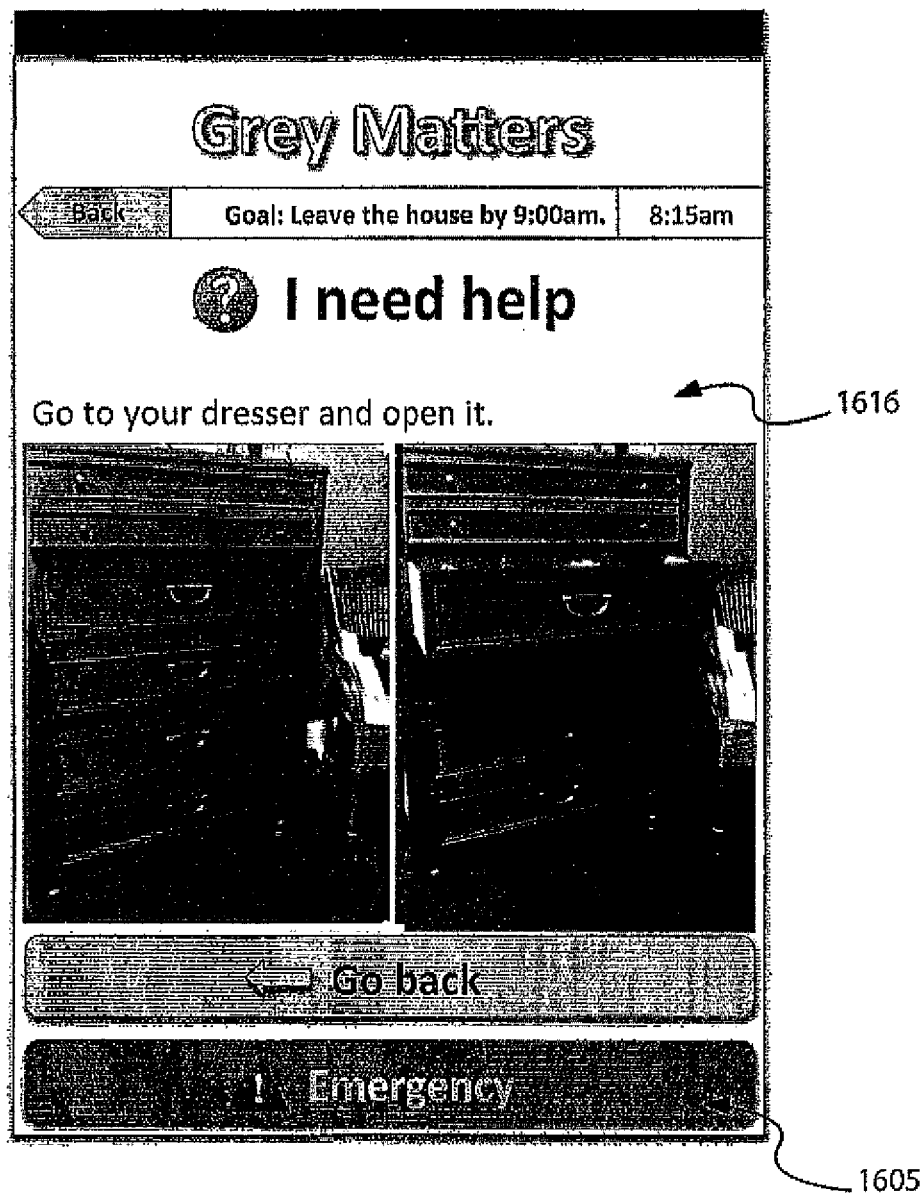
FIG. 16F is a screen shot of another screen for assisting a patient in an executive task.

FIG. 16F shows a screen shot of additional images 1616 presented to the user to show the user how to complete a series of steps or to entirely complete a task. These additional images can also be pulled from the cluster of servers 140, 142, 144, 146.

Figure 16G:
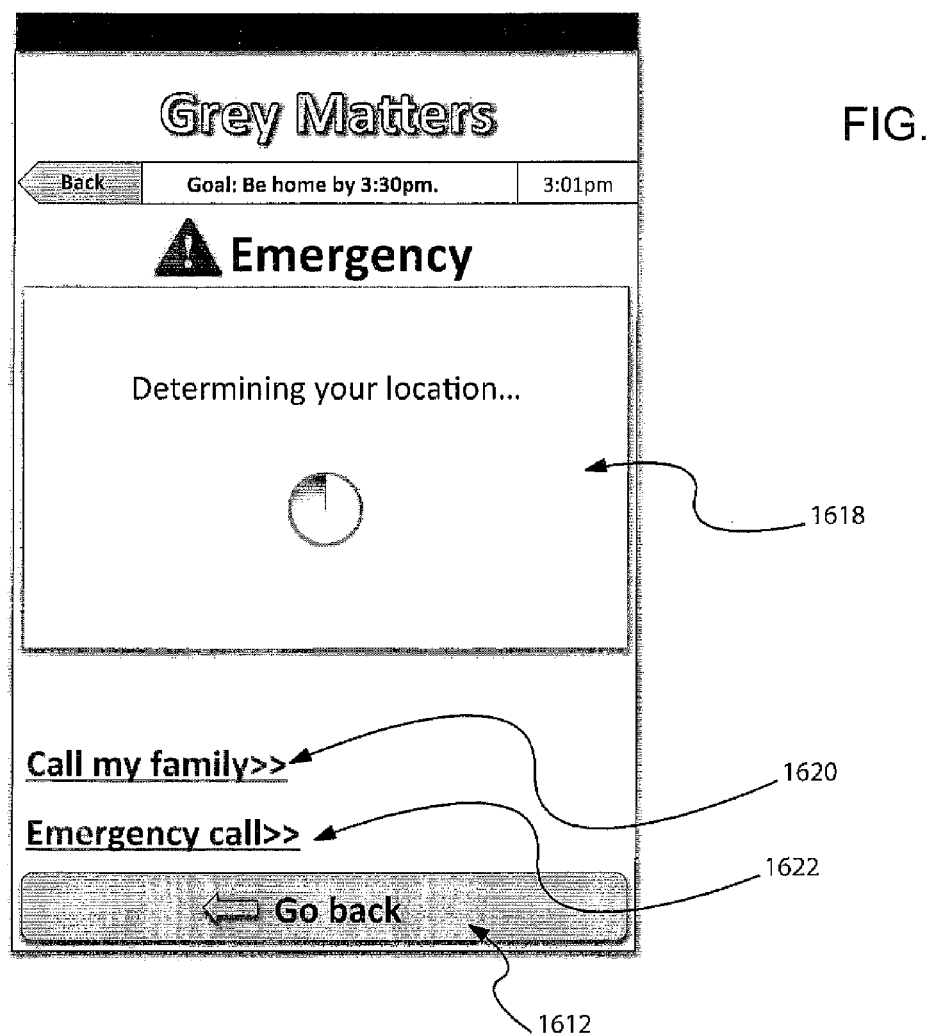
FIG. 16G is a screen shot of a user calling for assistance with an emergency.

FIG. 16G is a screen shot of a screen after a user has pressed button 1605 (See FIG. 16A). This indicates that the user is experiencing an emergency and wherein the system provides screen 1618 as well as options to the user to either call their family in button 1620 or to make an emergency call in button 1622.

In addition, as shown, the user can also select bar 1612 to go back to a previous screen to stop the emergency procedure. With this design, the system can use a GPS communicator installed onto a portable phone to bring forth an image of a map for the location of the user.

Figure 16H:
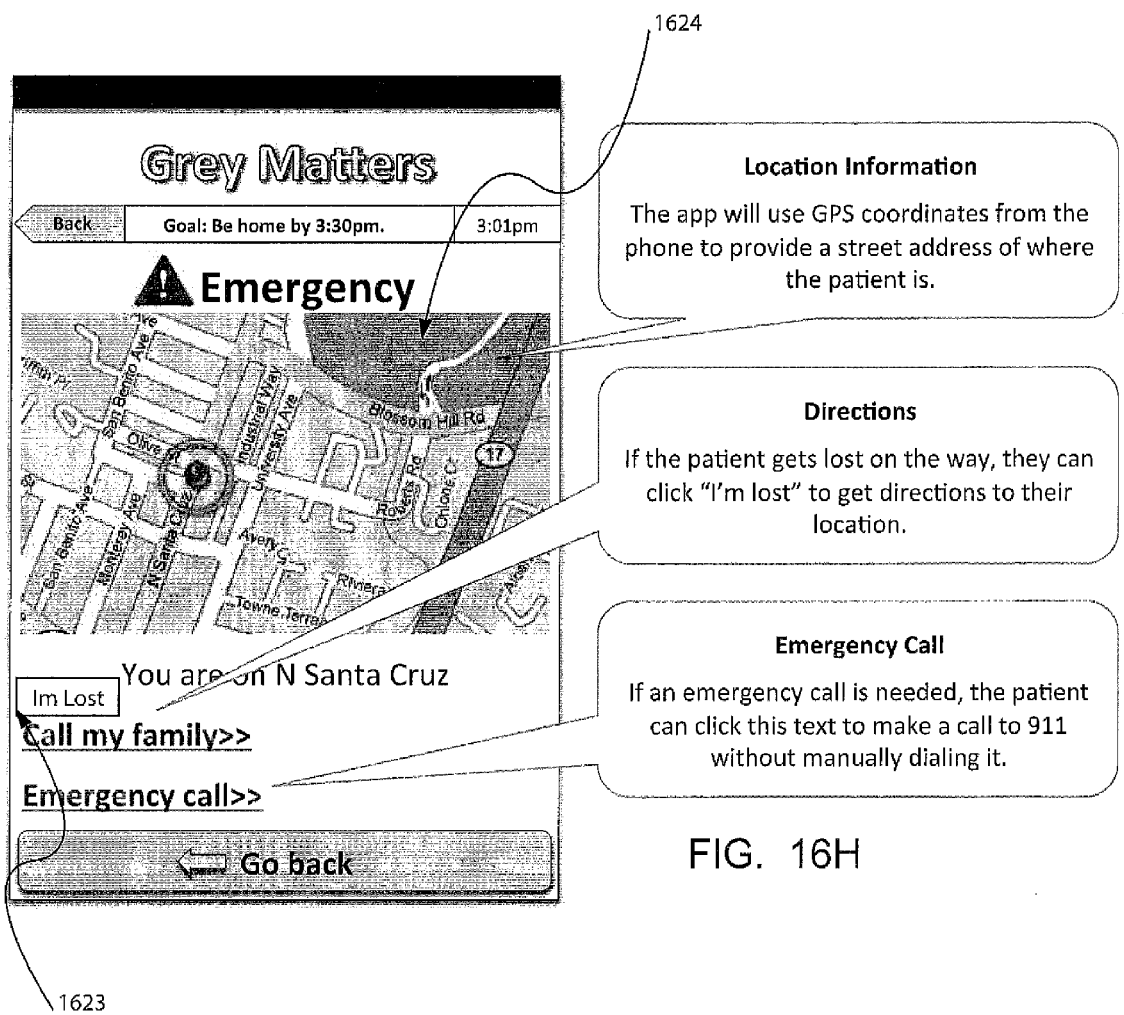
FIG. 16H is a screen shot indicating the address of the user calling for assistance with the emergency.
Figure 16I:
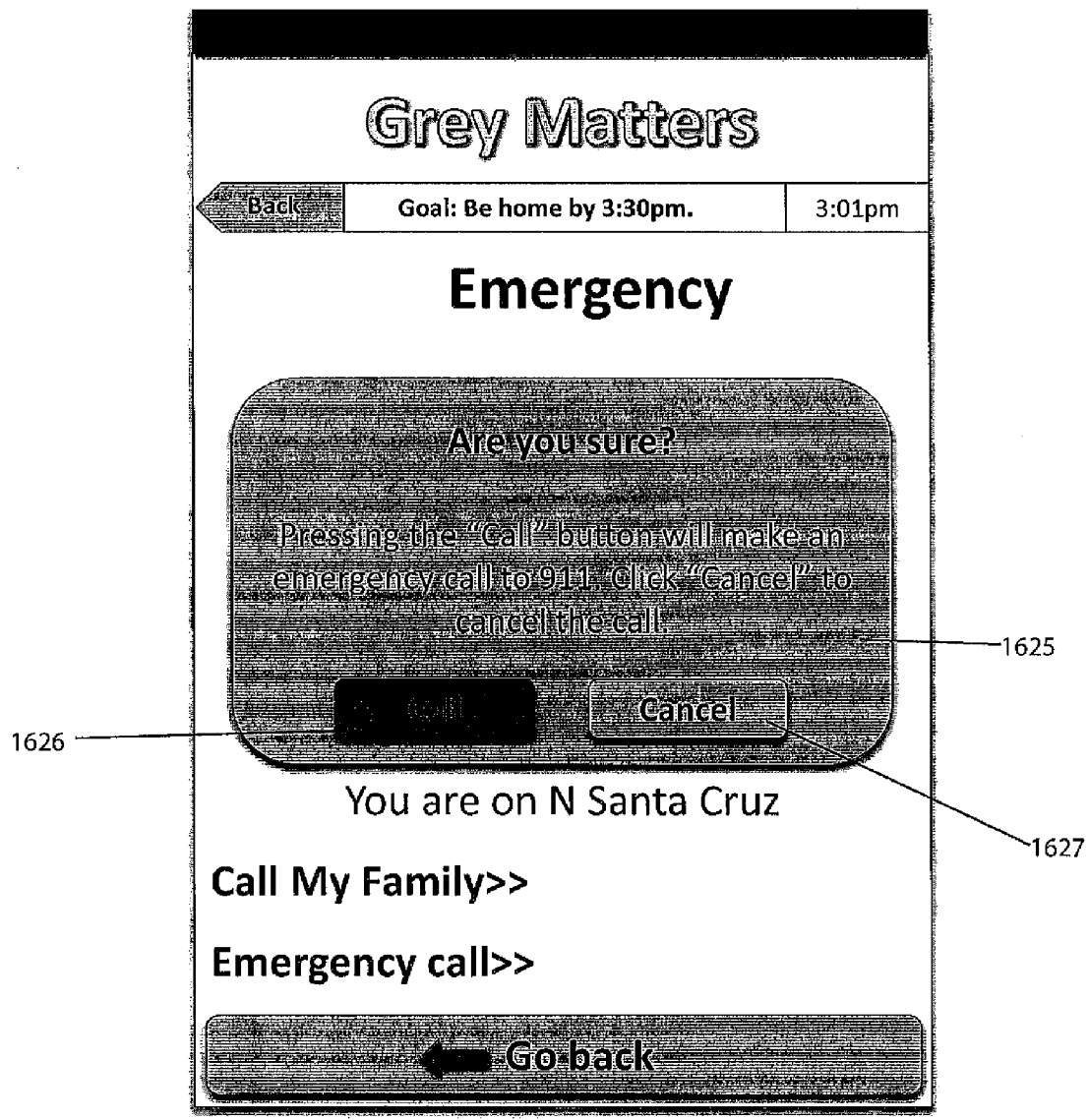
FIG. 16I is a screen shot of another screen providing the user with the ability to call assistance.

As shown in FIG. 16H this step can pull an image of a map from any suitable outside source such as a mapping database or from for example storage servers 140, 142, 144 and 146. Therefore, once this map image is pulled by processor 72 this image appears on screen 1624. At this stage, the user can also select button 1623 to indicate that they are lost to request more directions. This step would instruct processor 72 to pull directions from internal on the phone 70 memory 73 or mass storage 74 or to pull this information from other servers such as servers 140, 142, 144, 146 etc. Alternatively, the user can select one of the other buttons 1620 or 1622 to either call the user's family or to place an emergency call.

For example, if the user pressed button 1622 to place an emergency call, this would instruct processor 72 to present screen 1625 which is a confirmation screen to allow the user to confirm whether they will call the authorities such as "911". This screen 1625 presents at least two additional buttons for users, a call button 1626 and a cancel button 1627. The user can select either one of these buttons to move to the next step.

Figure 16J:
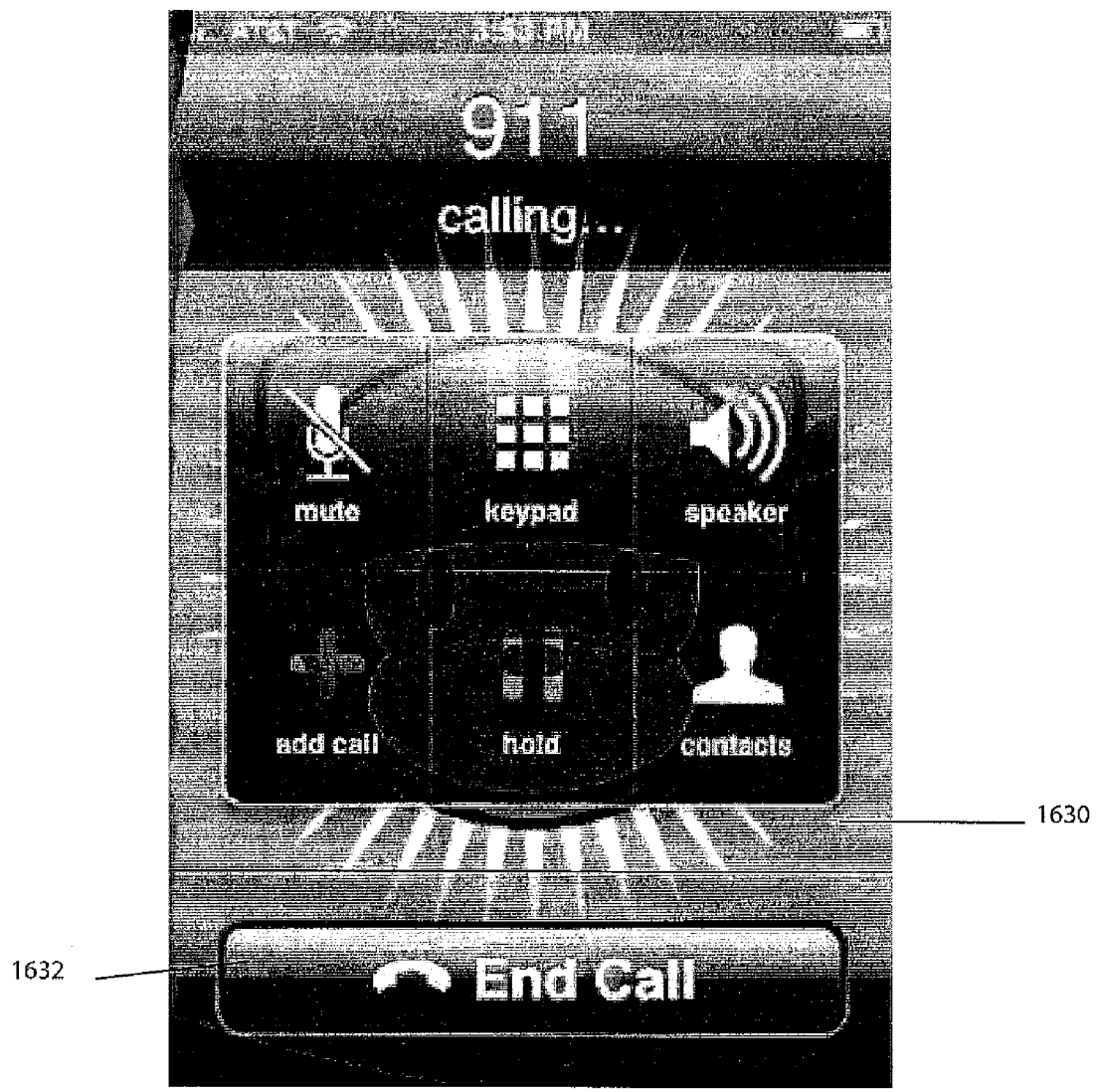
FIG. 16J is a screen shot of another screen indicating that the user has called for emergency assistance.

For example, FIG. 16J provides a call screen which is presented after a user selects call button 1626 which instructs processor 72 to place a call to "911" and to present screen 1630. A button 1632 appears via instructions from processor 72 which allows a user to voluntarily end the call as well.

Figure 16K:
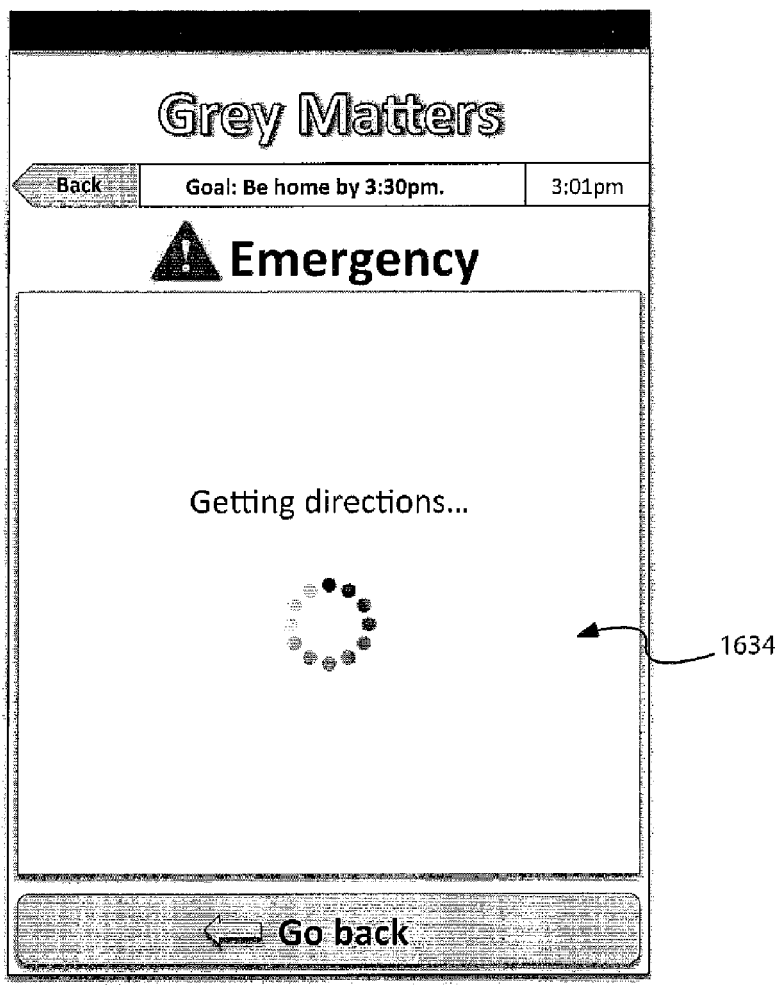
FIG. 16K is a screen shot indicating to the user how to use the directions if they are lost.
Figure 16L:
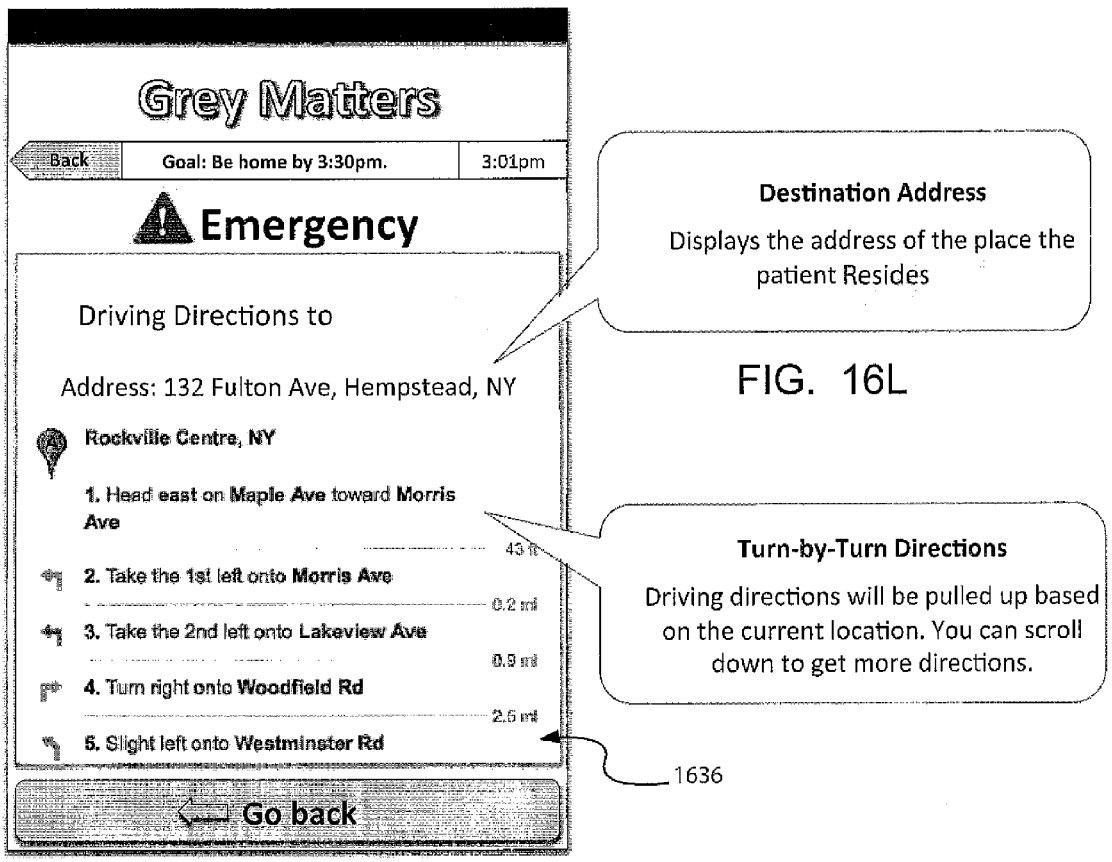
FIG. 16L is the screen indicating to the user directions where to proceed.

Alternatively, if the user selects button 1627, then the system can proceed to screen 1634 in FIG. 16K where processor 72 pulls a set of driving directions as shown in FIG. 16L. These driving direction are shown in screen 1636 which indicate both the destination address as well as the turn by turn directions that can be used.

Figure 16M:
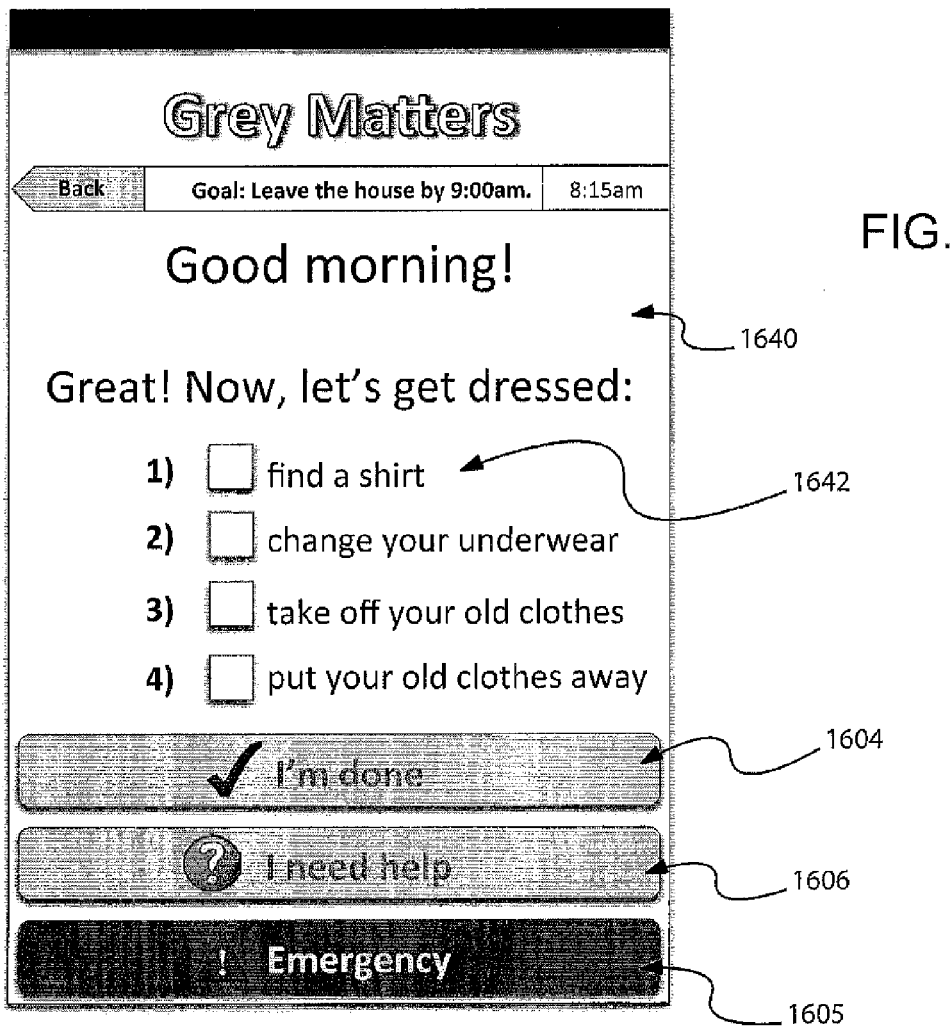
FIG. 16M is a screen indicating a series of steps for a user to perform another task.

FIG. 16M is a screen of another task that can be implemented by the user. For example, the user can be presented with screen 1640 wherein in screen 1640 there are a series of questions 1642 with an associated series of check boxes that the user can select. Different buttons 1604, 1606 and 1605 are also presented as well. This screen can be presented as instructed by processor 72. Processor 72 can decide to present this screen after the task originally shown in 16A has been completed.

Figure 16N:
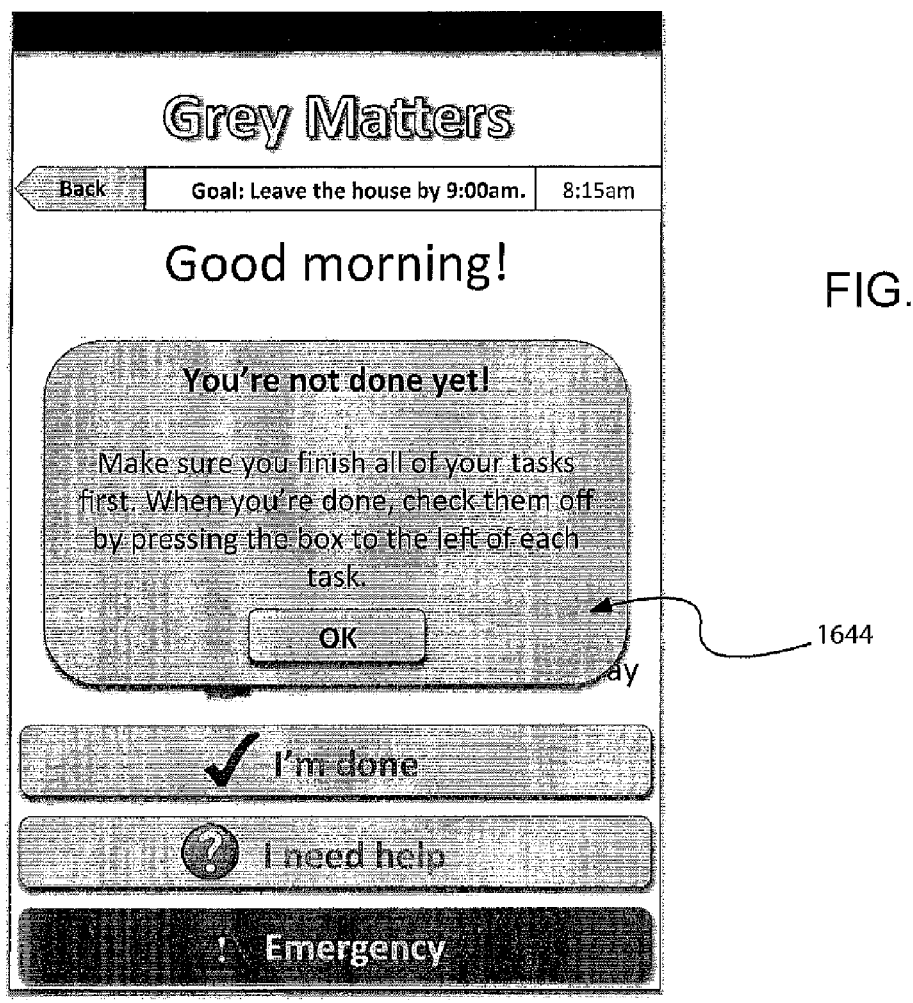
FIG. 16N is a screen indicating to the user that they have not completed their task.
Figure 16O:
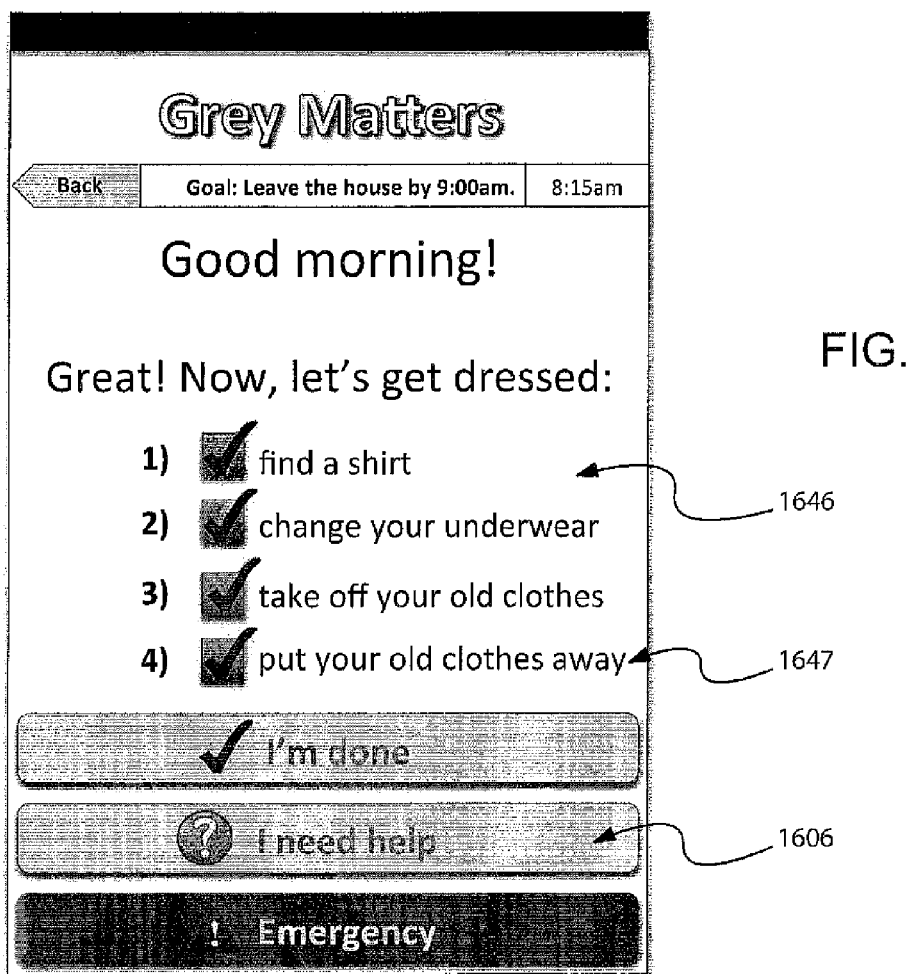
FIG. 16O is a screen indicating to the user that they have completed all of their tasks.
Figure 16P:
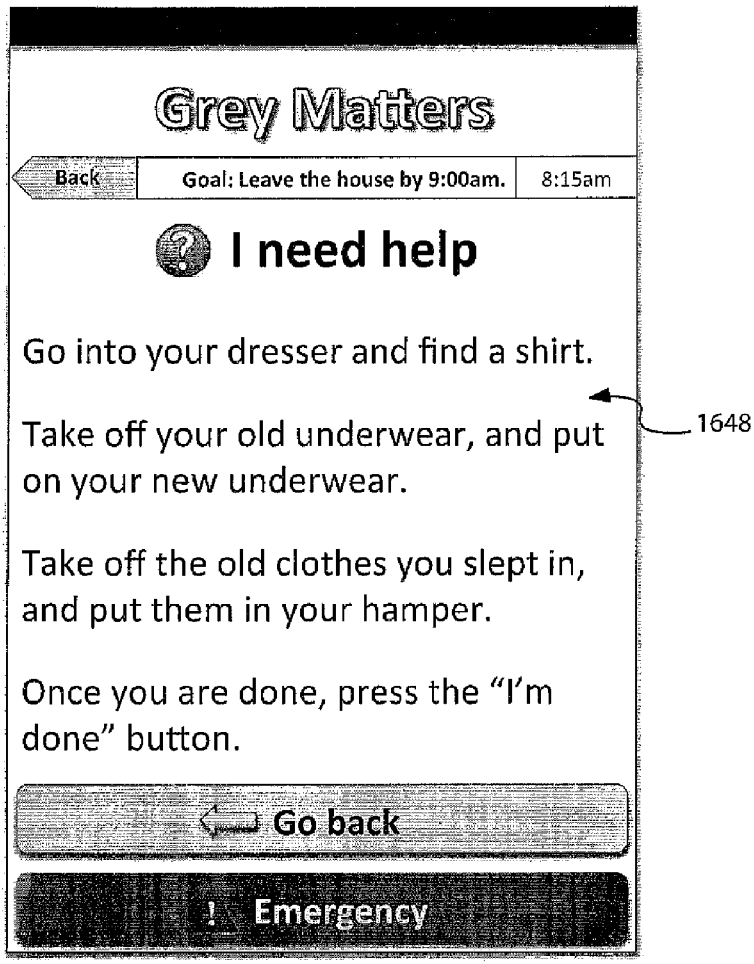
FIG. 16P is a screen indicating to the user that they need help.

FIG. 16N shows a screen 1644, which can appear after the user selects the button 1604 "I'm Done". This screen 1644 indicates to the user that they have not completed the task shown in FIG. 16M. FIG. 16O shows another screen 1646 which indicates that the user has selected all of the steps 1647 of the task to be completed. If at this point the user selects button 1606 "I need help" then a processor such as processor 72 presents screen 1648 which includes a series of additional instructions instructing the user on how to proceed with the task. This screen presents a plurality of instructions in the form of steps for the user.

Figure 16Q:
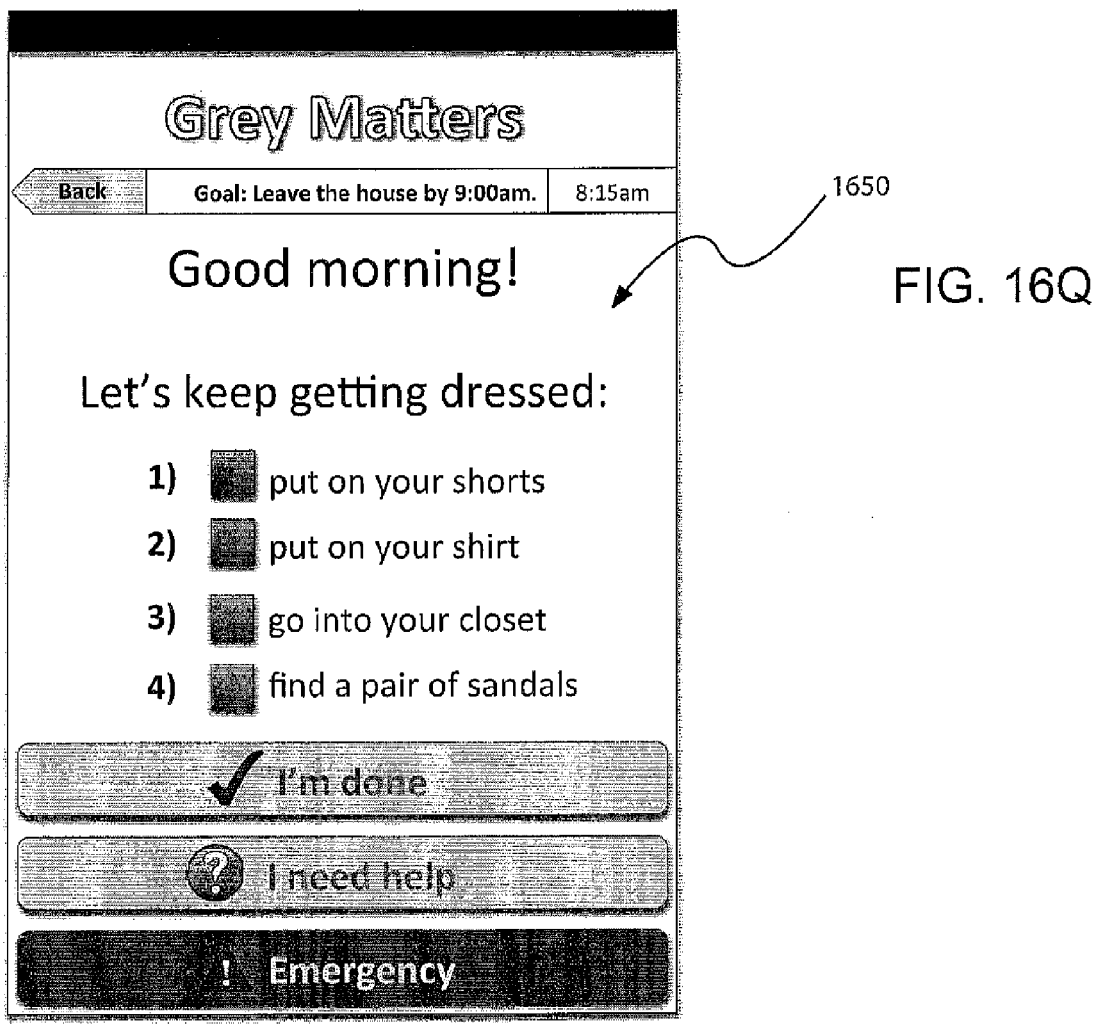
FIG. 16Q is a screen indicating to the user that they are to get dressed.

Processor 72 can then prompt the user in FIG. 16Q to keep getting dressed with screen 1650 which prompts the user to follow a series of additional steps.

Figure 16R:
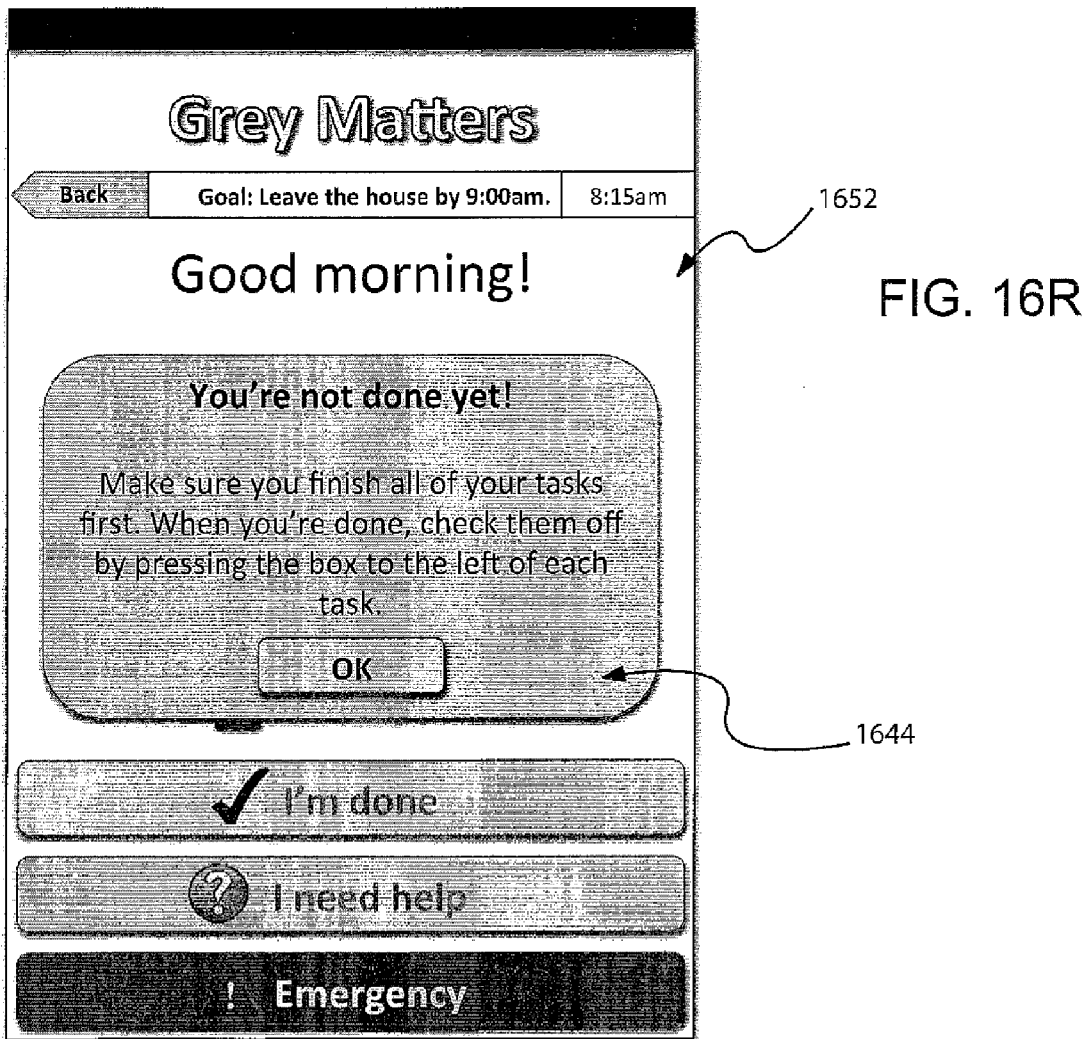
FIG. 16R is a screen indicating that they have not completed their steps for the task.

Next, FIG. 16R shows another screen 1652 which shows prompt 1644 which indicates that the user has not completed all of his or her tasks. This screen is presented if the user pressed button 1604 trying to indicate that they have completed all of the steps for their particular task.

Figure 16S:
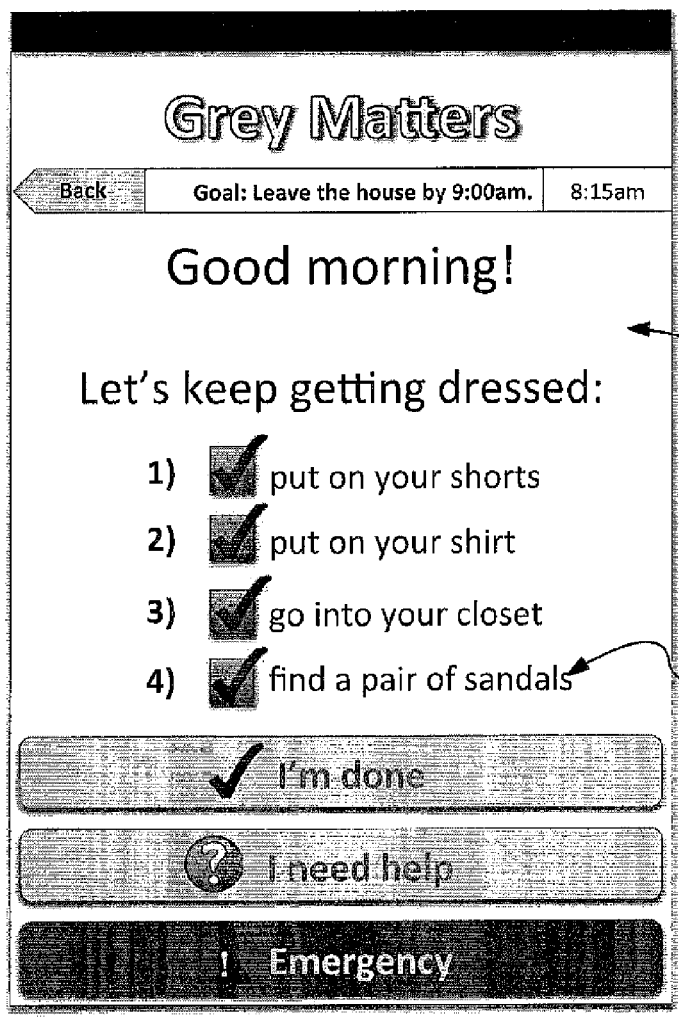
FIG. 16S is a screen indicating to the user that they have completed all of the steps for their task.
Figure 16T:
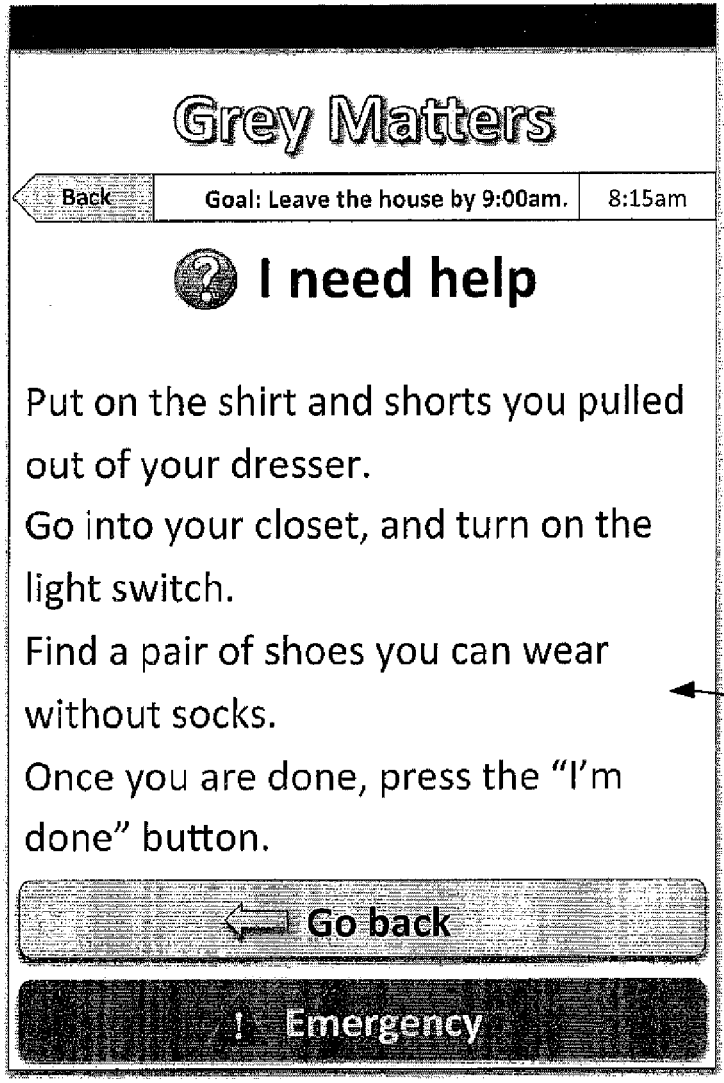
FIG. 16T is a screen indicating a series of suggestive steps to help the user complete the steps associated with the task.

FIG. 16S shows an additional screen 1654 which shows a series of tasks 1655 which have been completed. However, if the user selected button 1606 that they needed help on this task, then they would be presented with a screen 1656 which presents the user with a series of additional steps to complete a task.

Figure 16U:
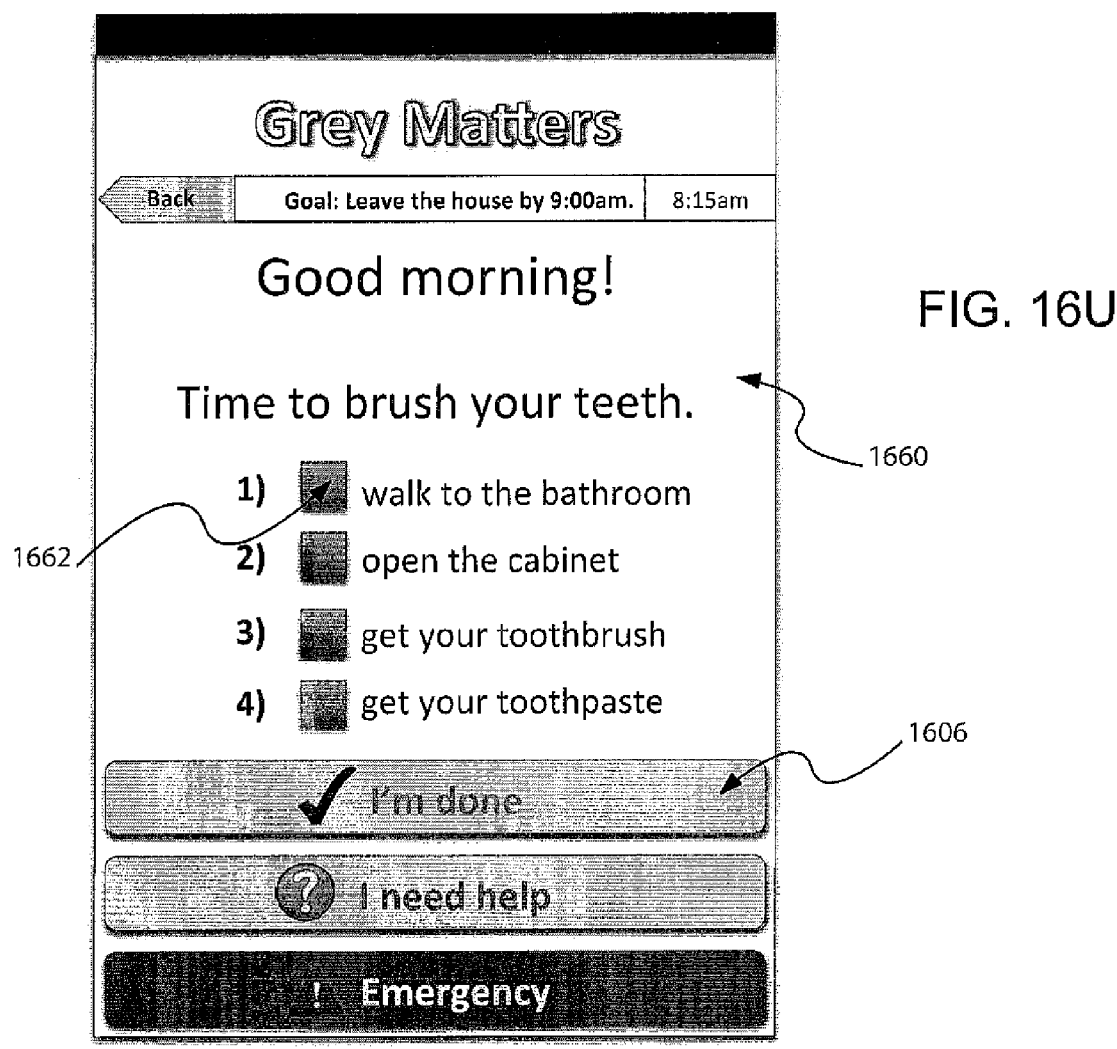
FIG. 16U is a screen indicating to the user that they have another series of steps for another task.
Figure 16V:
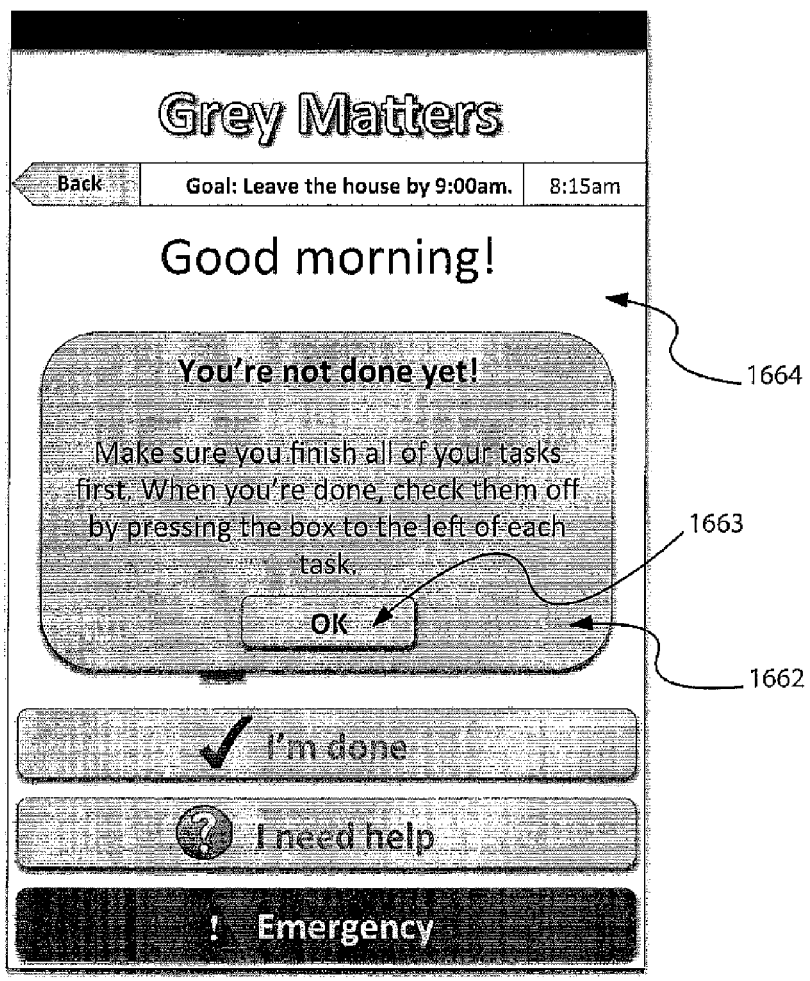
FIG. 16V is a screen indicating to the user that they have not completed their tasks.
Figure 16W:
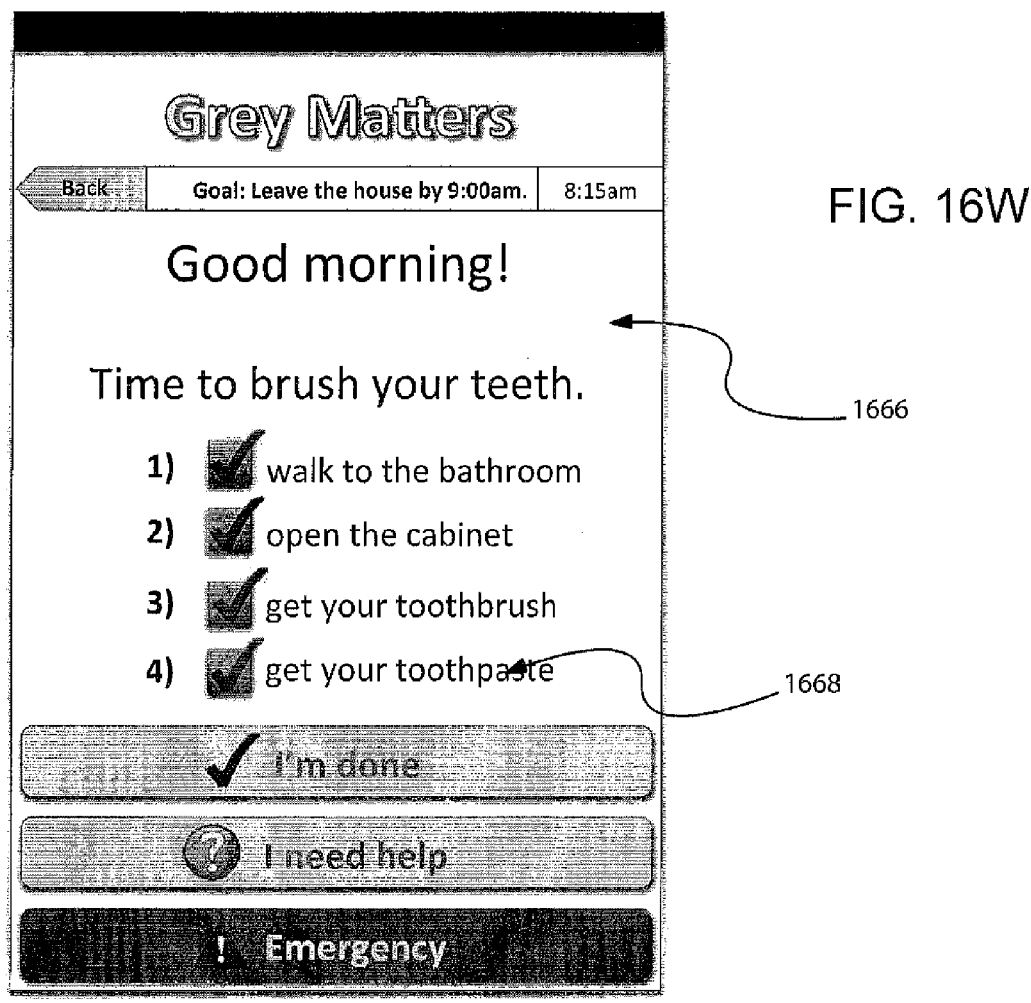
FIG. 16W is a screen indicating to the user that they have completed all of the steps for their task.
Figure 16X:
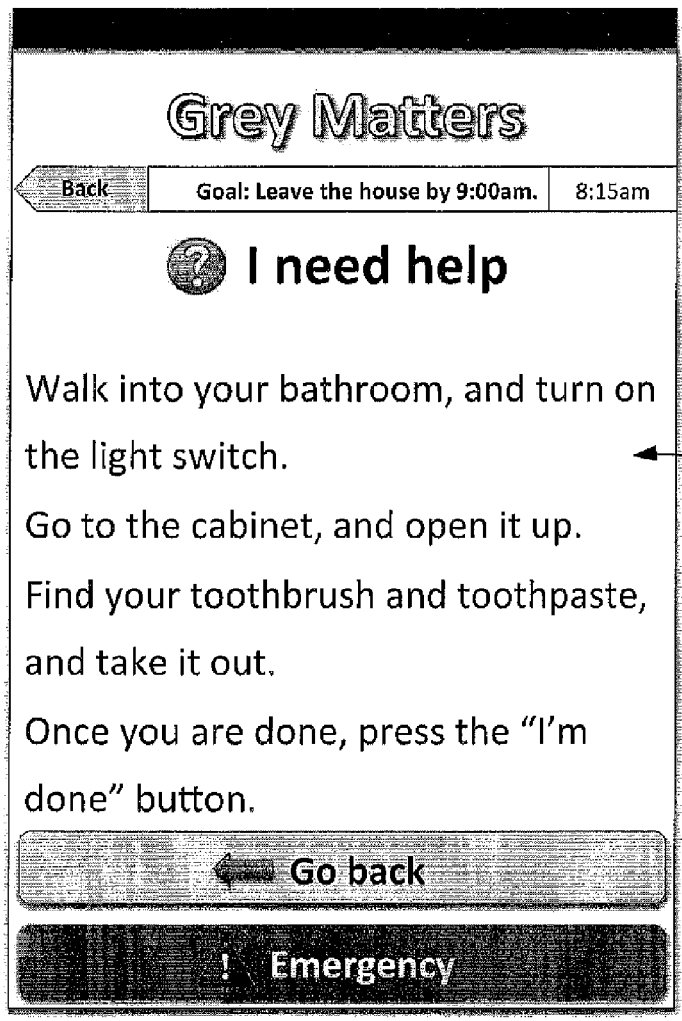
FIG. 16X is another screen indicating to the user a series of suggestions for the user in completing their task.

FIG. 16U shows another task which lists a series of steps 1622 for the user to complete. Again, if the user selects button 1606 then processor 72 presents screen 1662 that indicates to the user that they have not completed their task. By selecting button 1663, processor 72 returns the user to screen 1666 in FIG. 16W which then instructs the user to select the checkboxes for each step of the task to indicate that the user has completed this task. If however, the user selected button 1606 that they needed help, then processor 72 would carry out instructions uploaded from memory 73 to present the user with screen 1670. These steps on this screen can be stored in memory 73 or in mass storage device 74, or in any one of database server 130, or servers 140, 142, 144, 146.

FIG. 17A shows another screen for a task to be completed outside of the user's home. For example, this screen 1701 includes a back button 1702, a time indicator 1706, as well as the goal indicator 1704. There is an indication of a main task 1708, as well as a series of steps for completing the main task. Each step can have an associated check box 1710 which allows the user to check a box to indicate that they have completed a task. Additional buttons 1712 allow the user to indicate that they have completed the task, button 1714 allows the user to signal for help, and button 1716 allows the user to call for emergency help.

Figure 17B:
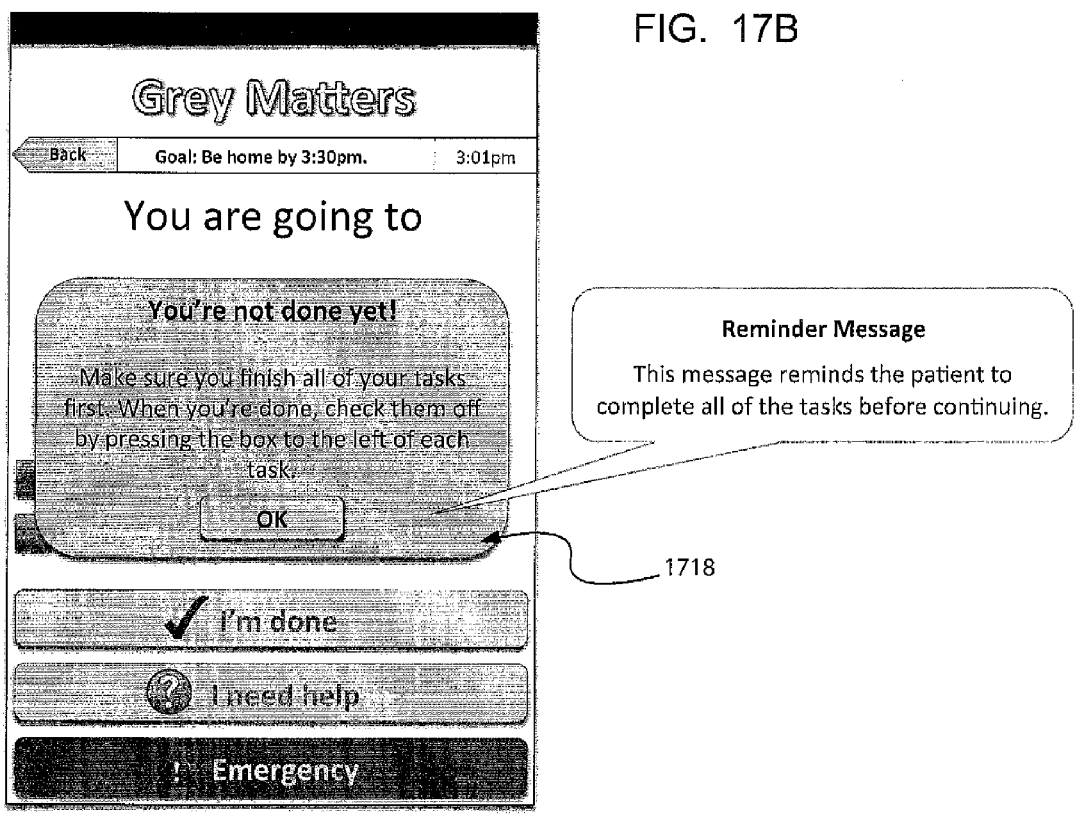
FIG. 17B is an indication screen to the patient that they have not completed all of the steps of their tasks.

For example, FIG. 17B shows a screen 1718 wherein processor 72 presents screen 1718 if the user selects that they have completed a task without completing all of the steps. Memory 73 keeps track of whether all of the steps of a particular task have been checked off. If the user selects button 1712 and all of the steps of the task have not been checked off then processor 72 presents screen 1718.

Figure 17C:
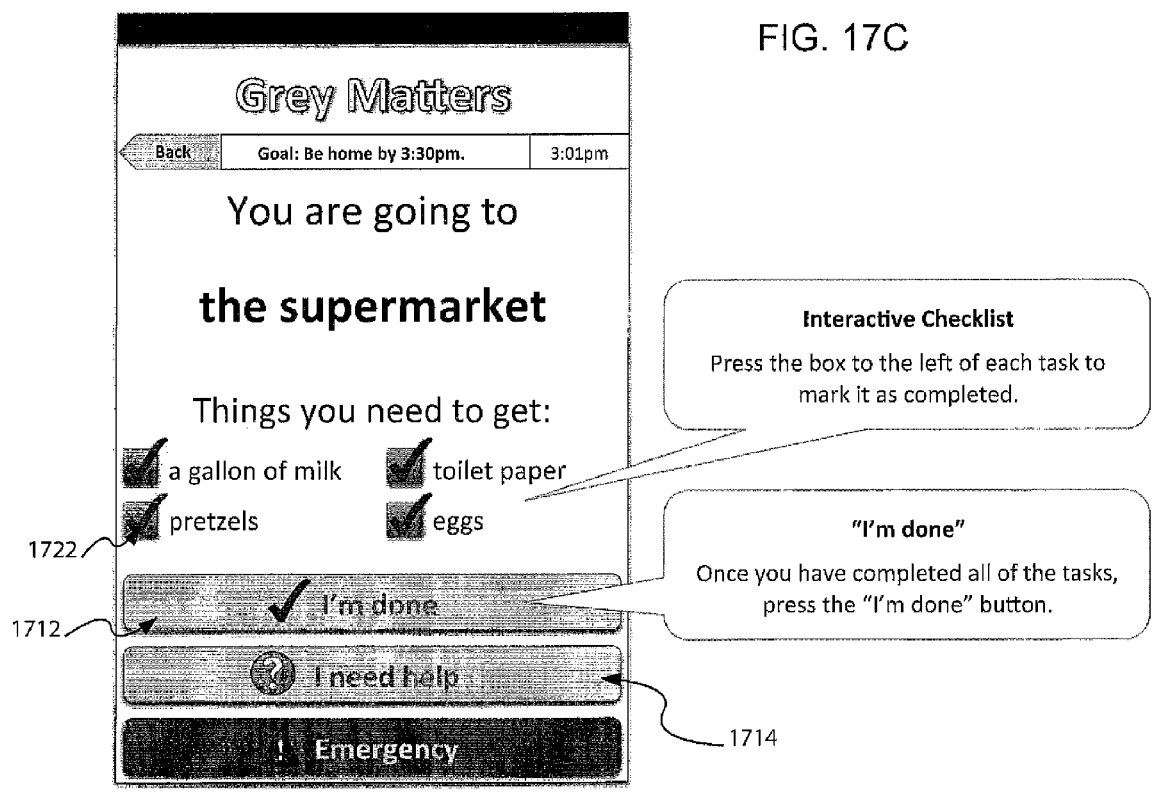
FIG. 17C is a screen indicating that they have completed all of the steps of their task.
Figure 17D:
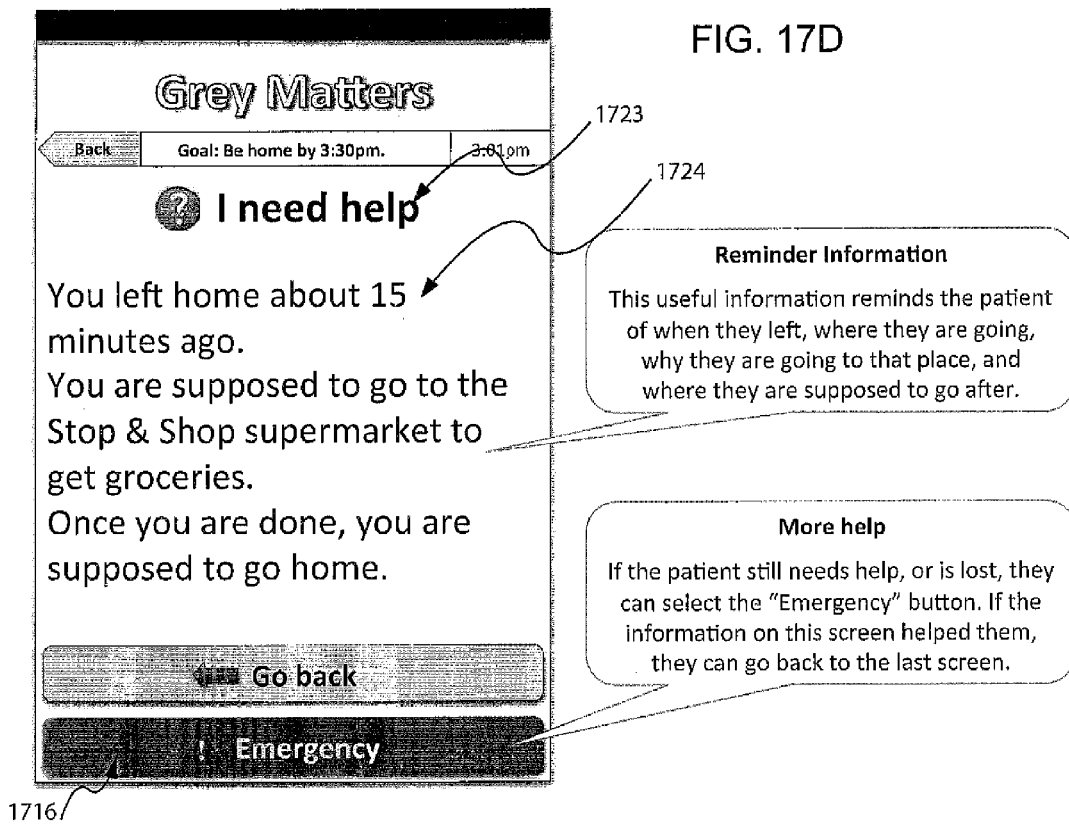
FIG. 17D is a help indication screen for the patient.

Therefore, FIG. 17C shows another screen which shows that the user can select check boxes 1722 to indicate that the steps of the task have been completed. Next, once all of the steps of a particular task have been completed, then the user can select button 1712 to indicate that they have completed all of the steps of the task. However, if the user needed help, then the user can select button 1714 which results in screen 1724 being presented which indicates in section 1723 that the person needs help.

Alternatively, if the user selects button 1716 then the user would be presented with emergency screen 1729, which includes emergency indicator 1730 as well as map 1732. Once emergency button 1716 has been selected, processor 72 then presents the user with this screen which also includes a button 1738 to allow the user to signal that they are lost or button 1736 to allow the user to place an emergency call. The user can also press a button 1734 to go back to a previous screen.

Figure 17F:
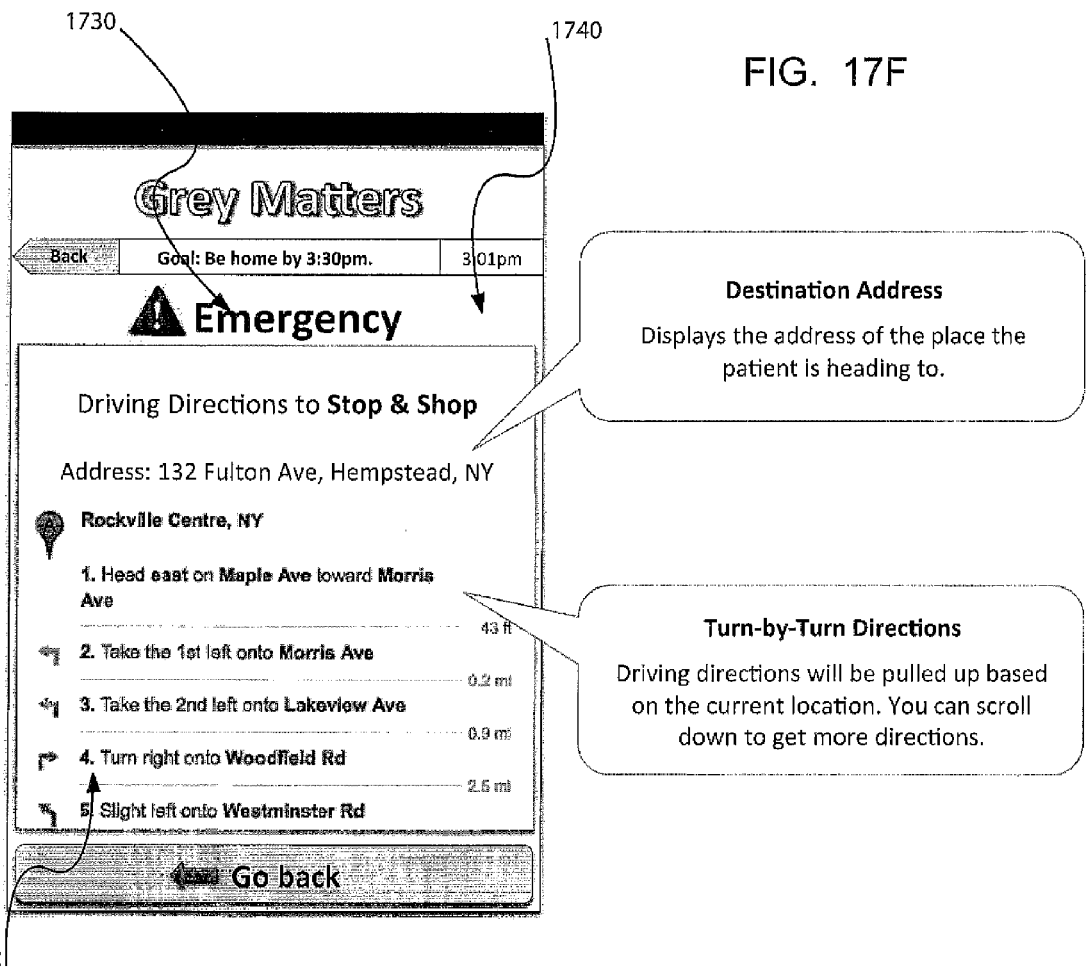
FIG. 17F is a screen indicating how to get to a destination.

If the user presses button 1738, then the user is presented with screen 1740 shown in FIG. 17F. This screen includes emergency indicator 1730 as well as turn by turn instructions 1742 as well. This information is pulled by processor 72 from either memory 73 or from database server 130 into memory 73, or from any one of servers 140, 142, 144, 146 to memory 73. Thus, outside personnel such as medical professionals or first responders can find the user/patient if he or she is in trouble.

Figure 17G:
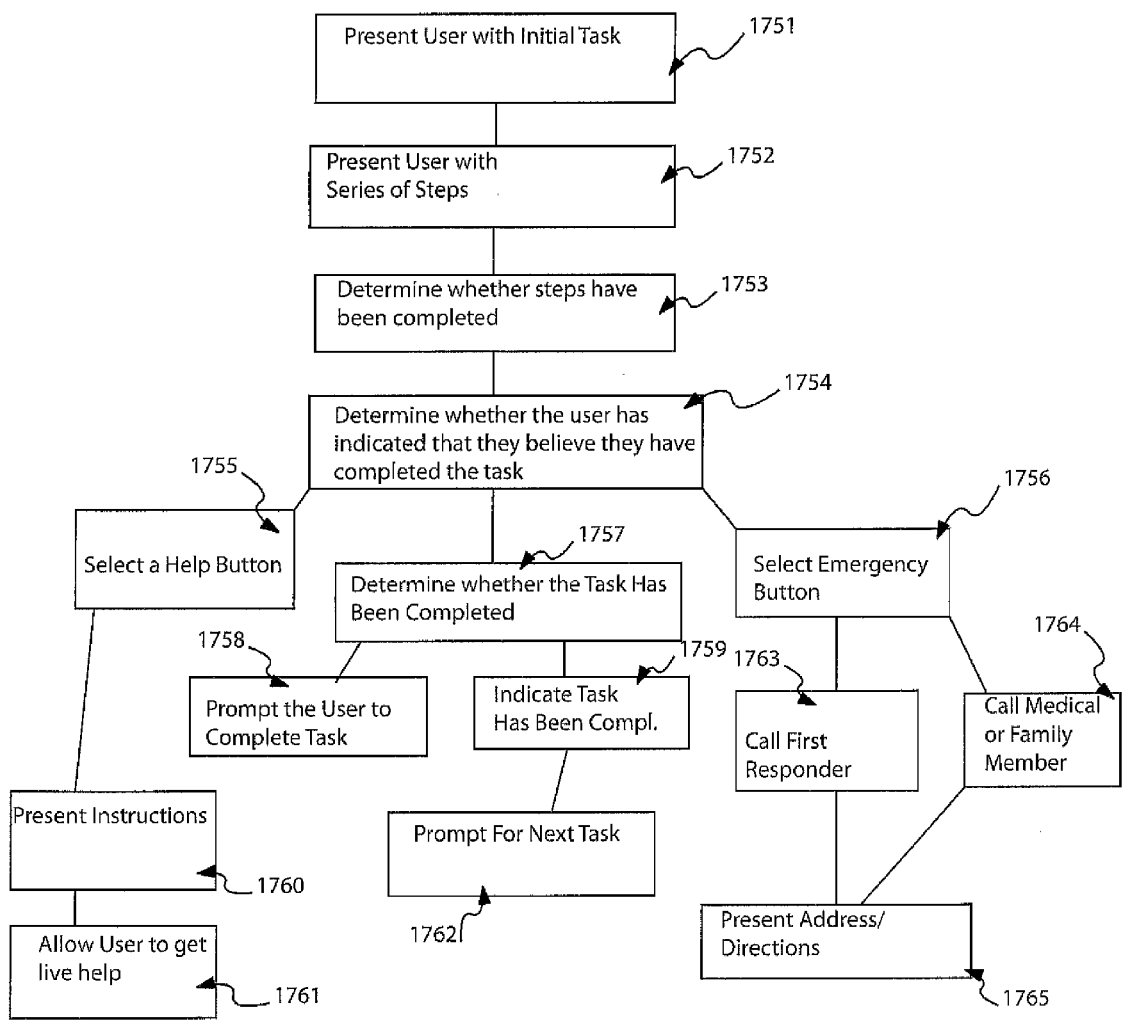
FIG. 17G is a flow chart for a process for assisting a user in his or her executive functioning tasks shown in FIGS. 6A-17F.

FIG. 17G shows the general for a user through this process shown by way of example in FIGS. 16A-17H.

For example, in step 1751, the user is presented with an initial task such as the initial task shown in FIG. 16A. Processor 72 can present this task based upon a location of the user, a voice, or typing instruction of a user, based upon a prompt from an external agent, or based upon processor 72 checking an internal clock on processor 72 to determine the time of day. For example, if processor 72 determines that it is 8:00 AM and the user usually gets dressed, then processor 72 can present the user with screen 1601 shown in FIG. 16A. Next, the user is presented with a series of steps for the task such as shown by steps 1710 in FIG. 17A. With this screen, these steps 1710 must be completed by the user before the system (processor 72) allows the user to proceed forward. For example, in step 1753, processor 72 is used to determine whether the steps 1710 have been completed. If these steps have been completed, then the system can proceed to step 1757 to determine whether the task has been completed. If however, the user presses button 1712 prematurely then the system can prompt the user to complete the task in step 1758 which is shown by way of example by screen 1718. Alternatively if the steps have all been completed and the user presses button 1712 then the processor 72 can indicate to the user that the task has been completed in step 1759.

Next, once that task has been completed, depending on whether there are any related tasks, or on the time of the day, or on prompts from the user, or outside sources communicating with mobile device or phone 70, the system (processor 72) can prompt the user for a next task in step 1762.

Alternatively, if the user selects a help button 1714 in step 1755 then the system can present the user with a series of instructions in step 1760. These instructions are shown in screen 1724. Step 1761 allows the user to get live help by communicating with an outside family member or health care professional or call service (See FIG. 15) to obtain assistance on a task.

Alternatively, if the user selected an emergency button 1716 in step 1756 then the system (processor 72) would call a first responder 1763 or alternatively call a medical professional or family member in step 1764. While the user is waiting for emergency assistance, the system can present the outside first responder or medical professional or family member with directions on how to reach the user in step 1765.

In all, the system and process creates an automatic diagnosing or determination system and process which can then be used to treat and monitor a patient. If the patient is able to function even at a minimal level, then the patient can operate on their own without any additional home health aides/social worker through the use of a portable assistance system.

Accordingly, while at least one embodiment of the present invention have been shown and described, it is to be understood that many changes and modifications may be made thereunto without departing from the spirit and scope of the invention as defined in the appended claims.

What is claimed is:

1. A computerized system comprising:
a server comprising a microprocessor and a memory, the server configured to provide a database configured to store information about a user;
wherein said server is configured to receive personalized information about a user
said server is configured to store said information in said database as data in a storage device;
said microprocessor is configured to select at least one question for presentation to a user based upon said user's personalized information;
a remote device configured to present said at least one selected question to a user on a remote device;
said memory is configured to record at least one answer provided by said user in said storage device in said database;
said remote device is configured to test at least one user's speech abilities by presenting at least one personalized-question to said user;
a voice recognition system comprising at least a microphone coupled to the remote device to score the ability of the user to engage in vocal speech repetition;
a screen coupled to said remote device and configured to present a task to a monitored user;
a GPS communicator coupled to the remote device configured to track a user's movements;
wherein said remote device that is triggered when the monitored user fails at said task;
a gyroscope coupled to the remote device, wherein the gyroscope is configured to indicate whether the device has been moved in location, rotated or elevated;
wherein the remote device is configured to notify another user of the user's movements by communicating GPS information about the remote device;
wherein said microprocessor in said server is configured to determine a user's medical condition by determining using a grading system the user's condition based upon at least one answer in response to said at least one question and based upon the user's speech ability;
wherein said server is configured to determine a treatment for a user's medical condition based upon said at least one answer in response to said at least one question based upon said user's ability to recall personalized information and based upon said user's speech ability, and based upon the user's ability to complete said task.

2. The system as in claim 1, wherein said screen is configured to present at least one question to a user, uploaded from said database, wherein said step of treating a user's medical condition comprises presenting said personalized information on said screen to said user to test a user's memory.

3. The system as in claim 1, wherein said remote device is configured to test a users' speech capability by presenting at least one task for speaking to the user, comprising at least one speech repetition task and wherein said microprocessor is configured to test a user's medical condition by determining using a grading system grading the user's speech condition.

4. The system as in claim 1, wherein said database comprises a plurality of tables which store information about the user comprising at least one of: first name; last name, birth date, sex (male/female); medical history.

5. The system as in claim 1, wherein said database is configured to receive personalized information about a user which comprises at least one of pictures, music, and videos in said database.

6. The system as in claim 1, wherein said database is configured to store information about a on a database server.

7. The system as in claim 1, further comprising a storage server in communication with said database server, said storage server for storing any media comprising at least one of: pictures, videos, or music.

8. The system as in claim 1, further comprising providing an application server, wherein said application server provides at least one interface for uploading personalized media into said database wherein said step of testing at least one user's speech abilities is performed on said application server incorporating said personalized media.

9. The system as in claim 1, wherein said step of uploading personalized information comprises uploading personalized information from at least one of a personal computer, a tablet, a portable information device, a mobile telephone.

10. The system as in claim 1, wherein said step of presenting at least one question to a user comprises presenting at least one question on a portable display.

11. The system as in claim 1, wherein said step of presenting at least one question to a user comprises presenting at least one question comprising at least one picture comprising a personalized image and wherein said step of determining using said microprocessor a user's medical condition comprises determining using a grading system the user's ability to recall said at least one personalized image.

12. The system as in claim 1, wherein said step of presenting at least one question to a user comprises presenting at least one question comprising at least one musical file provided by the user and wherein said step of determining using said microprocessor a user's medical condition comprises determining using a grading system the user's ability to recall said at least one personalized audio or musical file.

13. The system as in claim 1, wherein said step of presenting at least one question to a user comprises presenting at least one question comprising at least one video file provided by the user and wherein said step of determining using said microprocessor a user's medical condition comprises determining using a grading system the user's ability to recall contents of at least one personalized video file.

14. The system as in claim 1, wherein said step of presenting at least one question comprises presenting at least one question relating to at least one of the following personal characteristics of the user: age, name, family information.

15. The system as in claim 14, wherein said step of presenting at least one question comprises presenting at least one question relating to pictures of family members.

16. The system as in claim 1, wherein said at least one question is presented on said remote device which relates to family members of a patient.

17. The system as in claim 1, wherein said user's speech abilities are tested using said at least one microprocessor on said remote device.

18. The system as in claim 1, wherein said microprocessor on said server and at least one microprocessor on said at least one remote device is configured to test said at least one user's speech abilities.

19. The system as in claim 17, wherein said microprocessor on said server is configured to determine a user's medical condition by determining using a grading system the user's condition based upon at least one answer in response to said at least one personalized question and based upon the user's speech ability includes tracking a user via GPS coordinates on said remote device.

20. The system as in claim 18, wherein said microprocessor is configured to analyze a user's medical condition by determining using a grading system the user's condition based upon at least one answer in response to said at least one question and based upon the user's speech ability includes tracking a user via GPS coordinates on said remote device.

21. The system as claimed in claim 1, wherein the remote device is configured to trigger a help button on said remote device when the monitored user fails at said task; and notify another user of the user's movements by communicating GPS information about the remote device.

22. The system as in claim 1, wherein the remote device is configured to record the tapping of a user to determine their rhythmic ability by recording the user tapping on a screen of the remote device.

\* \* \* \* \*